United States Patent
Berg et al.

(10) Patent No.: US 6,656,695 B2
(45) Date of Patent: Dec. 2, 2003

(54) BIOMAP CHARACTERIZATION OF BIOLOGICALLY ACTIVE AGENTS

(75) Inventors: Ellen L. Berg, Palo Alto, CA (US); Eugene C. Butcher, Portola Valley, CA (US); Jennifer Melrose, La Honda, CA (US)

(73) Assignee: Bioseek, Inc., Burlingame, CA (US)

( * ) Notice: Subject to any disclaimer, the term of this patent is extended or adjusted under 35 U.S.C. 154(b) by 0 days.

(21) Appl. No.: 09/800,605

(22) Filed: Mar. 6, 2001

(65) Prior Publication Data

US 2003/0113807 A1 Jun. 19, 2003

Related U.S. Application Data

(60) Provisional application No. 60/186,976, filed on Mar. 6, 2000, and provisional application No. 60/195,672, filed on Apr. 7, 2000.

(51) Int. Cl.⁷ ........................ G01N 33/53; G01N 33/567
(52) U.S. Cl. ........................ 435/7.21; 435/7.24
(58) Field of Search ............................ 435/7.21, 7.24; 424/85.2, 85.1, 85.4, 85.5, 130.1, 143.1; 436/815, 50

(56) References Cited

U.S. PATENT DOCUMENTS

| | | |
|---|---|---|
| 4,568,649 A | 2/1986 | Bertoglio-Matte |
| 5,569,588 A | 10/1996 | Ashby et al. |
| 5,631,153 A | 5/1997 | Capecchi et al. |
| 5,777,888 A | 7/1998 | Rine et al. |
| 5,994,076 A | 11/1999 | Chenchik et al. |
| 6,004,755 A | 12/1999 | Wang |
| 6,013,437 A | 1/2000 | Luria et al. |
| 6,146,830 A | 11/2000 | Friend et al. |

OTHER PUBLICATIONS

Miller et al. Proc. Natl. Acad. Sci. vol. 94, pp. 2150–2155, Mar. 1997.*
Altschul et al. (Feb. 1994), "Issues in Searching Molecular Sequence Databases." *Nature Genetics,* vol. 6:119–129.
Blackstock et al. (Mar. 1999), "Proteomics: Quantitative and Physical Mapping of Cellular Proteins." *TIBTECH,* vol. 17:121–127.
Hatzimanikatis et al. (1999), "Proteomics: Theoretical and Experimental Considerations." *Biotechnol.,* vol. 15:312–318.
Mullner et al. (1998), "Proteomincs: A New Way for Drug Target Discovery."*Arzneim–Forsch.,* vol. 48(1):93–95.
Nellen et al. (Nov. 1993), "What Makes an mRNA Anti–Sense–Itive?" *TIBS,* vol. 18:419–423.

* cited by examiner

*Primary Examiner*—Prema Mertz
(74) *Attorney, Agent, or Firm*—Pamela J. Sherwood; Bozicevic, Field & Francis LLP

(57) ABSTRACT

A method of screening biologically active agent based on the analysis of complex biological responses in culture. Methods for selecting cells and culture conditions for such screens are provided, as well as the identification of an optimized set of discrete parameters to be measured, and the use of biomap analysis for rapid identification and characterization of drug candidates, genetic sequences acting pathways, and the like. A feature of the invention is simultaneous screening of a large number of cellular pathways, and the rapid identification of compounds that cause cellular responses.

16 Claims, 15 Drawing Sheets

- ☐ strong increase
- ▨ moderate increase
- ▒ unchanged
- ▨ moderate decrease
- ■ strong decrease

BIOMAP CHARACTERIZATION OF BIOLOGICALLY ACTIVE AGENTS

CROSS-REFERENCE TO RELATED APPLICATIONS

This application claims priority to U.S. Provisional Application No. 60/186,976, filed March 6, 2000; and to U.S. Provisional Application No. 60/195,672, filed Apr. 7, 2000.

FIELD OF THE INVENTION

The field of the invention is the discrimination between different cellular pathways and their use in the determination of the effect of agents on cell cultures.

BACKGROUND OF THE INVENTION

Pharmaceutical drug discovery, a multi-billion dollar industry, involves the identification and validation of therapeutic targets, as well as the identification and optimization of lead compounds. The explosion in numbers of potential new targets and chemical entities resulting from genomics and combinatorial chemistry approaches over the past few years has placed enormous pressure on screening programs. The rewards for identification of a useful drug are enormous, but the percentage of hits from any screening problem are generally very low. Desirable compound screening methods solve this problem by both allowing for a high throughput so that many individual compounds can be tested; and by providing biologically relevant information so that there is a good correlation between the information generated by the screening assay and the pharmaceutical effectiveness of the compound.

Some of the more important features for pharmaceutical effectiveness are specificity for the targeted cell or disease, a lack of toxicity at relevant dosages, and specific activity of the compound against its molecular target. Therefore, one would like to have a method for screening compounds or libraries of compounds that allows simultaneous evaluation for the effect of a compound on different cellular pathways, where the assay predicts aspects of clinical relevance and potentially of future in vivo performance.

While collecting information about multiple aspects of pharmacologic activity is useful because it provides a more complete analysis of the compound, it also makes the data analysis more difficult, because multiple parameters must be considered. Developments in computing technologies can provide solutions, but must be tied into the matrix of biological information.

In addition, cellular physiology involves multiple pathways, where pathways split and join, redundancies in performing specific actions and responding to a change in one pathway by modifying the activity of a different pathway. In order to understand how a candidate drug is acting and whether it will have the desired effect, it is necessary to know, not only the target protein with which the drug reacts, but whether the inhibition of the protein activity will result in the desired response. The development of screening assays that can provide better, faster and more efficient prediction of mechanisms of action, cellular effects and clinical drug performance is of great interest in a number of fields, and is addressed in the present invention. It is an object of the invention to provide a method for screening for inhibitors or modulators of cellular processes, which provide multiparameter information about the action of the agents tested on multiple cellular pathways.

Relevant Literature

In many assays, cell-free components such as enzymes and their substrates are used for compound screening. For example, U.S. Pat. No. 4,568,649 describes ligand detection systems which employ scintillation counting. In these methods, the therapeutic utility of compounds identified in such assays is presumed from a large body of other evidence previously identifying that a particular enzyme or target may be important to a disease process.

Cell based assays include a variety of methods to measure metabolic activities of cells including: uptake of tagged molecules or metabolic precursors, receptor binding methods, incorporation of tritiated thymidine as a measure of cellular proliferation, uptake of protein or lipid biosynthesis precursors, the binding of radiolabeled or otherwise labeled ligands; assays to measure calcium flux, and a variety of techniques to measure the expression of specific genes or their gene products.

Compounds have also been screened for their ability to inhibit the expression of specific genes in gene reporter assays. For example, Ashby et al. U.S. Pat. No. 5,569,588; Rine and Ashby U.S. Pat. No. 5,777,888 describe a genome reporter matrix approach for comparing the effect of drugs on a panel of reporter genes to reveal effects of a compound on the transcription of a spectrum of genes in the genome.

Methods utilizing genetic sequence microarrays allow the detection of changes in expression patterns in response to stimulus. A few examples include U.S. Pat. No. 6,013,437; Luria et al., "Method for identifying translationally regulated genes"; U.S. Pat. No. 6,004,755, Wang, "Quantitative microarray hybridization assays"; and U.S. Pat. No. 5,994,076, Chenchik et al., "Methods of assaying differential expression". U.S. Pat. No. 6,146,830, Friend et al. "Method for determining the presence of a number of primary targets of a drug".

Proteomics techniques have potential for application to pharmaceutical drug screening. These methods require technically complex analysis and comparison of high resolution two-dimensional gels or other separation methods, often followed by mass spectrometry (for reviews see Hatzimanikatis et al. (1999) *Biotechnol Prog* 15(3):312–8; Blackstock et al. (1999) *Trends Biotechnol* 17(3):121–7. A discussion of the uses of proteomics in drug discovery may be found in Mullner et at. (1998) *Arzneimittelforschung* 48(1):93–5.

Various methods have been used to determine the function of a genetic sequence. The initial effort is often performed from sequence information alone. Such techniques can reasonably determine if a new gene encodes a soluble or membrane-bound protein, a member of a known gene family such as the immunoglobulin gene family or the tetraspan gene family, or contains domains associated with particular functions (e.g. calcium binding, SH2 domains etc.). Multiple alignments against a database of known sequences are frequently calculated using an heuristic approach, as described in Altschul et al. (1994) *Nat. Genet.* 6:119.

Alternatively, "reverse genetics" is used to identify gene function. Techniques include the use of genetically modified cells and animals. A targeted gene may be "knocked out" by site specific recombination, introduction of anti-sense constructs or constructs encoding dominant negative mutations, and the like (see, for some examples, U.S. Pat. No. 5,631,153, Capecchi et al. for methods of creating transgenic animals; Lagna et a. (1998) *Curr Top Dev Biol* 36:75–98 for an overview of the use of dominant negative constructs; and Nellen et al. (1993) Trends Biochem Sci 18(11):419–23 for a review of anti-sense constructs).

Cells and animals may also be modified by the introduction of genetic function, through the introduction of functional coding sequences corresponding to the genetic sequence of interest. General techniques for the creation of transgenic animals may be found in *Mouse Genetics and Transgenics: A Practical Approach* (Practical Approach Series) by Ian J. Jackson (Editor), Catherine M. Abbott (Editor). While they have proven useful in many ways, however, transgenic animals frequently suffer from problems of time and expense, as well as compensatory mechanisms, redundancies, pleiotropic genetic effects, and the lethality of certain mutations.

Another approach for discovering the function of genes utilizes gene chips or microarrays. DNA sequences representing all the genes in an organism can be placed on miniature solid supports and used as hybridization substrates to quantitate the expression of all the genes represented in a complex mRNA sample, and assess the effect of a perturbation on gene expression. Methods utilizing genetic sequence microarrays can be applied to pharmaceutical target validation. In these methods, genetic modifications are evaluated for their effects on the expression of particular genes. A few examples include U.S. Pat. No. 6,013,437; Luria et al., "Method for identifying translationally regulated genes"; U.S. Pat. No. 6,004,755, Wang, "Quantitative microarray hybridization assays"; and U.S. Pat. No. 5,994,076, Chenchik et al., "Methods of assaying differential expression".

Gene reporter assays can also be used to characterize the effect of genetic modifications by their ability to inhibit the expression of specific genes in gene reporter assays. For example, Ashby et al. U.S. Pat. No. 5,569,588; Rine and Ashby U.S. Pat. No. 5,777,888 describe a genome reporter matrix approach for comparing the effect of drugs on a panel of reporter genes to reveal effects of a compound on the transcription of a spectrum of genes in the genome.

SUMMARY OF THE INVENTION

Methods and compositions are provided for function homology screening by discriminating between different cellular pathways, both as to the effect of genotype modification on cellular pathways and changes in parameters resulting from changes in the pathways, and using the discrimination for determining the effect of an agent on a mammalian cell culture system simulating cellular functions, as in a cellular state of interest, usually associated with a diseased state of a mammalian host. Cells capable of responding to factors and simulating the state of interest are employed, where the factors enhance the response of the measured components of the phenotype to approximate the response in vivo to external agents. A sufficient number of factors are employed to involve a plurality of pathways and a sufficient number of parameters are selected to be involved with a plurality of pathways and provide a robust response to the effect of a change in the environment of the cells. A flexible, multiplex screening assay is provided for screening and biological activity classification of biologically active agents. Assays are performed in the presence of an agent of interest, whereby a level of at least about 3 markers is obtained associated with the presence of the agent and the results compared to the level of the markers observed in the absence of the agent. By employing reagents that are known to have an effect on a pathway in conjunction with the agent, the pathway affected by the agent can be determined. The data resulting from the assays can be processed to provide robust comparisons between different environments and agents. Databases are provided so that agents and their effects may be compared. Particularly, biomaps are provided allowing for ready comparison,—visual, mathematical and electronic—of the results of different assays involving the same or different agents with assays involving the same or different reagents.

DESCRIPTION OF THE SPECIFIC EMBODIMENTS

Figure 1A:
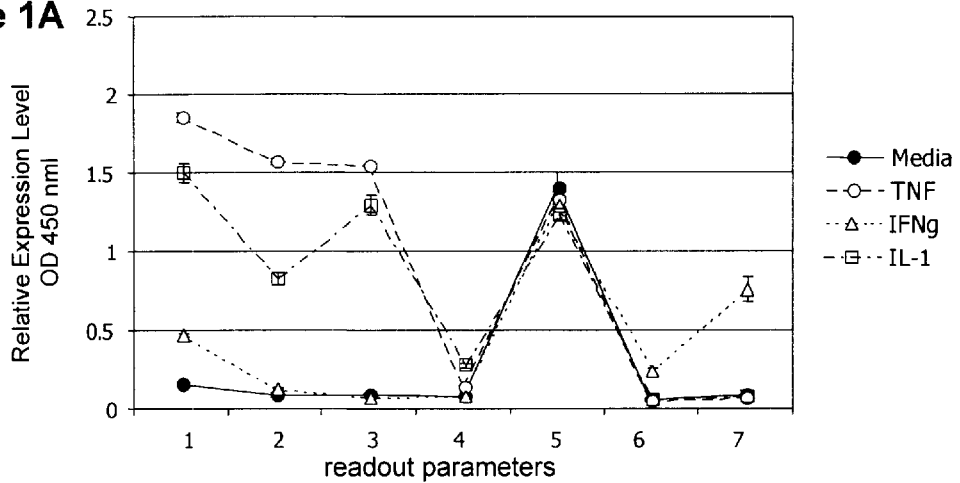
FIG. 1. Assay combinations for screening inflammatory modulators. A. Expression of selected readout parameters on selected assay combinations of HUVEC treated with prion-inflammatory cytokines. Confluent cultures of HUVEC cells were treated with TNF-$\alpha$ (5 ng/ml), IFN-$\gamma$ (100 ng/ml) or IL-1 (1 ng/ml). After 24 hours, cultures were washed and evaluated for the presence of the parameters ICAM-1 (1), VCAM-1 (2), E-selectin (3), IL-8 (4), CD31 (5), HLA-DR (6) and MIG (7) by cell-based ELISA. For this, plates were inverted until dry, blocked with 1% Blotto for 1 hr, and treated with primary antibodies (obtained from Pharmingen and Becton Dickinson) at 1 ng/ml for 1 hr. Plates were washed and secondary peroxidase-conjugated anti-mouse IgG antibody (Promega) at 1:2500 was applied for 1 hr. After washing, TMB substrate (Kierkegaard & Perry) was added and color developed. Development was stopped by addition of $H_2SO_4$ and the absorbance at 450 nm (subtracting the background absorbance at 650 nm) with a Molecular Devices plate reader. The relative expression levels of each parameter are indicated by the OD at 450 nm shown along the y-axis. The mean +/− SD from triplicate samples is shown. B. Expression of selected readout parameters on selected assay combinations of HUVEC treated with cytokine combinations. Confluent cultures of HUVEC cells were treated with TNF-$\alpha$ (5 ng/ml), IFN-$\gamma$ (100 ng/ml) or TNF-$\alpha$ and IFN-$\gamma$. After 24 hours, cultures were washed and evaluated for the presence of the parameters ICAM-1 (1), VCAM-1 (2), E-selectin (3), IL-8 (4), CD31 (5), HLA-DR (6) and MIG (7) by cell-based ELISA performed as described above. The relative expression levels of each parameter are indicated by the OD at 450 nm. The mean +/− SD from triplicate samples are shown. C. Expression of selected readout parameters on selected assay combinations of HUVEC treated with cytokine combinations. Confluent cultures of HUVEC cells were treated with TNF-$\alpha$ (5 ng/ml)+IFN-$\gamma$ (100 ng/ml) or TNF-$\alpha$ (5 ng/ml)+IFN-$\gamma$ (100 ng/ml)+IL-1 (1 ng/ml). After 24 hours, cultures were washed and evaluated for the presence of the parameters ICAM-1 (1), VCAM-1 (2), E-selectin (3), IL-8 (4), CD31 (5), HLA-DR (6) and MIG (7) by cell-based ELISA performed as described above. The relative expression levels of each parameter are indicated by the OD at 450 nm. The mean +/− SD from triplicate samples are shown. * indicates p<0.05 comparing results obtained with the two separate conditions, n=3.

Flexible multiplex screening assays are provided for the screening and biological activity classification of biologically active agents and genes.

In the screening assays for the biologically active agents, the effect of altering the environment of cells in culture is tested with a panel of cells and cellular environments. The effect of the altering of the environment is assessed by monitoring multiple output parameters. The result is an analysis providing "function homology," where comparison of two different environments, particularly differing by different compounds present in the environment, can be directly compared as to their similarities and differences. By being able to compare the effect on a family of parameters as to the degree of change in the absence of the compounds, the function of the compounds can be compared, the pathways affected identified and side effects predicted.

In the screening assays for genetic agents, polynucleotides are added to one or more of the cells in a panel in order to alter the genetic composition of the cell. The output parameters are monitored to determine whether there is a change in phenotype affecting particular pathways. In this way, genetic sequences are identified that encode or affect expression of proteins in pathways of interest, particularly pathways associated with aberrant physiological states.

Assay combinations, usually employing cell cultures, are provided that simulate physiological cell states of interest, particularly physiological cell states in vivo, usually using the same type of cells or combinations of cells. These cell cultures are created by the addition of a sufficient number of different factors to provoke a response that simulates cellular physiology of the state of interest and to allow for the status of cells in culture to be determined in relation to a change in an environment. The state of interest will normally involve a plurality of pathways where the pathways regulate a plurality of parameters or markers identifying a phenotype associated with the state of interest.

The phenotype can be generated by including a plurality of factors that induce pathways affecting the production of the phenotype by the up or down regulation of formation of the parameters as detectable products or may be based on the nature of the cell, e.g. neoplastic primary cells, cell lines, etc., where the factors enhance the response of the cells in vitro to more closely approximate the response of interest. The factors are naturally occurring compounds, e.g. known compounds that have surface membrane receptors and induce a cellular signal that results in a modified phenotype, or synthetic compounds that mimic the naturally occurring factors. In some instances, the factors will act intracellularly by passing through the cell surface membrane and entering the cytosol with binding to components in the cytosol, nucleus or other organelle. In providing the environment by use of the factors or mimetics, one provides the activities of the factors to the environment, using the naturally occurring factors or their mimetics. In referring to factors, it is understood that it is the activities of the factors that are of interest and not necessarily a particular naturally occurring factor itself.

The nature and number of parameters measured generally reflects the response of a plurality of pathways. The subject approach provides for robust results having enhanced predictability in relation to the physiological state of interest. The results may be compared to the basal condition and/or the condition in the presence of one or more of the factors, particularly in comparison to all of the factors used in the presence and absence of agent. The effects of different environments are conveniently provided in biomaps, where the results can be mathematically compared.

For screening assays with genetic agents, the same approach will be used as above. The genetic agents are added to cells, which are placed in a medium where one or more factors may be present to provide a desired environment, namely an environment of interest, such as a physiological environment involved with an aberrant, e.g. diseased, state. Parameters associated with the pathways related to the physiological state are monitored. Where the parameters show a pattern indicating the up or down regulation of a pathway, the genetic agent is deduced to encode or affect the expression of a member of the pathway. In this way one can determine the role a gene plays in the physiological state of interest, as well as define targets for therapeutic application.

Once biomaps have been prepared for pathways and/or environments of interest, assays may be carried out with or without the factors. Knowing the variation in parameters with individual factors and different combinations of factors, one can compare the effect of an agent on a cell culture by measuring parameters that have been previously measured in different assay combinations. The observed effect of the agent on the levels of the different parameters may then be correlated with the observed effect of the factors and combinations of factors in the biomap dataset.

Numerous factors are known that induce pathways in cells that are responsive to the factor. For the most part, factors bind to cell surface receptors, although other receptors may be involved, such as receptors at the nuclear membrane. In addition, where a factor is able to penetrate the surface membrane, through passive or active transport or through endocytosis, the factor may bind to components of the membrane, cytosol or an organelle, e.g. nucleus. It has now been found that by using a combination of multiple factors to provoke a cellular response, and multiple parameters associated with a physiological state of interest, one can investigate multiple individual cellular physiological pathways and simulate the physiological response to a change in environment and obtain greater predictability as to the way the physiological situation will respond to the change in environment. The subject screening of physiologically active compounds provides for greater assurance of the effect of the change of environment in the physiological circumstances in which the change is to occur.

Multiple factors are employed, which provides a robust simulation of the physiological state or physiologic pathways of interest and allows for reliable responses that can be correlated with in vivo cellular responses. Alternatively, factors can be employed that simulate the environment of the cells in vivo (particularly a living animal, but may be cells, tissue, organelles, etc.), so that the cell physiology of the cells in culture more closely approximates the cell physiology in vivo.

Combinations of factors are employed where pathways involved with a particular cellular status are active, resulting in the modulation of the formation of various products, such as RNA, e.g. mRNA, tRNA, etc., proteins, metabolites, functional states of proteins, etc., where different products are associated with different pathways. All of these products are detectable and can be analyzed by appropriate assays. Specific products are selected for measurement, usually avoiding products that give redundant information, e.g. that are commonly regulated. The results obtained from individual assay combinations may then be compiled. These results are compared or normalized with the control state, which can be the cells in an appropriate medium with or without exogenous factors other than the test agent, or the stimulated culture, which is the cells in the absence of the agent, but in same medium with the factors that induce the cells in culture to simulate cells in a complex environment that occurs in vivo. For the most part, the control state will be the cell culture with the same factors and measuring the same parameters as the test state comprising the agent.

In referring to simulation to a physiological state, the simulation will usually include at least three different regulated features (parameters) shared with in vivo cell counterparts in normal or diseased states. Alternatively, the simulation may include a cell culture system that allows discrimination of modifications in at least three different signaling pathways or cell functions operative in vivo under conditions of interest.

The results can be entered into a data processor to provide a biomap dataset. Algorithms are used for the comparison and analysis of biomaps obtained under different conditions. The effect of factors and agents is read out by determining changes in multiple parameters in the biomap. The biomap will include the results from assay combinations with the agent(s), and may also include one or more of the control state, the simulated state, and the results from other assay combinations using other agents or performed under other conditions. For rapid and easy comparisons, the results may be presented visually in a graph of a biomap, and can include numbers, graphs, color representations, etc.

Biomap

The biomap is prepared from values obtained by measuring parameters or markers of the cells in the presence and absence of different factors, as well as comparing the presence of the agent of interest and at least one other state, usually the control state, which may include the state without agent or with a different agent. The parameters include cellular products or epitopes thereof, as well as functional states, whose levels vary in the presence of the factors. Desirably, the results are normalized against a standard, usually a "control value or state," to provide a normalized data set. Values obtained from test conditions can be normalized by subtracting the unstimulated control values from the test values, and dividing the corrected test value by the corrected stimulated control value. Other methods of normalization can also be used; and the logarithm or other derivative of measured values or ratio of test to stimulated or other control values may be used. Data is normalized to control data on the same cell type under control conditions, but a biomap may comprise normalized data from one, two or multiple cell types and assay conditions.

By referring to a biomap is intended that the dataset will comprise values of the levels of at least two sets of parameters obtained under different assay combinations. Depending on the use of the biomap, the biomap may also include the parameter values for each the factors included in the assay combination, individually and/or together with fewer than the entire assay combination. Compilations of biomaps are developed that provide the values for a sufficient number of alternative assay combinations to allow comparison of values obtained where factors have not been added. While such an assay can be less predictive of in vivo conditions, in many situations it can suffice to provide a rapid, inexpensive screen providing useful data. For example, if one were interested in side effects of a candidate compound, by using a cell culture that is in a basal state, one could evaluate whether the candidate compound produced an aberrant state, e.g. normal as compared to inflamed. The parameter values are usually created electronically and stored in a data processor for comparison with other biomaps and databases compiled from the biomaps.

A graph of a biomap can be presented visually as numerical values, symbols, color gradations, or the like, indicating the parameter values. The graph is conveniently presented where color and/or design provide an indication of the level of the particular marker. The indicators may be vertical or horizontal as to the individual markers and the assay combinations, so that by looking at the graph, one can immediately compare the levels of the different markers for each of the combinations and discern patterns related to the assay combinations and the differences between assay combinations. In this way, one can rapidly relate different candidate pharmacologic agents, the pathways they affect and their efficacy in modulating the individual pathways.

Optionally, a biomap can be annotated to indicate information about the sources of information for the dataset. Annotations may include, for example, the number of assay conditions in a panel (n); controls used for normalization (N); parameters (P), which may be designated for the number and identity of the parameters; environmental changes, such as the addition of factors and/or agents or a change in the physical conditions (V); cell type (C); and the like. The annotation may further specify specific factors or conditions present in one of the assay combinations, e.g. n1, n2, n3, etc., where the presence of factors in the assay combination is designated (F), temperature may be designated (T), pH, etc. The parameters may also be designated in this as, e.g. P1=ICAM-1, P2=VCAM-1, P3=E-selectin, etc. Written out, the annotation may be set forth as: (v) B {n; N; P; C; F}.

As an example: a biomap is produced from monitoring endothelial cells for four parameters in four assay combinations. The assay combinations include a basal control, a stimulated control, and a control where the pathway of interest is blocked by the addition of neutralizing antibody. The compound being tested is an NSAID. The biomap (B) may be annotated as:

(NSAID) B {n=1–4; N=basal/stim.; P=1–4; C=endothelial; $F_{(n4)}$=neut. Ab}

A database of biomaps can be compiled from sets of experiments, for example, a database can contain biomaps obtained from a panel of assay combinations, with multiple different environmental changes, where each change can be a series of related compounds, or compounds representing different classes of molecules. In another embodiment, a database comprises biomaps from one compound, with multiple different cell panels.

Mathematical systems can be used to compare biomaps, and to provide quantitative measures of similarities and differences between them. For example, the biomaps in the database can be analyzed by pattern recognition algorithms or clustering methods (e.g. hierarchical or k-means clustering, etc.) that use statistical analysis (correlation coefficients, etc.) to quantify relatedness of biomaps. These methods can be modified (by weighting, employing classification strategies, etc.) to optimize the ability of a biomap to discriminate different functional effects. For example, individual parameters can be given more or less weight when analyzing the dataset of the biomap, in order to enhance the discriminatory ability of the biomap. The effect of altering the weights assigned each parameter is assessed, and an iterative process is used to optimize pathway or cellular function discrimination.

Assay Combination

Cells for use in the assays of the invention can be an organism, a single cell type derived from an organism, or can be a mixture of cell types, as is typical of in vivo situations, but may be the different cells present in a specific environment, e.g. vessel tissue, liver, spleen, heart muscle, brain tissue, etc. The cells will usually be of the same type as the cells of the physiologic conditions, sharing at least a partially common phenotype. For example, both the culture and the in vivo physiologic condition could involve T-lymphocytes, where the culture would involve a T-lymphocyte cell line or primary T-lymphocyte. In some instances the cells in the culture or assay combination may be substantially different from the cells of the physiologic state of interest. Where it is known or can be shown that the pathways of the cells in culture are paradigmatic of the pathways of the cells of interest, the cells in culture may be selected for reasons of convenience, that a body of data has been built up with these cells, easy growth and maintenance, the use by others allowing for more accurate comparisons of the results, etc.

Of particular interest are primary cells that can be used in a culture, where the primary cells of interest are, in effect, synchronized in their phenotype, by the use of the factors. When the cells are not in synchrony, an average value will be obtained. The culture conditions will include the presence of factors that provide for the desired physiologic state, including the desired phenotype, but may also be varied, for example, as to temperature, pH, presence of other cell types, and the like. Each combination of cell(s) and culture conditions provides one "assay combination", which will generate a set of parameter readouts. In a typical screen, a panel of one or more assay combinations is used for each compound to be tested. For each assay combination, a set of parameter readouts will be obtained in the presence of an agent that is being tested. These readouts will be compared to readouts of an assay combination lacking the agent, which may be performed contemporaneously or may be performed at another time, either before or after the assay combination with the agent of interest. As indicated above, the comparison may be with the same type of cells in the absence of the factors, in the presence of the factors, or multiple stimulating or inhibiting factors or in the presence of a different agent or other condition that serves to provide a meaningful comparison.

Single cell types are of interest for many screening applications, and in individual assay combinations will be provided with factors that induce the desired phenotype. The factors may be the products of other cell types, for example, expressed proteins associated with a disease, may be compounds that simulate naturally occurring factors, may be surface membrane proteins free of the membrane or as part of microsomes, or other reagent that induces the appropriate pathway to aid in the simulation of the phenotype or provides the appropriate environment to simulate the physiological condition. The factors (including mimetics thereof) may be added individually or in combination, from feeder cells, may be added as a bolus or continuously, where the factor is degraded by the culture, etc. Illustrative naturally occurring factors include cytokines, soluble receptors, hormones, prostaglandins, steroids, etc, that may be isolated from natural sources or produced by recombinant technology or synthesis, compounds that mimic the action of other compounds or cell types, e.g. an antibody which acts like a factor or mimics a factor, such as synthetic drugs that act as ligands for target receptors. For example, in the case of the T cell receptor, the action of an oligopeptide processed from an antigen and presented by an antigen-presenting cell, etc. can be employed. Where a family of related factors are referred to with a single designation, e.g. IL-1, VEGF, IFN, etc., in referring to the single description, any one or some or all of the members of the group are intended, where the literature will be aware of how the factors are to be used in the context of the assay combination.

The assay combinations find use in investigating complex states of cells, frequently resulting from cellular interactions, which may frequently involve at least about two, frequently three, or more different cell types and/or will involve a plurality of soluble factors that are present in a physiological fluid, particularly as the result of a physiological event, e.g. infection, neoplasia, autoimmune, etc. that is, frequently involving more than one cell type and more than one factor. The measured parameters may be obtained from one or more of the cell types. The cells in the assay combination, either one or up to each of the different cell types, can have identifying characteristics allowing them to be distinguished during analysis. Various techniques may be employed to identify the cells in the assay combination for analysis of the parameters of interest.

Conditions of interest include inflammatory processes that occur in response to infection, trauma, etc., autoimmune diseases, such as diabetes, lupus, arthritis, etc., cardiovascular diseases, such as stroke, atherosclerosis, etc., neoplasia, hyperplasia, addiction, infection, obesity, cellular degeneration, apoptosis, senescence, differentiation, and the like.

Multifactorial, usually involving multicellular, assay combinations, may reflect many of the conditions indicated above, such as inflammatory processes; autoimmune diseases; cardiovascular diseases; tumors, etc. That is, a multiplicity of factors are employed to influence a plurality of cellular pathways and a multiplicity of parameters are measured that reflect the status of the pathways. Degenerative diseases, including affected tissues and surrounding areas, may be exploited to determine both the response of the affected tissue, and the interactions with other cell types or other parts of the body.

The invention is suitable for use with any cell type, including primary cells, normal and transformed cell lines, transduced cells and cultured cells. The present invention is suitable for use with single cell types or cell lines; or combinations thereof. In assays the cultured cells may maintain the ability to respond to stimuli that elicit a response in their naturally occurring counterparts. Cultured cells may have gone through up to five passages or more, sometimes 10 passages or more. These may be derived from all sources, particularly mammalian, and with respect to species, e.g., human, simian, rodent, etc., although other sources of cells may be of interest in some instances, such as plant, fungus, etc.; tissue origin, e.g. heart, lung, liver, brain, vascular, lymph node, spleen, pancreas, thyroid, esophageal, intestine, stomach, thymus, etc.

In addition, cells that have been genetically altered, e.g. by transfection or transduction with recombinant genes or by antisense technology, to provide a gain or loss of genetic function, may be utilized with the invention. Methods for generating genetically modified cells are known in the art, see for example "Current Protocols in Molecular Biology", Ausubel et al., eds, John Wiley & Sons, New York, N.Y., 2000. The genetic alteration may be a knock-out, usually where homologous recombination results in a deletion that knocks out expression of a targeted gene; or a knock-in, where a genetic sequence not normally present in the cell is stably introduced.

A variety of methods may be used in the present invention to achieve a knock-out, including site-specific recombination, expression of anti-sense or dominant negative mutations, and the like. Knockouts have a partial or complete loss of function in one or both alleles of the endogenous gene in the case of gene targeting. Preferably expression of the targeted gene product is undetectable or insignificant in the cells being analyzed. This may be achieved by introduction of a disruption of the coding sequence, e.g. insertion of one or more stop codons, insertion of a DNA fragment, etc., deletion of coding sequence, substitution of stop codons for coding sequence, etc. In some cases the introduced sequences are ultimately deleted from the genome, leaving a net change to the native sequence.

Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of the targeted genes. A functional knock-out may also be achieved by the introduction of an anti-sense construct that blocks expression of the native genes (for example, see Li and Cohen (1996) Cell 85:319–329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration.

The genetic construct may be introduced into tissues or host cells by any number of routes, including calcium phosphate transfection, viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into cells.

A number of selection systems may be used for introducing the genetic changes, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk.sup.-, hgprt.sup.- or aprt.sup.-cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

The literature has ample evidence of cells involved with many physiological states of interest, factors involved in inducing changes in the phenotype, and markers resulting from the interaction between the factors and the target cells affected by the factors. Primary cells for tissues of interest are readily available commercially and can be expanded as required. Biopsies can serve as a source of cells, both normal and diseased cells.

Cell types that can find use in the subject invention, include endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells;, etc.; adipocytes, cells involved with particular organs, such as thymus, endocrine glands, pancreas, brain, such as neurons, glia, astrocytes, dendrocytes, etc. and genetically modified cells thereof. Hematopoietic cells will be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) *Journal of Cellular Biochemistry Supplement* 24:32–91). Included are different cell lines derived spontaneously, or selected for desired growth or response characteristics from an individual cell line; and may include multiple cell lines derived from a similar tumor type but from distinct patients or sites.

In addition, cells may be environmentally induced variants of single cell lines: e.g., a responsive cell line, such as a transformed endothelial cell line, split into independent cultures and grown under distinct conditions, for example with or without cytokines, e.g. IL-1, with or without IFN-$\gamma$, with or without endothelial growth factors, and in the presence or absence of other cytokines or combinations thereof. Each culture condition then induces specific distinctive changes in the cells, such that their subsequent responses to an environment change is distinct, yielding a distinctive biomap. Alternatively, the cells may be transduced or otherwise genetically modified cells.

The term "environment," or "culture condition" encompasses cells, media, factors, time and temperature. Environments may also include drugs and other compounds, particular atmospheric conditions, pH, salt composition, minerals, etc. The conditions will be controlled and the biomap will reflect the similarities and differences between each of the assay combinations involving a different environment or culture condition.

Culture of cells is typically performed in a sterile environment, for example, at 37° C. in an incubator containing a humidified 92–95% air/5–8% $CO_2$ atmosphere. Cell culture may be carried out in nutrient mixtures containing undefined biological fluids such as fetal calf serum, or media which is fully defined and serum free.

Some preferred environments include environments that discriminate or emphasize cell or tissue states associated with pathology in one or more diseases, for example, Th1 versus Th2 polarization of effector T cells; prothrombotic;

inflammatory (e.g. NFκB, upregulated TNF-β cytokine production, downregulated IL-10, TGFα, etc.; dysregulated proliferation (neoplasia); angiogenesis; etc.) Environments that facilitate discrimination of specific signaling pathways implicated in disease states are also of interest, e.g. NFκB, classic Th1 or Th2 induction environments, etc.

Physiologically Relevant Assay Combination

Cell culture conditions that reflect multiple aspects of a physiological state are termed herein a "representation" or "simulation" of the condition of interest, normally the in vivo condition. There are several important, and interrelated variables to be considered when setting up the in vitro counterpart conditions. These include the types of cells that are involved, the media employed, the conditions for the culture, the presence of biologically active factors in the cell's physiological milieu; and the phenotype of the cells, which may be determined both in the absence and presence of pharmacologic agents or for genetically modified and unmodified cells.

While a single cell can find use in an assay combination, normally the number of cells will be at least $10^2$, usually at least $10^3$, and conveniently are grown to confluence.

In many cases the literature has sufficient information to establish assay combinations to provide a useful biomap. Where the information is not available, by using the procedures described in the literature for identifying markers for diseases, using subtraction libraries, microarrays for RNA transcription comparisons, proteomic or immunologic comparisons, between normal and cells in the physiologic state of interest, using knock-out and knock-in animal models, using model animals that simulate the physiological state, by introducing cells or tissue from one species into a different species that can accept the foreign cells or tissue, e.g. immunocompromised host, one can ascertain the endogenous factors associated with the physiologic state and the markers that are produced by the cells associated with the physiologic state.

Once a biomap of the components of the assay combination have been shown to be relevant to a physiologic state of interest, biomap analysis can be used to optimize cell culture conditions that more accurately represent or simulate such physiologic state in vivo, e.g. in disease states of interest. That is, the values for various parameters from cells in vivo can be used as a template for the process of representing those same cells in culture. Additional markers can be deduced and added as a marker to the map. The greater the number of individual markers that vary independently of each other, the more robust the biomap. By optimizing culture conditions and selection of parameters, a biomap from a cell panel in vitro can be made representative of an in vivo phenotype. In other words, in vitro culture conditions can be manipulated in order to generate cells having a biomap that mimics the parameter readout obtained from similar cells in a specific in vivo state of interest. There will usually be employed for generation of the biomap at least about three parameter or marker readouts, more frequently 4 or more, generally not more than 20, more usually not more than about 10, that have similar response patterns in the in vitro and in vivo conditions. A larger number of shared parameters indicates a greater relevance of the cultured cells for the disease state and will usually be indicative of a plurality of pathways associated with the physiologic state in vivo. The parameters selected will permit the readout of at least 2, more usually, at least about 3 or more cell pathways.

If desired, the parameters of the biomap can be optimized by obtaining biomap parameters within an assay combination or panel of assay combinations using different sets of readout, and using pattern recognition algorithms and statistical analyses to compare and contrast different biomaps of different parameter sets. Parameters are selected that provide a biomap that discriminates between changes in the environment of the cell culture known to have different modes of action, i.e. the biomap is similar for agents with a common mode of action, and different for agents with a different mode of action. The optimization process allows the identification and selection of a minimal set of parameters, each of which provides a robust readout, and that together provide a biomap that enables discrimination of different modes of action of stimuli or agents. The iterative process focuses on optimizing the assay combinations and readout parameters to maximize efficiency and the number of signaling pathways and/or functionally different cell states produced in the assay configurations that can be identified and distinguished, while at the same time minimizing the number of parameters or assay combinations required for such discrimination.

There are established protocols for the culture of diverse cell types that reflect their in vivo counterparts. Protocols may require the use of special conditions and selective media to enable cell growth or expression of specialized cellular functions. Such methods are described in the following: Animal Cell Culture Techniques (Springer Lab Manual), Clynes (Editor), Springer Verlag, 1998; Animal Cell Culture Methods (Methods in Cell Biology, Vol 57, Barnes and Mather, Eds, Academic Press, 1998; Harrison and Rae, General Techniques of Cell Culture (Handbooks in Practical Animal Cell Biology), Cambridge University Press, 1997; Endothelial Cell Culture (Handbooks in Practical Animal Cell Biology), Bicknell (Editor), Cambridge University Press, 1996; Human Cell Culture, Cancer Cell Lines Part I: Human Cell Culture, Masters and Palsson, eds., Kluwer Academic Publishers, 1998; Human Cell Culture Volume II—Cancer Cell Lines Part 2 (Human Cell Culture Volume 2), Masters and Palsson, eds., Kluwer Academic Publishers, 1999; Wilson, Methods in Cell Biology: Animal Cell Culture Methods (Vol 57), Academic Press, 1998; Current Protocols in Immunology, Coligan et al., eds, John Wiley & Sons, New York, N.Y., 2000; Current Protocols in Cell Biology, Bonifacino et al., eds, John Wiley & Sons, New York, N.Y., 2000.

The cell surface expression of various surface and intracellular markers, including protein, lipid, nucleic acid, e.g. genetic markers, and carbohydrate is known for a large number of different types of cells, and can be used as a reference for establishing the exact phenotype of cells in vivo; for determining whether that same phenotype is present in the cultured cells, for determining the effect of an agent, particularly a pharmacologic agent, on the cells, and the like. The manner in which cells respond to an agent, particularly a pharmacologic agent, including the timing of responses, is an important reflection of the physiologic state of the cell.

For example, one might determine by histologic and antibody staining the phenotypes of cells in a biopsy sample from a chronically inflamed tissue. This information would be used to determine the types of cells that are present, and their physiologic state, e.g. activated, responding to a cytokine, etc. and their environment, e.g. presence of cytokines. A corresponding assay combination is then established from the information, which provides the relevant cells in the appropriate state. A biomap is then derived from the assay combination and controls to provide an in vitro culture as an appropriate surrogate for the in vivo state. Usually, an in vivo response will match multiple parameter values (i.e. up or down regulation of parameters) to similarly responding cells in a "representative" assay combination.

As indicated previously, for many physiologic states, cell types, factors and markers are known. In addition, concentrations having the desired induction of change in phenotype are also known. Also as discussed above, these conditions can be further optimized by making variations in concentrations, ratios, choice of markers, etc. to provide more accurate simulations of the naturally occurring physiological state. Assay combinations that represent in vivo states may go through an iterative process. Based on the information in the literature or independently derived, one devises an initial set of culture conditions, which includes combinations of known biologically active factors. Depending on the desired biomap, these factors can include cytokines, chemokines, and other factors, e.g. growth factors, such factors include GM-CSF, G-CSF, M-CSF, TGF, FGF, EGF, TNF-α, GH, corticotropin, melanotropin, ACTH, etc., extracellular matrix components, surface membrane proteins, such as integrins and adhesins, and other components that are expressed by the targeted cells or their surrounding milieu in vivo. Components may also include soluble or immobilized recombinant or purified receptors, or antibodies against receptors or ligand mimetics.

For cells, either primary cells or cell lines, that have the appropriate phenotype, e.g. neoplastic cells, factors will be used to provide an environment that simulates the environment of the neoplastic cells in vivo. Depending on the type of cancer, the cancer cells will be perfused with different factors based on the different cells in the environment of the tumor, as well as other factors in the blood induced by factors secreted by the neoplastic cells. Since the physiology of the cells is influenced by these factors, which in turn will influence the regulation of the parameters to be measured, providing these factors enhances the approximation of the cells in culture to the cells in vivo, providing for a more accurate readout of the effect of an agent on the cells. Many of these factors will be the same factors described above, but additional factors include factors associated with angiogenesis, such as angiogenin, angiopoietin-1, HGF, PDGF, TNF-α, VEGF, IL-1, IL-4, IL-6, IL-8 and fibronectin.

An initial set of readout parameters is selected, which normally includes parameters that are differentially produced, expressed, modulated or indirectly influenced in response to one or more of the components included in the environment. These parameters normally include molecules of functional importance to the cell and which are relevant to the state of interest. The readout response of cells is measured in response to a defined agent, usually the addition of a pharmacologic agent, although in some instances a targeted alteration in genotype or change in environment may be involved. The resulting biomap (normalized set of parameter values) comprising the presence and relative amount of the markers will simulate the biomap of the relevant cells in vivo. The assay conditions used to generate the biomap may be further refined to most closely match the biomap of the cells in vivo in the physiologic state of interest or mimic at least about 3 features of interest of such cells in vivo.

The same pattern of factors and parameters can be used with genetically modified cells, where the assay combination has the genetically modified cell as its variable. The genetically modified cells are scored for changes in parameters, as compared to the genetically unmodified cells. The results are used to develop a biomap, where the biomap of the genetically modified cell can be compared to one or the other or both of other genetically modified cells and assay combinations involving exogenous agents. The compiled database of biomaps can include both biomaps of genetic modifications, and biomaps for the effects of other compounds. The biomaps provide identification of the pathways involved, the relationship of the activities of exogenous agents to genes, and how the cell modifies its biology in relation to these changes.

Panels

For the most part, the biomap dataset will comprise data from a panel of assay combinations. The panel will be related to the purpose of the biomap and may include not only the information that has been developed substantially concurrently with the study, but also information that has been previously developed under comparable conditions. In one embodiment of the invention, a panel is comprised of at least one assay combination that provides for a representation of an in vivo state of interest, while other assay combinations in the panel are variants thereof. Frequently a panel will be used that is comprised of at least one assay combination that provides for simulation of multiple pathways of interest, while other assay combinations in the panel are variants thereof. In other embodiments, a panel may be comprised of multiple, different, in vivo representations; or multiple different environmental conditions designed to stimulate multiple cell functions and pathways. The number of combinations in a panel may vary with the particular use. For example, the minimum number of assay combinations will be two for a panel for initial screening that would comprise a single assay combination. A panel for determining how a compound affects multiple cellular pathways or functional cell responses will usually comprise a plurality of assay combinations, usually at least about 3, more usually at least about 6, frequently at least about 10, and may comprise as many as 20 or more unique assay combinations. A panel for characterizing the mechanism of action of an active compound will usually comprise a plurality of assay combinations, usually at least about 4, more usually at least 6, frequently at least about 10 and may be as many as 20 or more unique combinations.

Desirably, a panel will comprise at least one assay combination that represents a basal or normal physiological state of the cell of interest, which may have been developed prior to the particular biomap or as part of an assay series, or a state in the presence of the factors. Assay panels used in the screening methods of the invention can comprise one or more assay combinations that provide a cultured cell counterpart to an in vivo condition of interest, where the in vivo condition will be the normal state of a cell of interest, a cell in a state associated with disease, a state associated with an immune response, an infected state, an inflammatory state, a neoplastic state, and the like. Assay panels can also comprise one or more assay combinations designed to allow discrimination of multiple cellular pathways or functional responses of interest, e.g. because of their participation in physiologic states in vivo.

In one embodiment, the panel of cells and culture conditions includes variants of representative culture condition(s), where single specific changes are made in order to expand the biomap dataset, e.g. by providing combinatorial subsets of factor combinations in different culture wells, provision of known drugs in the culture medium, utilizing cell variants comprising targeted genetic changes, etc.

In another embodiment, the panel comprises culture conditions where multiple specific changes are made simultaneously to the representative environment, e.g. two or more changes, usually not more than about 6, more usually not more than about 4. Such changes are associated with the additional information that is engendered by the indicated variations. The variations can include the addition of known inhibitors of specific pathways. Where the presence of the inhibitor and the candidate drug result in no change in the modulation of the markers as compared to the absence of the candidate drug, then the candidate drug is in the same pathway inhibited by the inhibitor and the candidate drug will usually be at or upstream from the site of intervention of the inhibitor in the pathway. Where a different result is obtained with the presence of the candidate drug, then it is assumed that the candidate drug acts on a different pathway or may act downstream from the inhibitor in the same pathway.

Taking as an example the investigation of an inflammatory response, included in a panel can be (i) an assay combination that is representative of endothelial cells responding to the set of pro-inflammatory cytokines produced by activated monocytes; (ii) a combination that is representative of these same cells in the presence of an anti-inflammatory drug; (iii) a basal assay combination in the absence of proinflammatory cytokines; and (iv) variant assay combinations that lack specific cytokines or subsets of cytokines; etc.

Parameters

Parameters are quantifiable components of cells, particularly components that can be accurately measured, desirably in a high throughput system. A parameter can be any cell component or cell product including cell surface determinant, receptor, protein or conformational or post-translational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assay combinations, usually at least about 2 of the same assay combination will be performed to provide a value. Variability is expected and a range of values for each of the set of test parameters will be obtained using standard statistical methods with a common statistical method used to provide single values.

Markers are selected to serve as parameters based on the following criteria, where any parameter need not have all of the criteria: the parameter is modulated in the physiological condition that one is simulating with the assay combination; the parameter is modulated by a factor that is available and known to modulate the parameter in vitro analogous to the manner it is modulated in vivo; the parameter has a robust response that can be easily detected and differentiated and is not too sensitive to concentration variation, that is, it will not substantially differ in its response to an over two-fold change; the parameter is secreted or is a surface membrane protein or other readily measurable component; the parameter desirably requires not more than two factors to be produced; the parameter is not co-regulated with another parameter, so as to be redundant in the information provided; and in some instances, changes in the parameter are indicative of toxicity leading to cell death. The set of parameters selected is sufficiently large to allow distinction between reference patterns, while sufficiently selective to fulfill computational requirements.

For each assay combination, certain parameters will be functionally relevant and will be altered in response to test or reference agents or conditions, while other parameters may remain static in that particular combination. Biomaps will generally comprise only functionally relevant parameter information, although a static parameter may serve as an internal control. A typical biomap will comprise data from at least 3 functionally relevant parameters, more usually at least about 5 functionally relevant parameters, and may include 10 or more functionally relevant parameters, usually not more than about 30, more usually not more than about 20, parameters. In analyzing the data from the biomap, all of the parameters need not be weighed equally. Those parameters that are closely functionally associated with the disease state or pathophysiologic response, and/or with modulation of cell pathways of interest may be given greater weight in evaluating a candidate drug or a readout, as compared to other parameters that are suggestive, but do not have as strong an association.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one parameter while an inactive conformation of a receptor may comprise another, e.g. the active and inactive forms of heterodimeric integrin $\alpha_M\beta_2$ or Mac-1.

A parameter may be defined by a specific monoclonal antibody or a ligand or receptor binding determinant. Parameters may include the presence of cell surface molecules such as CD antigens (CD1–CD247), cell adhesion molecules including $\alpha_4\beta_7$ and other integrins, selectin ligands, such as CLA and Sialyl Lewis x, and extracellular matrix components. Parameters may also include the presence of secreted products such as lymphokines, including IL-2, IL-4, IL-6, growth factors, etc. (Leukocyte Typing VI, T. Kishimoto et al., eds., Garland Publishing, London, England, 1997); Chemokines in Disease: Biology and Clinical Research (Contemporary Immunology), Hebert, Ed., Humana Press, 1999.

For activated T cells these parameters may include IL-1R, IL-2R, IL4R, IL-12Rβ, CD45RO, CD49E, tissue selective adhesion molecules, homing receptors, chemokine receptors, CD26, CD27, CD30 and other activation antigens. Additional parameters that are modulated during activation include MHC class II; functional activation of integrins due to clustering and/or conformational changes; T cell proliferation and cytokine production, including chemokine production. Of particular importance is the regulation of patterns of cytokine production, the best-characterized example being the production of IL-4 by Th2 cells, and interferon-γ by Th1 T cells. The ability to shift cytokine production patterns in vivo is a powerful means of modulating pathologic immune responses, for example in models of EAE, diabetes, inflammatory bowel disease, etc. Thus, the expression of secreted cytokines may be a preferred class of parameters, detectable, for example, by ELISA analysis of the supernatants, etc.

Candidate Agents

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 $\mu$l to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening Methods

Agents are screened for biological activity by adding the agent to at least one and usually a plurality of assay combinations to form a panel of assay combinations, usually in conjunction with assay combinations lacking the agent. The change in parameter readout in response to the agent is measured, desirably normalized, and the resulting biomap may then be evaluated by comparison to reference biomaps. The reference biomaps may include basal readouts in the presence and absence of the factors, biomaps obtained with other agents, which may or may not include known inhibitors of known pathways, etc. Agents of interest for analysis include any biologically active molecule with the capability of modulating, directly or indirectly, the phenotype of interest of a cell of interest.

The initial screening, particularly a high-throughput screening, may utilize a panel comprising a single assay combination, while secondary and higher screenings will generally utilize several assay combinations in a panel.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

For identifying the mechanism of action and determining the cellular target, a test agent is evaluated in secondary or "biosite identifier" assay combinations. Secondary or "biosite identifier" assay combinations may be related to the primary assay combination, but contain specific and targeted alterations. These alterations include addition or deletion of specific assay components, genetic alterations, or inclusion of specific compounds or interventions. The mechanism of action of the test agent is accomplished when identical readout response patterns are obtained from assay combinations containing the test agent and assay combinations generated from known specific alterations of the assay combination. Alternative pathway activators include compounds, agents or interventions that stimulate the target pathway through specific components along the target pathway and can bypass upstream regulatory controls. The test agent is evaluated in these assay combinations and the pathway target step is identified as including the most upstream pathway component activator that is sensitive to test agent.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477–81). Thus, antibodies can be genetically modified to provide a fluorescent dye as part of their structure The use of high affinity antibody binding and/or structural linkage during labeling provides dramatically reduced non-specific backgrounds, leading to clean signals that are easily detected. Such extremely high levels of specificity enable the simultaneous use of several different fluorescent labels, where each preferably emits at a unique color. Fluorescence technologies have matured to the point where an abundance of useful dyes are now commercially available. These are available from many sources, including Sigma Chemical Company (St. Louis Mo.) and Molecular Probes (Handbook of Fluorescent Probes and Research Chemicals, Seventh Edition, Molecular Probes, Eugene Oreg.). Other fluorescent sensors have been designed to report on biological activities or environmental changes, e.g. pH, calcium concentration, electrical potential, proximity to other probes, etc. Methods of interest include calcium flux, nucleotide incorporation, quantitative PAGE (proteomics), etc.

Highly luminescent semiconductor quantum dots (zinc sulfide-capped cadmium selenide) have been covalently coupled to biomolecules for use in ultrasensitive biological detection (Stupp et al. (1997) Science 277(5330):1242–8; Chan et al. (1998) Science 281(5385):2016–8). Compared with conventional fluorophores, quantum dot nanocrystals have a narrow, tunable, symmetric emission spectrum and are photochemically stable (Bonadeo et al. (1998) Science 282(5393):1473–6). The advantage of quantum dots is the potential for exponentially large numbers of independent readouts from a single source or sample.

Multiple fluorescent labels can be used on the same sample and individually detected quantitatively, permitting measurement of multiple cellular responses simultaneously. Many quantitative techniques have been developed to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR) (Handbook of Fluorescent Probes and Research Chemicals, Seventh Edition, Molecular Probes, Eugene Oreg.).

Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

As an example, Luminex beads or other fluorescent beads, or beads varying in light scattering parameters can be conjugated to antibodies to cytokines or other parameters, or conjugated to protein receptors for parameters. The conjugated beads are added to the cells, cell lysate, or to the removed supernatant, allowing bead binding to target parameters. Also, fluorescent antibody to a distinct epitope of the target parameter is used to measure the level of target parameter bound. The fluorescence and light scatter characteristics of the beads constitute an identifier of the target parameter, and fluorescence derived from added antibody to the target parameter is an indication of the quantity of target parameter bound, and hence a readout of the individual parameter.

Flow cytometry may be used to quantitate parameters such as the presence of cell surface proteins or conformational or posttranslational modification thereof; intracellular or secreted protein, where permeabilization allows antibody (or probe) access, and the like. Brefeldin A is commonly utilized to prevent secretion of intracellular substances. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000. The readouts of selected parameters are capable of being read simultaneously, or in sequence during a single analysis, as for example through the use of fluorescent antibodies to cell surface molecules. As an example, these can be tagged with different fluorochromes, fluorescent bead, tags, e.g. quantum dots, etc., allowing analysis of up to 4 or more fluorescent colors simultaneously by flow cytometry. Plug-flow cytometry that has the potential to automate the delivery of small samples from unpressurized sources at rates compatible with many screening and assay applications, may allow higher throughput, compatible with high throughput screening, Edwards et al. (1999) Cytometry 37:156–9.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112–225; Kawamoto et al. (1999) Genome Res 9(12):1305–12; and Chen et al. (1998) Genomics 51 (3):313–24, for examples.

Identifiers of individual cells, for example different cell types or cell type variants, may be fluorescent, as for example labeling of different unit cell types with different levels of a fluorescent compound, and the like. If two cell types are to be mixed, one may be labeled and the other not. If three or more are to be included, each may be labeled to different levels of fluorescence by incubation with different concentrations of a labeling compound, or for different times. As identifiers of large numbers of cells, a matrix of fluorescence labeling intensities of two or more different fluorescent colors may be used, such that the number of distinct unit cell types that are identified is a number of fluorescent levels of one color, e.g., carboxyfluorescein succinimidyl ester (CFSE), times the number of fluorescence levels employed of the second color, e.g. tetramethylrhodamine isothiocyanate (TRITC), or the like, times the number of levels of a third color, etc. Alternatively, intrinsic light scattering properties of the different cell types, or characteristics of the biomaps of the test parameters included in the analysis, can be used in addition to or in place of fluorescent labels as unit cell type identifiers.

Data Analysis

The comparison of a biomap obtained from a test compound, and a reference biomap(s) is accomplished by the use of suitable deduction protocols, AI systems, statistical comparisons, etc. Preferably, the biomap is compared with a database of reference biomaps. Similarity to reference biomaps induced by assay combinations involving known pathway stimuli or inhibitors can provide an initial indication of the cellular pathways targeted or altered by the test stimulus or agent.

A database of reference biomaps can be compiled. These databases may include reference biomaps from panels that include known agents or combinations of agents that target specific pathways, as well as references from the analysis of cells treated under environmental conditions in which single or multiple environmental conditions or parameters are removed or specifically altered. Reference biomaps may also be generated from panels containing cells with genetic constructs that selectively target or modulate specific cellular pathways. In this way, a database is developed that can reveal the contributions of individual pathways to a complex response.

The effectiveness of pattern search algorithms in classifying biomaps can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting agent mechanisms and in vivo agent effects.

For the development of an expert system for selection and classification of biologically active drug compounds or other interventions, the following procedures are employed. For every reference and test pattern, typically a data matrix is generated, where each point of the data matrix corresponds to a readout from a parameter, where data for each parameter may come from replicate determinations, e.g. multiple individual cells of the same type. As previously described, a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e. data matrices) obtained from multiple repeated experiments. Classification rules are selected as correctly identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test biomaps to be effectively identified and classified. Several approaches for generating a sufficiently encompassing set of classification patterns, and sufficiently powerful mathematical/statistical methods for discriminating between them can accomplish this.

A database can be compiled by preparing biomaps using different combinations of a plurality of biologically active factors, in conjunction with biomaps involving the use of known agents having known effects and/or the use of genetically modified cells, where the genetic modification affects one or more of the pathways affected by one or more of the factors used to create the phenotype. For example, if the culture conditions selected to produce a specific in vitro reference pattern contain four biologically active agents, in addition to those present in the basal conditions of the normal or basal environment, a biomap would be generated from a panel of cells treated under all possible combinations of the 4 agents (15 assay conditions), typically using constant concentrations in each of the combinations. The extent of the database associated with assay combinations to screen candidates for specific phenotypes, e.g. indications, will vary with the nature of the phenotype, the amount of information desired, the complexity of the system, and the like.

The data from cells treated with specific drugs known to interact with particular targets or pathways provide a more detailed set of classification readouts. Data generated from cells that are genetically modified using over-expression techniques and anti-sense techniques, permit testing the influence of individual genes on the phenotype.

As indicated, agents may be analyzed in the absence of any factors or with a limited number of factors. The assay is performed as previously described and the values of the parameters can be compared to the biomap reflecting the values for the parameters of the physiologic state of interest, the values of the parameters for the response to one or more factors, and the basal response. In this way, the effect of the agent under physiological conditions can be evaluated. Similarly, one may have datasets compiled from combinations of agents to determine their effect when combined on cell physiology. Again, with a comparison of the values obtained for the parameters with the values obtained from the parameters with assay combinations employing factors, one can evaluate the effect of the agent combination on various cells in vivo.

A preferred knowledge database contains reference biomaps comprising data from optimized panels of cells, environments and parameters. For complex environments, data reflecting small variations in the environment may also be included in the knowledge database, e.g. environments where one or more factors or cell types of interest are excluded or included or quantitatively altered in, for example, concentration or time of exposure, etc.

Pathway Discrimination

Biomaps are useful for pathway discrimination where the biomaps associated with agents that have a common target and mode of action are reproducibly and robustly similar, where biomaps are associated with agents that stimulate or inhibit different pathways of interest reproducibly, and with biomaps that discriminate at least two, preferably three, and more preferably four or more different pathways in a common set of assay combinations.

Providing an agent to an assay panel results in a biomap that reflects the cellular response to that agent, produced by the stimulus acting on a target, or biosite, and through a signaling pathway, producing a change in the phenotype of the cell. A pathway may be defined for the purposes of the invention as a set of interacting cellular events that produces or contributes to a specific phenotype. Pathways are mediated by sets of interacting molecules of the cell. Variables that act on the same cellular pathway result in similar biomaps. Similarly, variables that act on different cellular pathways result in different biomaps. Variables that act on multiple pathways can stimulate pathway interactions and thus also yield distinctive biomaps. It is not necessary for the purposes of the invention that the cellular pathway is known.

Comparison of a biomap produced by the action of an agent in a panel, to biomaps in the database, will indicate whether the variable yields a cellular state similar to those generated by other conditions, and thus may indicate a mechanism of action in the cell, and/or may indicate specific relevance of the biological activity to a particular disease or other state.

Importantly, compounds that alter therapeutically relevant parameters are of potential interest as drugs. For example, compounds that inhibit cytokine up-regulation of inflammatory cytokines or of molecules (adhesion molecules, chemokines, etc.) involved in leukocyte trafficking to inflamed tissues may have therapeutic value in inflammatory diseases. Compounds that inhibit oncogenic proteins, transcription factors involved with pathways essential to neoplastic proliferation, cyclins, kinases, etc., indicate initial interest as drugs for the treatment of cancer. Compounds that enhance pathways associated with cholesterol metabolism and transport may have therapeutic value in cardiovascular diseases.

Optimization Techniques

Optimized assay combinations can be developed by repeating the procedure of testing parameter readouts in response to stimuli until the selected disease-relevant environment is sufficiently differentiated from the normal or another selected condition and an optimized parameter set is selected.

Optimization of an initial assay combination includes the identification of optimal concentrations of added biologically active agents, the timing of their addition, addition or deletion of factors, and selection of an optimal time course. The time course will depend upon whether one is interested in the effect of an agent prior to the addition or at the time of the addition of the factors influencing the parameters or after the physiological condition has been established, as well as having cells that do and do not present the physiologic condition. The factors may have been present from about 0 to 72 h or longer prior to the addition of the agent, usually from about 0 to 48 h, and frequently from about 0 to 24 h. Where the cells may be at various stages of the physiologic condition, e.g. unchanged, intermediate stage and final stage the factors will usually have been present from about 2 to 48 h or longer, more usually from about 6 to 24 h. Optimization also includes modification of the basal medium (e.g. the addition or removal of particular growth factors, extracellular matrix components etc.) to reflect differences between physiologic states of interest.

For the most part, the concentration of the factors for providing the physiologic condition will be known and frequently the response will not be sensitive to small changes in the concentration. Where the concentration has not been reported, one can determine a useful concentration by determining the concentration that provides saturation. This can be achieved using cells and titrating the number of receptors with a labeled factor, e.g. fluorescent labeled factor. Once the saturation level is known, one may cut back to about 25 to 75% of the saturation value and determine the response by analyzing for the parameters of interest and the effect of the reduced concentration as compared to the response at saturation. Alternatively, take the factor to a plateau of a dependent functional response, add more or less to define levels maximal to response measures.

Active compounds alter the cellular responses and readout patterns when included in a selected assay combination.

Such alteration may include returning the levels of one or more parameters to their levels in the basal condition, or otherwise altering the cellular responses, particularly when such alterations reflect changes towards a desirable cellular state (e.g. converting Th1-like to Th2-like response, or vice versa).

Optimal assay combinations yield information about multiple different pathways of interest in regulation of inflammatory processes. Conditions based on initial combinations are developed to better reflect the physiologic or disease-relevant environment. Optimized assay combinations are developed by repeating the procedure to produce a biomap, evaluating additional combinations of biologically active agents and/or different parameters, until the biomap produced under the selected disease-relevant environment is sufficiently differentiated from the biomap of the normal or another selected condition and an optimized parameter set is selected.

Cell Families

Endothelial Cells

As exemplary of the subject situation, primary endothelial cells are employed in one embodiment of the invention, as these cells respond to a large variety of cellular stimuli. Endothelial cells are highly sensitive to their environment, and they contain a large number of signaling pathways. This provides an opportunity to evaluate the effect of compounds on many pathways and/or pathway interactions. Endothelial cells participate in many disease processes. In inflammation, they control the migration and localization of effector leukocytes and lymphocytes; in cancer, they control the nutrition of tumors and dissemination of metastases; and their dysregulation is centrally important to cardiovascular disease.

The present invention is useful for identifying regulators of inflammation using human endothelial cells as an indicator cell type. Endothelial cells are found in inflammatory tissues; they are highly responsive to environmental stimuli; and they are a cell type for which primary cells can be readily isolated and cultured such that they retain responsiveness to many of the biologically active factors important to inflammatory and other processes. Vascular endothelial cells are a preferred cell type because they participate in the inflammatory disease process by regulating the type of leukocytes that are recruited to the target tissue. The specificity of recruitment is determined by the combinatorial expression of adhesion molecules and chemokines. A set of culture systems or assay combinations that mimic the response of the endothelial cells to different types of inflammatory processes have been developed in vitro using the methods of the invention.

A number of factors are known to be associated with endothelial cells, such as EGF, FGF, VEGF, insulin, etc., cytokines, such as the interleukins, including IL-1 IL-3, IL-4, IL-8 and IL-13; interferons, including IFN-α, IFN-β, IFN-γ; chemokines; TNF-α, TGFβ, proangiogenic and anti-angiogenic factors, etc. (See *Current Protocols in Immunology*, supra.).

Endothelial cells in inflammatory tissues from chronic inflammatory disease patients differ from endothelial cells in normal tissues by increased expression parameters including ICAM-1, E-selectin, IL-8 and HLA-DR [Nakamura S, Lab Invest 1993, 69:77–85; Geboes K, Gastroenterology 1992, 103:439–47; Mazzucchelli L, J Pathol 1996, 178:201–6]. In addition, each of these parameters has been demonstrated to function in the inflammatory disease process. ICAM-1 and E-selectin are cell adhesion molecules that contribute to the localization and activity of inflammatory cells including T cells, monocytes, and neutrophils. IL-8 is a neutrophil chemoattractant and HLA-DR participates in the activity of pathologic T cells. Other cell surface or secreted parameters include parameters that are known to be regulated by factors, such as VCAM-1, which is induced on endothelial cells by TNF-α or IFN-γ; IL-10 and MIG which are induced on endothelial cells by IFN-γ; or GRO-α or ENA-78 which are induced on endothelial cells by IL-1 and/or TNF-α [Goebeler M, J Invest Dermatol 1997, 108:445–51; Piali L Eur J Immunol. 1998, 28:961–72].

For assay combinations representative of chronic inflammatory diseases, the cytokine IL-1 is often found in combination with TNF-α and IFN-γ in such diseases, for example, in Crohn's disease (Autschbach, 1995, Virchows Arch. 426:51–60). For this inflammation model of endothelial cells, an inhibitor of TNF-α, such as a neutralizing antibody against TNF-α, provides an example of an active compound. Adding anti-TNF-α to the assay combination was shown in reduced expression levels of ICAM-1; VCAM-1; and E-selectin; and increased expression levels of CD31.

Assay combinations that include genetically modified cells are also a preferred source of reference patterns. For example, TNF-α signaling in HUVEC involves the NFκB signaling pathway (Collins, 1995, Faseb J, 9:899). Blockade of this pathway can be accomplished by overexpression of IκB-α, for example, through adenoviral gene transfer (Weber, 1999, Blood 93:3685). HUVEC overexpressing IκB-A express reduced levels of ICAM-1 or E-selectin in response to TNF-α. However, because other cytokines, such as IL-1, can also signal through NFκB, readout patterns due to TNF-α inhibition can be distinguished from readout patterns that reflect NFκB inhibition.

By a similar iterative process as that described above, appropriate assay combinations for endothelial cells representing other inflammatory, disease, or physiologic states are established. These conditions include: psoriasis, rheumatoid arthritis, or chronic Th2 disease environments such as asthma, allergy or ulcerative colitis. A chronic Th2 assay combination can be defined by the culture of HUVEC with TNF-α and/or IL-1 and IL-4 for 24 hours. Inflammation in chronic Th2 environments, such as asthma, is characterized by the presence of TNF-α, IL-1 and IL-4, but not IFN-γ [Robinson, 1993, J. Allergy Clin. Immunol. 92:313]. HUVEC cultured for 24 hours with TNF-α and IL-4 express high levels of VCAM and MCP-1, similar to the in vivo situation [Ohkawarea, 1995, Am J. Resp. Cell Mol. Biol. 12:4; Rozyk, 1997, Immunol. Lett. 58:47].

Lymphokine-producing activated lymphocytes (CD45RO+, CD44hi, etc.) are a hallmark of inflammatory diseases including psoriasis, rheumatoid arthritis, Crohn's disease, ulcerative colitis, asthma, etc. Depending on the disease environment and tissue site, activated lymphocytes can differ in their expression and function of adhesion molecules and other receptors, as well as in their production of various cytokines and other factors. The ability to selectively block lymphocyte activation associated with the inflammatory disease without inhibiting or suppressing lymphocyte activation associated with the ability to fight infection and neoplasia is a goal of inflammatory drug therapy.

Specific homing and adhesion receptors, as well as chemokine receptors, expressed by lymphocytes differentiating into effector and memory cells target the involved regulatory and cytotoxic T cell populations, as well as B cells responsible for humoral immunity. Upregulation and modulation of homing receptor expression patterns is observed when lymphocytes are activated in defined microenvironments comprising specific cytokines; and in some environments multiple homing receptors (e.g., $\alpha_4\beta_7$, the cutaneous lymphocyte antigen ("CLA"), inflammatory chemokine receptor such as CCR5 and CXCR3 and bonzo, etc.) are induced. Multiplex analysis of each of these homing receptor parameters, which may also be performed in conjunction with other known or discovered parameters in reflecting the cellular state of activation, can be used to select immunomodulatory compounds capable of shifting patterns of homing receptor expression in a common microenvironment. Such modulators of lymphocyte targeting can be powerful immunosuppressives for localized immune pathologies, as in inflammatory bowel diseases, psoriasis, multiple sclerosis, arthritis, and the like; modulating patterns of lymphocyte homing/targeting molecules they would modulate in vivo immune responses therapeutically without the side effects associated with generalized immunosuppression.

The present invention can be applied to screening for drugs that block selective leukocyte activation pathways. Cells can be normal lymphocytes or lymphocyte subsets isolated from human blood or tissues according to standard methods (Current protocols in Immunology), or cell lines selected for their ability to respond in a similar fashion as do normal cells, or other cells.

The assay conditions for these cells include (1) known activation conditions ((combinations of anti-CD3+IL-2+/−IL-4+/−IFN-γ+/−IL-12+/−anti-IL-4 or anti-IFN-γ). Such conditions are given in: T Cell Protocols: Development and Activation (Methods in Molecular Biology, 134), Kearse, Ed., Humana Press, 2000.); (2) culture conditions that represent in vivo disease environments; or (3) conditions that emphasize or discriminate known signaling pathways or specific signaling pathways implicated in disease states. Assay combinations and reference biomaps are identified for a variety of diseases, including psoriasis, arthritis, Crohn's disease, ulcerative colitis, asthma, etc. by the iterative process as described in Example 1, of defining environmental conditions and initial parameter sets from in vivo data, testing assay combinations in vitro, comparing the in vitro and in vivo biomaps, optimizing the assay combination and selection of an optimal parameter set.

The disease environment in psoriasis includes IL-12, IFN-γ and TNF-α (Yawalker, 1998, J. Invest. Dermatol. 111:1053; Austin, 1999, J. Invest. Dermatol. 113:752), therefore an assay combination for psoriasis will include one or more, usually at least two, and frequently all of these factors. Inflammatory T cells in psoriasis express high levels of the CLA antigen, a carbohydrate antigen related to Sialyl Lewis x (Berg, 1991, J. Exp. Med. 174:1461; Picker, 1990, Am. J. Pathol. 136:1053). Therefore a parameter set for psoriasis will contain the CLA antigen.

The disease environment in Crohn's disease includes IL-1, TNF-α, IL-6, IL-8, IL-12, IL-18, and IFN-γ (Daig, 1996; Woywodt, 1994; Kakazu, 1999; Pizarro, 1999; Monteleone, 1999), therefore an assay combination for Crohn's disease will include one or more of these factors, generally including at least two of the IL factors, by themselves or in combination with at least one of IFN-γ and TNF-α. T cells in inflammatory bowel disease express high levels of the E7 integrin (Elewaut, 1998, Scand J. Gastroenterol, 33:743), therefore the parameter set for inflammatory bowel diseases preferentially contains E7.

The disease environment in rheumatoid arthritis includes TNF-α, IL-1, IL-6, IL-10, IL-15, MIP1, MCP-1, and TGF (Robinson, 1995, Clin. Exp. Immunol. 101:398; Thurkow, 1997, J. Pathol. 181:444; Suzuki, 1999, Int. Immunol, 11:553), therefore an assay combination for arthritis will include one or more of these factors, generally including at least two of the IL factors and at least one of MIP1 and MCP-1. T cells in rheumatoid arthritis synovial fluid express CCR5 and CXCR3 (Suzuki, 1999; Qin, 1998, J. Clin. Invest. 101:746; Loetscher, 1998, Nature 391:344), therefore the parameter set for rheumatoid arthritis preferentially contains CCR5 and CXCR3.

The disease environment in asthma includes IL-la, IL-4, IL-5, IL-6 and GM-CSF (Miadonna, 1997; Walker, 1994), therefore, an assay combination for asthma will contain one or more of these factors, generally including at least two of the IL factors and GM-CSF.

Once the optimal environmental conditions representing the target disease are determined, cells are treated with candidate drugs in those environments and the selected parameters are measured. Comparing the biomaps obtained in the presence of drugs with reference biomaps enables the identification of drugs that inhibit lymphocyte responses to complex environments, and enables them to be differentiated from drugs that act on selective pathway components. The multiplex living response systems allows simultaneous analysis of multiple activation-associated parameters, and Th1 versus Th2 phenotypes; as well as comparison of the effects candidate drugs have on T cell activation programs with their effects on properties of other cells in the living response system utilized. As an example, in its simplest embodiment, normal human T cells or blood lymphocytes are incubated in an activating and/or differentiating environment, contacted with an agent, and the readout output patterns compared with reference patterns obtained under control conditions (without the compound) and in the presence of prototypical anti-inflammatory compounds etc.

This is accomplished by developing a database of reference biomaps developed from the analysis of cells treated under environmental conditions in which single components are removed, or with known drugs that target specific pathways. Alternatively, reference biomaps are generated in the presence of genetic constructs that selectively target, stimulate, inhibit or otherwise modulate specific pathways. In this way, a database of reference biomaps is developed.

One preferential application of the invention is in immune deviation. Certain inflammatory diseases result or are exacerbated by polarization of an inflammatory response towards Th1 or Th2. For example, conditions that promote Th1 responses (e.g. systemic treatment with IFN-γ) exacerbate certain diseases such as multiple sclerosis. By the procedure given above, compounds can be screened for their ability to shift biomaps from "Th1" to "Th2", vice versa, or from "Th1" or "Th2" to other phenotypes.

The invention is also useful for screening compounds for drug interactions. For example, methotrexate is a current therapy for rheumatoid arthritis and inhibits T cell proliferation. Screening compounds in the presence of methotrexate can reveal unexpected toxicities or beneficial synergies.

The present invention can be applied for the identification of compounds that induce lymphocyte activation. For this application, drug compounds may be screened for their ability to induce particular reference biomaps. Such compounds would have clinical utility as immune stimulants, for vaccine protocols and other applications.

The present invention can be applied to the identification of compounds that stimulate or inhibit lymphocyte apoptosis. A variety of culture conditions are known to induce apoptosis in particular cell types. For example, radiation; inclusion of FasL in the culture; or other apoptosis inducing agent, can induce apoptosis of FasR (CD95) expressing T cells; TNF-α can induce apoptosis under specific conditions; a conformational change in ICAM-3, resulting in a change in ligand preference (from LFA-1 to a macrophage receptor) is associated with apoptosis in activated T cells, etc. The ability of a drug or intervention to induce apoptosis has applications for therapy of lymphoma and leukemia as well as autoimmune disease. Defining biomaps associated with apoptosis are useful for identifying active compounds.

Macrophage

The present invention can be applied to the identification of compounds that inhibit or alter macrophage activation. Peripheral blood monocytes, tissue macrophages and related cell lines are a preferred cell type for screening for pharmacologically active compounds/interventions due to their ability to discriminate pathophysiological environments. Monocytes/macrophages in different physiological settings have altered responses. IL-4 reduces production of IL-10 in LPS stimulated blood monocytes but not in synovial monocyte/macrophages (Bonder (1999) Immunol. 96:529; Ju (1999) Int. Rev. Immunol. 18:485). In addition to being highly responsive to their environment, monocytes/macrophages participate in a variety of disease processes, including inflammation, fibrosis, and wound healing, through their production of mediators, growth factors, phagocytosis and antigen presentation functions. Assay combinations, e.g. IL-4 and other IL factors, M-CSF, and GM-CSF are used in combination with each other or other factors associated with the physiologic or disease environments of interest and readout parameter sets are selected that allow different states to be distinguished. Readout parameters include integrins, adhesion molecules, and the like. Compounds are added to selected assay combinations, parameters are measured and the resulting test patterns are compared to reference biomaps. Reference patterns, held in a knowledge database include those developed from the analysis of cells treated under environmental conditions in which single components are removed, or with known drugs that target specific pathways. Alternatively, reference biomaps can be generated in the presence of genetic constructs that selectively target, stimulate, inhibit or otherwise modulate specific pathways. In this way, a database of reference biomaps is developed, and compounds are selected by their ability to produce a desired biomap.

Mast Cell

The present invention can be applied to the identification of compounds that inhibit or alter mast cell activation. Such compounds have utility in the treatment of allergy and asthma, where mast cell products mediate disease pathology (Galli, 2000, Curr. Opin. Hematol. 7:32). Mast cells display altered responses depending on their environment. The ability of mast cells to produce IL-3 and GM-CSF is significantly increased in the presence of fibronectin or vitronectin (Kruger-Krasagakes, 1999, Immunology, 98:253). Mast cells in allergen-induced late-phase cutaneous reactions in atopic patients express high levels of the high affinity IgE receptor compared with mast cells in control skin (Ying, 1998, Immunology 93:281). Assay combinations including at least one of fibronectin and vitronectin are developed that reflect physiologic or disease environments and readout parameter sets, including at least one of IL-3, GM-CSF, and IgE-receptor, are selected that allow different states to be distinguished. Compounds are added to selected assay combinations, parameters are measured and the resulting test patterns are compared to reference biomaps. Reference patterns, held in a knowledge database include those developed from the analysis of cells treated under environmental conditions in which single components are removed, or with known drugs that target specific pathways. Alternatively, reference biomaps can be generated in the presence of genetic constructs that selectively target, stimulate, inhibit or otherwise modulate specific pathways. In this way, a database of reference biomaps is developed, and compounds are selected by their ability to produce a desired biomap.

Cancer Applications a. Cytolytic/Cytostatic Compounds

The unique comparisons between panels of cell types holds the potential to provide therapeutically important information, and allow subclassification, of drugs and genes that can inhibit neoplastic cell proliferation, alter the immunogenicity, or modulate other critical features for cancer therapy. A panel of 60 neoplastic cell lines at the NCI has been used to examine the effects of hundreds of anti-cancer and other compounds on neoplastic cell proliferation (Weinstein, 1997, Science 275:343). While the responses of any individual cell line carried little information about the mechanism of inhibition of proliferation, the patterns of responses among the 60 cells of the panel demonstrated a robust ability to distinguish between compounds targeting different mechanisms, and thus to characterize the mechanisms of action of novel drugs as well, by comparison with reference tumor panel response patterns.

The present invention is applied by identifying subsets of the 60 NIH cell lines, and other cell lines that can provide robust discriminatory power for identifying and subclassifying anti-cancer agents. The responses of cell surface proteins and/or secreted products such as chemokines and other cytokines and the like, is determined under environmental conditions supportive of the neoplastic proliferative phenotype. Breast cancer environments involve certain growth factors, e.g. angiogenic factors and cytokines, such as IL-10 (Merendino 1999, 68, 355). Alterations in the selected parameters by contact of the cells with anti-cancer agents is used to define reference biomaps characteristic and diagnostic of individual drugs or mechanisms of action. The use of cell surface parameters to identify cytotoxic and cytostatic states allows a panel of cells to be evaluated in parallel. Biomaps are generated from known anti-cancer agents including DNA synthesis inhibitors, nucleoside analogs, topoisomerase inhibitors, microtubule function inhibitors etc. Such compounds are given in Weinstein, 1997, and The Pharmacologic Basis of Therapeutics. Reference patterns that distinguish compounds that are cytostatic or cytolytic versus apoptosis-inducing are developed using a panel of primary tumors and tumor cell lines with and without functioning p53 pathways. The procedure of simultaneous multiplex analyses of normal and cancer cell lines allows discrimination of agents selective for cancer cells.

The invention is also useful for screening compounds for drug interactions and synergies. Drug interactions are highly important in cancer therapy. For example, while steroids control the edema that occurs with glioma, they also interfere with chemotherapy efficacy. Cytotoxic drugs are a main treatment for cancer and interference with the chemotherapy efficacy may offset the anti-tumor effect of an apoptosis inducer. On the other hand, synergy between individual drugs would be highly beneficial, perhaps allowing reduced doses of the individual drugs and reducing the side effects.

b. Inhibitors of Metastatic Phenotype

The present invention can be applied to the identification of compounds or interventions that alter metastatic phenotypes of cancer cells. Metastatic cancers have altered adhesive and invasive functions. Metastatic cancers are associated with certain features including expression of various oncogenes, such as H-ras, increased levels of proteolytic enzymes, such as TPA (tissue plasminogen activator), production of osteopontin, and altered adhesion molecule expression and function. For example, carcinomas preferentially express $\alpha_6\beta_1$ and less $\alpha_2\beta_1$, $\alpha_3\beta_1$ and $\alpha_5\beta_1$ (Chambers 1993, Crit. Rev. Oncol. 4:95; Dedhar, 1995, Cancer Metastasis Rev. 14:165; Tuck, 1999, Oncogene 18:4237). Simultaneous multiplex analyses of normal and cancer cell lines allows discrimination of agents that selectively modulate the metastatic phenotype.

c. Inducers of Differentiative Phenotypes.

There is a general inverse relationship between the degree of cellular differentiation and the rate of cell proliferation in tumors. Several anti-cancer agents stimulate the differentiation and inhibit proliferation of malignant cells, including retinoids, various cytokines and analogs of vitamin D (Bollag, 1994, J. Cell Biochem. 56:427). All-trans retinoic acid, an agent that induces differentiation, gives a high rate of complete clinical remission in the treatment of acute promyelocytic leukemia (Tallman, 1994, Semin Hematol 31 (Suppl 5):38). Agents that stimulate differentiation are not easily detected using traditional in vitro assays of anticancer drug activity.

d. Apoptosis of Tumor Endothelial Cells.

The present invention can be applied to the identification of compounds that induce apoptosis of tumor endothelial cells. For this application, environmental conditions that induce a tumor endothelial cell phenotype on cultured endothelial cells are selected. Typically these environments are proangiogenic and contain a variety of growth factors, such as TGFβ, VEGF and basic FGF, as well as other tumor or other cell derived factors, where these factors can be used in the assay combination. Tumor endothelium differs from other endothelium by increased expression of $\alpha_v\beta_3$. A set of conditions that induce apoptosis of these cells is evaluated and a set of parameters that defines a biomap diagnostic of apoptosis is identified. Apoptotic conditions are identified as those that induce DNA laddering, and other well described features. These include simple culture conditions that contain one or more factors known to induce or promote endothelial cell apoptosis in vitro, such as ceremide, the combination of TNF-α and heat shock or sodium arsenite, TNF-α+IFN-γ, oxysterols; TNF-α in the presence of cyclohexamine, etc. (See Ruegg (1998) Nat. Med. 4:408). Parameters that may be included in the selected set include a variety of molecules involved in adhesion and proteolysis (since a prominent feature of apoptotic endothelial cells is their release from the vessel wall), those that can be modulated by individual factors, such as E-selectin, ICAM-1, VCAM and HLA-DR, and molecules or determinants known to be modulated with apoptosis such as CD95, ICAM-1, CD44, and carbohydrate determinants (Herbst, 1999, J. Cell Physiol. 181:295; Rapaport, 1999, Glycobiology 9:1337; Hirano (1999) Blood 93:2999; Thomas (1998) J. Immunol. 161:2195; Ma (1998) Eur. J. Hematol. 61:27; Pober (1998) Pathol. Biol. (Paris) 46:159).

Once a reference biomap for endothelial cell apoptosis is identified, compounds are screened for their ability to induce a similar biomap from tumor, but not normal, endothelial cells. Test patterns are compared to a database of reference biomaps that includes patterns obtained from the analysis of cells treated under environmental conditions in which single components are removed, or with known drugs that target specific pathways. Alternatively, reference biomaps are generated in the presence of genetic constructs that selectively target specific pathways. In this way, a database of reference biomaps is developed that can reveal the contributions of individual pathways to a complex response.

Angiogenesis Inhibitors

The present invention can be applied to the identification of compounds that inhibit or modulate angiogenesis. Pharmacologic modulation of angiogenesis has applications to the treatment of cancer, where vascularization of tumors contributes to cancer growth; for inflammatory conditions such as arthritis where neovascularization supports inflammatory cell influx; wound healing; and others. A number of biologically active agents are known to induce or promote angiogenesis including VEGF, FGF, IL-8, IL-4, various extracellular matrix components, etc., where at least 2, usually at least 3 of these factors may be used in an assay combination. Physiologically relevant states in vivo are complex, containing combinations of factors and other conditions. The environment of rheumatoid arthritis, in which angiogenic factors are present in a proinflammatory environment, can be distinguished from tumor environments that may be characterized by reduced oxygen and the presence of various growth factors in combination with a pro-angiogenic environment. Culture environments for endothelial cells that reflect these disease or physiological environments are developed through an iterative process of (a) identifying factors that are known to be expressed at the disease site. For example, vascularizing arthritis environments contain basic FGF and VEGF in addition to TNF-α, IL-1, IL-6, IL-10, IL-15, MIP1 and MCP-1 (Qu, 1995, Lab Invest., 73:339; Koch, J. Immunol. 1994, 152:4149; Robinson, 1995, Clin. Exp. Immunol. 101:398; Thurkow, 1997, J. Pathol. 181:444; Suzuki, 1999, Int. Immunol, 11:553). The disease environments of highly vascularized tumors includes hypoxia, VEGF, fibrinogen and TGF-β (Senger, 1994 Invasion Metastasis, 95:385; Shweiki, 1992, Nature, 359:843). The iterative process then (b) identifies a set of parameters that includes those that are known to be differentially regulated by one or more of the factors identified in (a), or parameters including adhesion molecules, receptors, chemokines, etc., that are known to be differentially expressed by angiogenic endothelium at the disease sites. These may include the expression of functional forms of adhesion molecules such as $\alpha_v\beta_3$, VCAM, proteases, such as matrix metalloproteinases, or other substances. The process then c) evaluates the effects of environments containing combinations of factors on the expression of parameters on endothelial cells in vitro; and d) selects conditions (factor composition, time course, concentration, etc.) that result in the pattern of expression of parameters that is representative of the in vivo phenotype. Optimization of the final set of environmental conditions and parameters is carried out by testing larger panels of parameters under the different environmental conditions in vitro and selecting those that can discriminate between two or more environments, said environments differing by one or more individual environmental components. This procedure can be performed in a high throughput manner, and individual selected parameters can be confirmed by evaluating the expression in vivo under normal and disease tissues. The goal of the above process is the identification and selection of a minimal set of parameters, each of which provides a robust readout, and that together enable discrimination of each environmental condition.

Once a panel of environments is identified, and an optimal set of parameters is selected, cells are treated under each condition and a database of reference biomaps is developed. These include reference biomaps from cells treated under environments that include known drugs that target specific pathways, as well as reference biomaps from the analysis of cells treated under environmental conditions in which single or multiple components are removed. For example, for an assay combination representing endothelial cells in a vascularizing arthritis environment, reference biomaps are developed from assay combinations in which single components (e.g. VEGF) might be removed. Reference biomaps are also generated from cells containing genetic constructs that selectively target specific pathways. In this way, a database of reference biomaps is developed that can reveal the contributions of individual pathways to a complex response.

With such a database, the invention provides for preferential selection of drug compounds that inhibit angiogenic responses in complex environments. Such compounds would be identified by their ability to induce a biomap consistent with inhibition of an angiogenic phenotype in the presence of a complex environment. Compounds that selectively block the response to a single factor or component of the complex environment (e.g. FGF receptor signaling, etc.) would be revealed by a biomap consistent with the response pattern in the absence of that factor (e.g. FGF, etc.)

The invention is also useful for screening compounds for drug interactions. Drug interactions can be problematic in cancer therapy. For example, while steroids control the edema that occurs with glioma, they also interfere with chemotherapy efficacy. Cytotoxic drugs form the basis of many cancer therapies, thus interference with chemotherapy efficacy may offset any anti-tumor effects of angiogenesis inhibitors. Most cytotoxic drugs effect both normal and neoplastic cells, although at different concentrations, therefore, screening compounds in the presence of cytotoxic drugs can be performed and reveal unexpected interference or beneficial synergies. Interactions between a cytotoxic drug and any test compound would be detected by the observation of biomaps obtained in the presence of both drugs that are inconsistent with additive effects.

Modulators of Bone Development

Modulation of bone development and remodeling has application for the therapy of osteoporosis, atherosclerosis, and rheumatoid arthritis, all situations where undesired bone destruction, bone formation or morphogenesis occurs. Bone-forming osteoblasts are derived from a common precursor in bone marrow that differentiates into osteoblasts or adipocytes depending on the differentiation environment. Factors associated with osteoblast development include estrogen, bone morphogenic proteins and TGF-β. Differentiation of osteoblasts is associated with the production of alkaline phosphatase, type I collagen, osteopontin and the ability to mineralize calcium. Factors associated with adipocyte development include FGF and glucocorticoids. Differentiation of adipocytes is associated with their production of PPARγ2, lipoprotein lipase and leptin. Optimized culture environments are defined for the relevant disease or physiologic states as described above and a set of parameters that distinguish adipocyte and osteoblast differentiation are selected. For screening compounds for inhibitors of osteoporosis, test compounds are screened for their ability to promote osteoblast development in the relevant disease environment. For example, in the case of older women, that would include low estrogen levels; in the case of autoimmune disease patients on long term glucocorticoid therapy, the environment may contain dexamethasone, and so on.

Modulation of osteoclast development and function has applications for bone remodeling that occurs in rheumatoid arthritis. Osteoclasts develop from CD14+ monocytes. Factors that promote osteoclast development include TRANCE (RANKL or osteoprotegrin ligand), TGFβ and M-CSF. Rheumatoid arthritis environments also contain TNF-α, IL-1, IL-6, IL-10, IL-15, MIP1 and MCP-1 (Robinson, 1995, Clin. Exp. Immunol. 101:398; Thurkow, 1997, J. Pathol. 181:444; Suzuki, 1999, Int. Immunol, 11:553). Optimized culture environments are defined for osteoclasts or precursor CD14+ monocytes in pro-osteoclast development arthritis environment. A set of parameters is selected that identifies osteoclasts in such an environment. Osteoclast function is associated with expression of calcitonin, vitronectin receptors, cathepsis k, carbonic anhydrase II, vacuolar (H(+)) ATPase, tartrate-resistant ATPase and osteopontin. For screening compounds to identify inhibitors of osteoclast development or function, active compounds are identified by their ability to inhibit osteoblast development in the relevant disease environment.

Neurobiology Applications

Alzheimer's Disease

A prominent feature of Alzheimer's disease patients is activated glia (astrocytes and microglia) in close proximity to amyloid plaques. These cells express increased levels of Class II antigens, alpha-1-antichymotrypsin, IL-1β, S-100β and butyrylcholinesterase. The disease environment in Alzheimer's disease contains IL-1, IL-6 and the β-amyloid peptide 1–42.

Regulators of Hematopoiesis

Mesenchymyl stem cell cultures can be provided with environments leading to fibroblastic, osteoblastic, or adipocyte differentiation, each associated with unique patterns of cell surface and secreted molecule expression defining these cellular states. A set of parameters that identifies various lineages of hematopoietic cells (e.g. erythroid, myeloid, T versus B, NK, etc.) are selected. Compounds that alter the differentiation of selected cell types are selected by their ability to produce biomaps characteristic of that population.

Kits

For convenience, the systems of the subject invention may be provided in kits. The kits could include the appropriate additives for providing the simulation, optionally include the cells to be used, which may be frozen, refrigerated or treated in some other manner to maintain viability, reagents for measuring the parameters, and software for preparing the biomap. The factors will be selected that in conjunction with the cells would provide the desired physiological state simulating the in vivo situation. The factors could be a mixture in the appropriate proportions or provided individually. For example, IL-1, TNF-α, and IFN-γ would be combined as a powder to be measured for addition to the cell medium and labeled antibodies to parameters, such as ICAM-1, VCAM-1 and E-selectin, in conjunction with second capture antibodies or using antibodies for homogeneous assays, where another reagent is present. The software will receive the results and create a biomap and can include data from other assay combinations for comparison. The software can also normalize the results with the results from a basal culture and/or the basal culture including the factors.

EXPERIMENTAL

Example 1

Regulators of Endothelial Cell Responses to Inflammation

The present invention is useful for identifying regulators of inflammation using human endothelial cells as an indicator cell type. A set of assay combinations that reproduces aspects of the response of the endothelial cells to different types of inflammatory processes is developed in vitro.

Primary human umbilical vein endothelial cells (HUVEC) are used. Other cells that may replace HUVEC in the screen include primary microvascular endothelial cells, aortic or arteriolar endothelial cells or endothelial cell lines such as EAhy926 or E6-E74-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999). $2 \times 10^4$ cells/ml are cultured to confluence in EGM-2 (Clonetics). Other media that may replace EGM-2 include EGM (Clonetics) and Ham's F12K medium supplemented with 0.1 mg/ml heparin and 0.03–0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984). The disease environment present in chronic inflammatory diseases, such as Crohn's disease, differs from the normal condition by increased presence of multiple biologically active agents including IL-1, TNF-α, and IFN-γ (Woywodt, 1994; Kakazu, 1999). Other biologically active agents that may be increased in chronic inflammatory disease environments include IL-4, IL-6, IL-8, IL-12, IL-13, IL-18, TGFbeta, and histamine, as well as activated leukocytes and their products (Daig, 1996, Gut 38:216; Woywodt, 1994, Eur. cytokine Netw. 5:387; Kakazu, 1999 Am J. Gastroenterol. 94:2149; Pizarro, 1999, J. Immunol. 162:6829; Monteleone, 1999, J. Immunol. 163:143; McClane, 1999 J Parenter Enteral Nutr 23:S20; Beck, 1999, Inflam. Bowel Dis. 5:44). Optimized assay combinations will contain at least two, and preferably three, four or more of these biologically active agents.

Concentrations of agents are standard according to the literature, typically at physiologic concentrations. Concentrations may also be determined experimentally as the amount required to saturate the relevant receptor. A useful feature of the present invention is that combinatorial effects of multiple factors are observed over wide ranges of factor concentrations. Based on the factors included in an assay combination, a set of parameters for including in a biomap are selected.

Selection of parameters is based on the following factors: 1) parameters that are modulated in vivo in the disease environment or condition; 2) parameters that are modulated by one of the components in the assay combination; 3) parameters that are modulated by more than one of the components in the assay combination; 4) parameters that are modulated by the combined action of two or more components in the assay combination; 5) parameters that participate in the disease process, such as validated disease targets; 6) cell surface and secreted molecules. Preferred parameters are functional and are downstream within signaling pathways, so as to provide information on effects of multiple pathways.

For assay combinations containing the factors TNFα, IFN-γ and IL-1, parameters examined and chosen by these criteria include ICAM-1 (CD54), VCAM-1 (CD106), E-selectin (CD62E), IL-8, HLA-DR and MIG (CLCX9). Other parameters of interest for including in a Biomap include: IP-10, Eotaxin-1, Eotaxin-3, MCP-1, RANTES, Tarc, CD31, alphavbeta3, and P-selectin (CD62P). Parameters examined but not selected include: CD34, CD40, CD9, CXCR2, CD95, fibronectin, HLA-ABC, GROalpha, MCP-4, TAPA-1, alphaVbeta5, VE-Cadherin, CD44, von Willebrand factor, CD141, 142, 143, and CD151.

Parameters are not selected for inclusion in a biomap for the following reasons: redundancy, function of parameter is not associated with disease pathology, function is upstream in a signaling pathway, parameter is not modulated in response to factors, modulation is not robust or reproducible. Cell death in inflammation, involved for example in cellular remodeling in healing, as well as the consequences of toxicity, involves apoptosis.

Parameters of interest also include parameters indicative of cell damage and apoptosis including released cytoplasmic lactate dehydrogenase (LDH) or mitochondrial cytochrome c, appearance of APO2.7 epitope or active caspase-3 (Zhang, J. Immunol., 157:3980, 1996; Bussing, Cytometry 37:133, 1999).

Parameters indicative of cell proliferation are also of interest and include Ki-67 and PCNA (Landberg, Cytometry, 13:230, 1992). Strategies for optimizing the parameter set include: selecting only one of any group of parameters that are co-regulated under all assay combinations; preferentially selecting parameters that are functionally relevant to the disease process; preferentially selecting parameters that give robust and reproducible results in multiple assays, or reflect cellular toxicity etc.

In the present example, whereas both IP-10 and MIG are co-regulated under the assay conditions described, detection of MIG by the cell-based ELISA as described above is more robust, therefore MIG was preferentially included in the optimized set of parameters.

For parameter set optimization, additional parameters may be added to the initial parameter set to distinguish assay combinations that result in cellular de-adhesion, toxicity or other activity. Microscopic observation can identify cellular de-adhesion, while release of cytoplasmic substances, such as lactate dehydrogenase, can be measured as an indication of toxicity. For example, CD31 is an endothelial cell adhesion molecule that participates in cell—cell adhesion and complete loss of CD31 expression in an assay indicates loss of cells from the plate. Therefore, CD31 is a useful parameter for monitoring cellular de-adhesion. The experiments provided in FIGS. 1A–1C illustrate the usefulness of the present invention in compound screening applications.

FIG. 1A shows the readout patterns from confluent cultures of HUVEC incubated with either of TNF-α (5 ng/ml), IFN-γ (100 ng/ml) or IL-1 (1 ng/ml) or basal medium for 24 hours. After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA as described (Melrose, J. Immunol. 161:2457, 1998). For this, plates are blocked with 1% Blotto for 1 hr, and treated with primary antibodies (obtained from Pharmingen and Becton Dickinson) at 1 ng/ml for 2 hr. After washing, secondary peroxidase-conjugated anti-mouse IgG antibody (Promega) at 1:2500 is applied for 45 min. After washing, TMB substrate (Kierkegaard & Perry) is added and color developed. Development is stopped by addition of $H_2SO_4$ and the absorbance at 450 nm (subtracting the background absorbance at 600 nm) is read with a Molecular Dynamics plate reader. The relative expression levels of each parameter are indicated by the OD at 450 nm shown along the y-axis. The mean +/− SD from triplicate samples is shown.

Figure 1B:
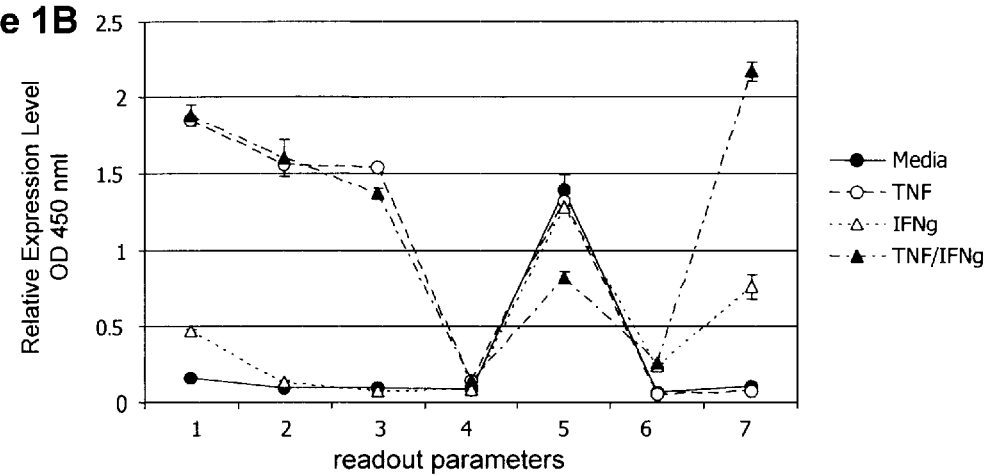
Figure 1C:
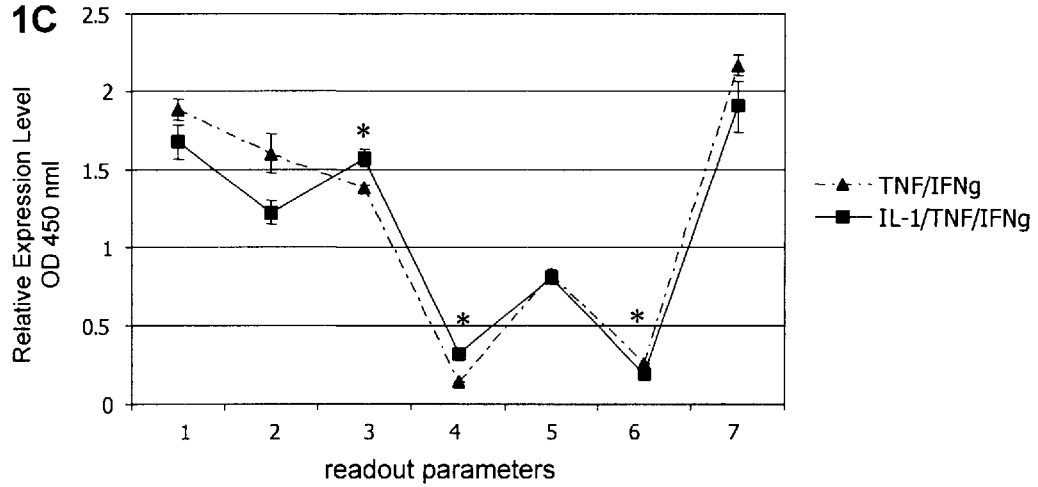

The assay combinations shown in FIG. 1 are useful in screening compounds that modulate TNF-α, IL-1 and IFN-γ signaling pathways, however, compounds must be evaluated separately in all three assay combinations to identify compounds that selectively modulate one or more of these pathways. In addition, compounds that selectively modulate combinatorial effects of these pathways cannot be distinguished. An assay combination with improved usefulness is described in FIG. 1B. FIG. 1B shows the readout patterns from confluent cultures of HUVEC cells treated with TNF-α (5 ng/ml), IFN-γ (100 ng/ml), TNF-α (5 ng/ml)+IFN-γ (100 ng/ml) or base media. After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA performed as described in FIG. 1 and are reported as the OD at 450 nm in FIG. 2. The mean +/− SD from triplicate samples are shown. * indicates p<0.05 comparing results obtained with the two separate conditions.

As shown in FIG. 2, HUVEC cultured with TNF-α for 24 hours express increased levels of cell surface ICAM-1, VCAM-1, and E-selectin as measured by cell-based ELISA. HUVEC cultured with IFN-γ for 24 hours express increased levels of ICAM-1, HLA-DR and MIG. HUVEC cultured in the presence of both TNF-α and IFN-γ for 24 hours produce a combined phenotype where HUVEC express increased levels of ICAM-1, VCAM-1, E-selectin, HLA-DR and MIG. This phenotype is more similar to the in vivo phenotype of endothelial cells in chronic inflammation and moreover reflects the stimulation of two different known pathways of interest in regulation of inflammatory processes. Concentrations of TNF-α and IFN-γ employed and length of exposure are standard according to the literature. Concentrations and exposure length are also tested experimentally and conditions chosen to achieve an endothelial cell phenotype displaying multiple features of endothelial cells in chronic inflammatory diseases (e.g increased expression of ICAM-1, VCAM-1, E-selectin as well as HLA-DR and MIG). However, a particularly useful feature of the invention is that the combined phenotype is observed over a wide range of concentrations of the individual biologically active factors. The results in FIG. 1B demonstrate how an assay combination containing both TNF-α and IFN-γ is useful in screening for compounds that block either the TNF-α or IFN-γ signaling pathways, and furthermore, can be used to distinguish compounds that modulate combinatorial effects of these pathways.

Inclusion of additional biologically active factors further improves the usefulness of the screens provided in the present invention. FIG. 1C shows the readout patterns from confluent cultures of HUVEC cells treated with TNF-α (5 ng/ml)+IFN-γ (100 ng/ml) or TNF-α (5 ng/ml)+IFN-γ (100 ng/ml)+IL-1 (1 ng/ml). After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA performed as described in FIG. 1 and are reported as the OD at 450 nm. The mean +/− SD from triplicate samples are shown. * indicates p<0.05 comparing results obtained with the two separate conditions. Addition of IL-1 to the assay combination containing TNF-α and IFN-γ results in increased levels of E-selectin and IL-8 (shown in FIG. 1B), in addition to the increased levels of ICAM-1, VCAM-1, HLA-DR and MIG. E-selectin and IL-8 are particularly correlated with disease stage in chronic inflammatory diseases, including inflammatory bowel disease (MacDermott, 1999, J. Clin. Immunol. 19:266; Koizumi, 1992, Gastroenterology 1992103:840). Thus an assay combination containing IL-1, TNF-α and IFN-γ represents an optimized assay combination. This assay combination is useful for screening for compounds that modulate aspects of IL-1, TNF-α or IFN-γ signaling pathways. In particular, it provides a useful screen for selecting compounds that are active when a particular target pathway may be modified by the activity of other pathways or when the target is not known. In subsequent panels one or more of IL-4, IL-6, IL-8, IL-12, IL-13, IL-18, TGFbeta, and histamine are applied; and/or neutralizing antibodies to autocrine factors such as IL-6, IL-1 and IL-8. Standard concentrations of agents are employed as described in the literature. Based on the factors selected, a set of parameters for including in a biomap is selected.

Database of readout response patterns. A database of reference biomaps is compiled for the optimized assay combination and parameter set of the example described in FIG. 1C. These reference biomaps are developed from assay combinations in which specific modifications of the optimized assay combination are made. These modifications included: 1) elimination of one or more assay combination components, 2) addition of compounds or interventions to the assay combination. Biological responses, particularly responses in primary human cells can display significant variability from day to day and from donor to donor. One important aspect of the present invention is that while absolute amounts of parameters can vary substantially between assays, combinatorial responses provide for less variability and the process of normalization to produce a biomap provides cellular activity profiles that are robust and reproducible.

Figure 2A:
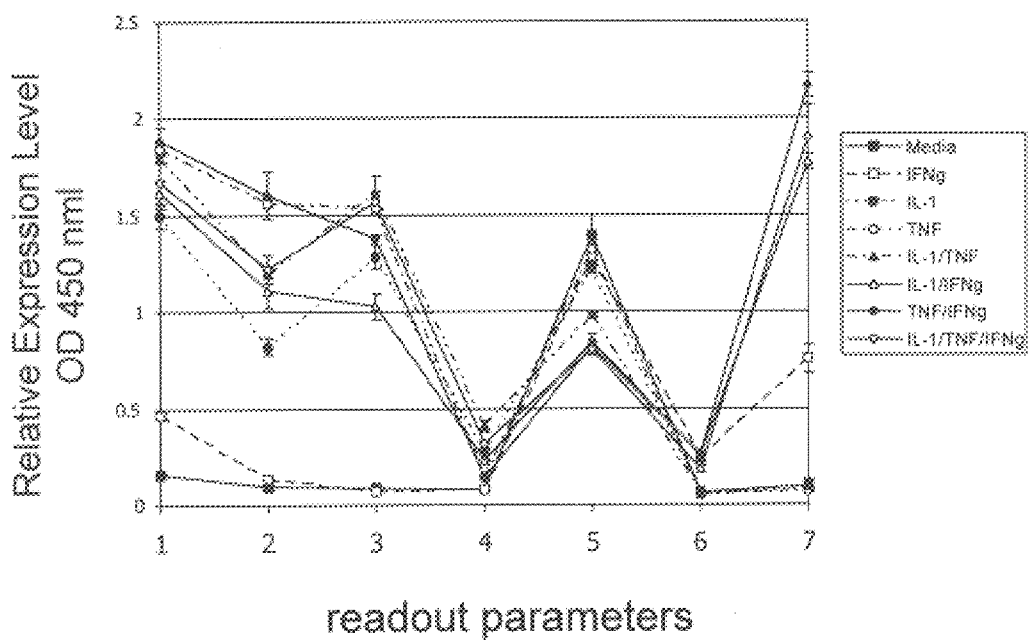
FIG. 2. Assay combinations for screening inflammatory modulators. Confluent cultures of HUVEC cells were treated with combinations of TNF-$\alpha$ (5 ng/ml), IFN-$\gamma$ (200 ng/ml) and IL-1 (1 ng/ml) or base media. After 24 hours, cultures were washed and evaluated for the presence of ICAM-1 (1), VCAM-1 (2), E-selectin (3), IL-8 (4), CD31 (5), HLA-DR (6) and MIG (7) by cell-based ELISA performed as described in FIG. 1. A. The relative expression level of each parameter is shown along the y-axis as average value of the OD measured at 450 nm of triplicate samples. B. A color-coded representation of the data shown in A. For each parameter and assay combination, the square is colored light gray if the parameter measurement is unchanged (<20% above or below the measurement in the first assay combination (IL-1+TNF+IFN-$\gamma$) or p>0.05, n=3); white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination). C. A tree diagram representation of the biomaps prepared from data shown in A and B. Resulting biomaps were compared and analyzed by hierarchical clustering. Biomap relationships are visualized by a tree diagram in which a) each terminal branch point represents the biomap prepared from the indicated assay combination; b) the length of the vertical distance from the upper horizontal line (no change and control patterns) to the termini are related to the extent of difference in the readout pattern from the reference pattern (IL-1+TNF-α+IFN-γ); and c) the distance along the branches from one terminal pattern value to another reflects the extent of difference between them.
Figure 2B:
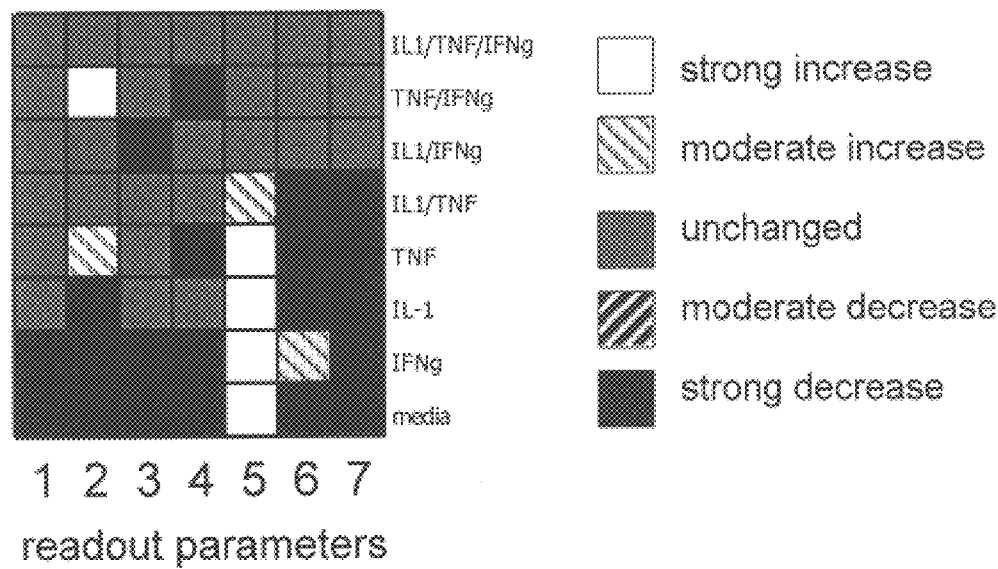

FIG. 2A shows a set of reference biomaps developed from assay combinations in which one or more of the cytokines, IL1, TNF-α or IFN-γ is eliminated. For each reference assay combination, the selected parameters are measured and the resulting biomaps developed from the data are compared. FIG. 2A shows how measuring the levels of the parameters ICAM-1 (1), VCAM-1 (2), E-selectin (3), IL-8 (4), CD31 (5), HLA-DR (6), and MIG (7), by cell-based ELISA under each of these assay combinations, results in different reference biomaps for each assay combination. The set of parameter measurements under each of these conditions comprises a reference biomap to which test patterns can be compared. FIG. 2B shows a visual representation of this data, where the measurement obtained for each parameter is classified according to its relative change from the value obtained in the optimized assay combination (containing IL-1+TNF-α +IFN-γ), and represented by shaded squares. For each parameter and assay combination, the square is colored light gray if the parameter measurement is unchanged (<20% above or below the measurement in the first assay combination (IL-1+TNF-α+IFN-γ)) or p>0.05, n=3; white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

Figure 2C:
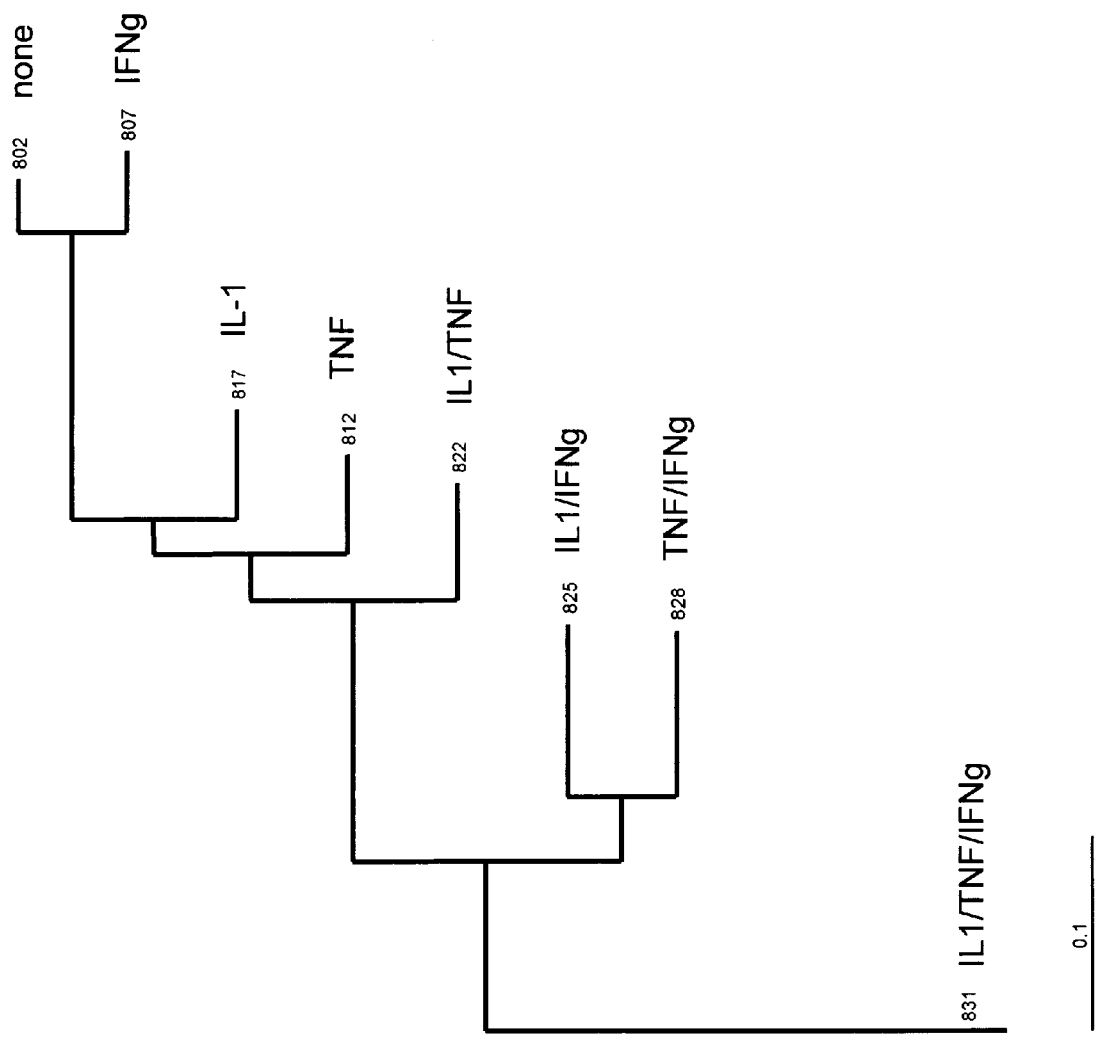

FIG. 2C shows an alternative visual representation of the set of reference biomaps whereby individual parameter readouts are compared by hierarchical cluster analysis. For this, regression analysis is performed on reference biomaps and correlation coefficients are used in cluster analysis. The clustering relationships can be represented visually, for example, as a tree in which related biomaps are on common branches, and the distance between patterns on the tree reflects the extent of differences in the biomaps. FIG. 2C shows how the biomaps derived from assay combinations containing TNF-α and/or IL1 are easily distinguished from those derived from assay combinations containing IFN-γ or the combination of IFN-γ and TNF-α and/or IL-1. Applying weighting factors to individual parameter readouts allows the biomap analysis to sufficiently distinguish particular signaling pathways of interest. A significant aspect of the invention is the selection of a set of parameters and assay combinations that can optimally distinguish multiple pathways of interest. Active compounds are chosen on the basis of their ability to alter the resulting biomap when included in a selected assay combination. Such alteration may include returning the levels of one or more parameters to their levels in the basal condition, or otherwise altering the cellular responses, particularly when such alterations reflect changes towards a desirable cellular state.

Figure 3A:
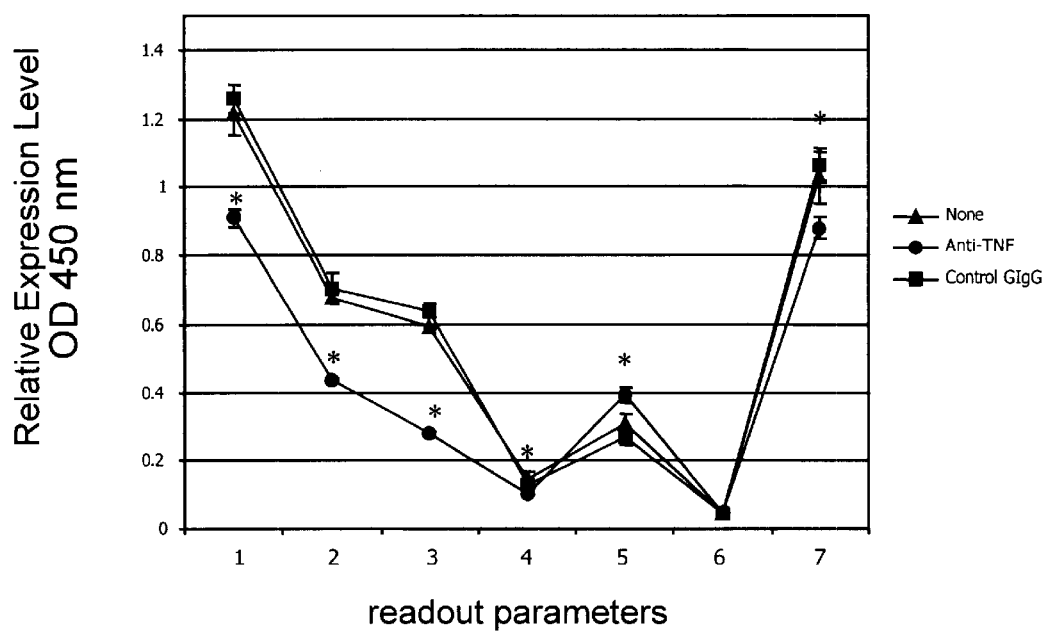
FIG. 3. Effect of neutralizing anti-TNF-α antibody on the expression of readout parameters in the inflammatory assay combination containing three factors (IL-1+TNF-α+IFN-γ). Confluent cultures of HUVEC cells were treated with TNF-α (5 ng/ml)+IFN-γ (200 ng/ml)+IL-1 (1 ng/ml) in the presence or absence of neutralizing anti-TNF-α (R&D Systems) or control Goat anti-IgG. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A. The relative expression of each parameter is shown along the y-axis as average value of the OD measured at 450 nm of triplicate samples. The mean +/− SD from triplicate samples are shown. * indicates $p<0.05$ comparing results obtained with anti-TNF-α to the control. B. A color-coded representation of biomaps prepared from the data shown in A. For each parameter and assay combination, the square is colored light gray if the parameter measurement is unchanged (<20% above or below the measurement in the first assay combination (IL-1+TNF-α+IFN-γ) or $p>0.05$, n=3); white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

An inhibitor of TNF-α is an active compound in the optimized assay combination described above. Addition of neutralizing anti-TNF-α antibodies to this assay combination results in reduced expression levels of ICAM-1, VCAM-1, E-selectin, IL-8, and MIG, and increased expression levels of CD31 (FIG. 3A). Confluent cultures of HUVEC cells are treated with TNF-α (5 ng/ml)+IFN-γ (100 ng/ml)+IL-1 (1 ng/ml) in the presence or absence of neutralizing anti-TNF-α or control antibody (Goat anti-IgG). After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. In FIG. 3A, the relative expression of each parameter is shown along the y-axis as average value of the OD measured at 450 nm of triplicate samples. The mean +/− SD from triplicate samples are shown. * indicates p<0.05 comparing results obtained with anti-TNF-α to the control.

Figure 3B:
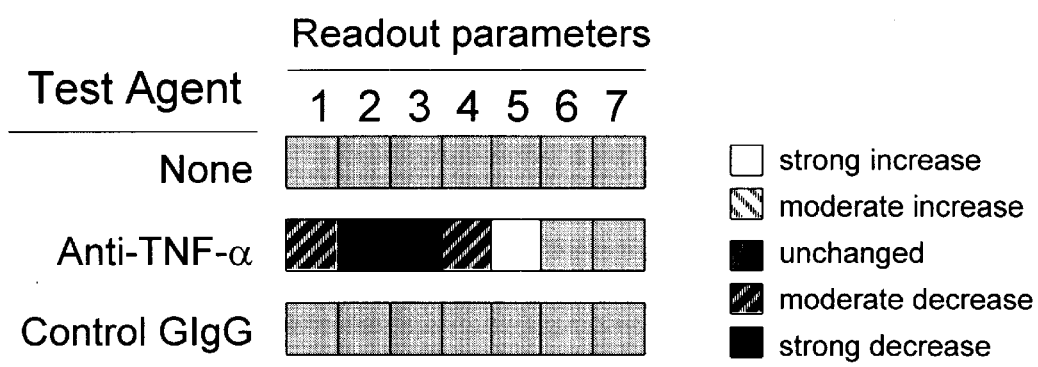

FIG. 3B, is a color-coded representation of the biomaps developed from the data shown in A. For each parameter and assay combination, the square is colored light gray if the parameter measurement is unchanged (<20% above or below the measurement in the first assay combination (IL-1+TNF-α+IFN-γ)) or p>0.05, n=3; white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

Figure 4A:
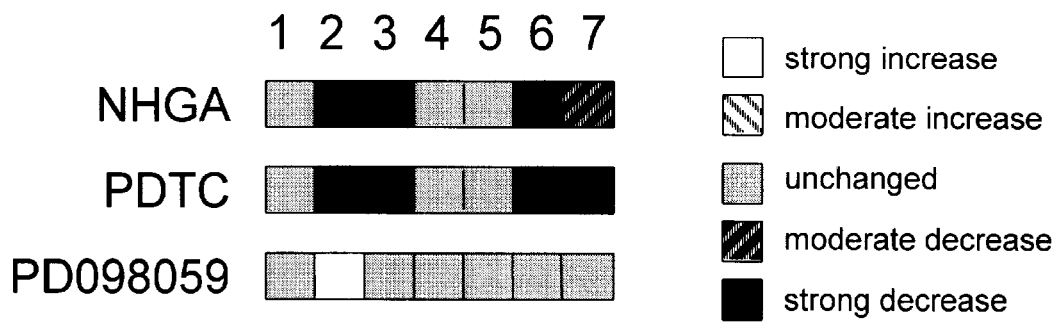
FIG. 4. A and B. Effect of NFκB inhibitors nordihydroguaiaretic acid (NHGA) and pyrrolidine dithiocarbamate (PDTC), MAP kinase inhibitor PD098059, or ibuprofen on the expression of readout parameters in the inflammatory assay combination containing three factors (IL-1+TNF-α+IFN-γ). Confluent cultures of HUVEC cells were treated with TNF-α (5 ng/ml)+IFN-γ (200 ng/ml)+IL-1 (20 ng/ml) in the presence or absence of (A) 10 μM NHGA, 200 μM PDTC or 9 μM PD098059; (B) 125–500 μM ibuprofen. Compounds were tested at the highest concentration at which they were soluble, and/or did not result in loss of cells from the plate. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A color-coded representation of the biomaps prepared from the data is shown. For each parameter and assay combination, the square is colored light gray if the parameter measurement is unchanged (<20% above or below the measurement in the first assay combination (IL-1+TNF-α+IFN-γ), or $p>0.05$, n=3); white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).
FIG. 4C. Effect of compounds on the reference readout pattern in the inflammatory assay combination containing three factors (IL-1+TNF-α+IFN-γ). Confluent cultures of HUVEC cells were treated with TNF-α (5 ng/ml)+IFN-γ (200 ng/ml)+IL-1 (1 ng/ml) in the presence or absence of compounds or agents as listed in Table 1. After 24 hours, cultures were washed and evaluated for the cell surface expression of parameters of ICAM-1, VCAM-1, E-selectin, IL-8, CD31, HLA-DR and MIG by cell-based ELISA performed as described in FIG. 1. The resulting biomaps were compared (Table 1) and analyzed by hierarchical clustering. Biomap relationships are visualized by a tree diagram in which a) each terminal branch point represents the biomap prepared from the indicated assay combination; b) the length of the vertical distance from the upper horizontal line (no change and control patterns) to the termini are related to the extent of difference in the readout pattern from the reference pattern (IL-1+TNF-α+IFN-γ); and c) the distance along the branches from one terminal pattern value to another reflects the extent of difference between them. Similar patterns are thus clustered together. The figure illustrates the reproducibility of patterns resulting from treatment with a single drug in multiple experiments, and those resulting from multiple drugs that target the same signaling pathway.

Inhibitors of NFκB, MAP kinases and non-steroidal anti-inflammatory drugs are active compounds in the optimized assay combination described above. FIG. 4A shows results of assaying confluent cultures of HUVEC cells treated with TNF-α (5 ng/ml)+IFN-γ (100 ng/ml)+IL-1 (1 ng/ml) in the presence or absence of (A) 10 µM NHGA, 200 µM PDTC or 9 µM PD098059 or (B) 125–500 µM ibuprofen. Compounds are tested at the highest concentration at which they are soluble, and do not result in cellular toxicity or loss of cells from the plate. After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A color-coded representation of the biomaps developed from the data is shown. For each parameter and assay combination, the square is colored light gray if the parameter measurement is unchanged (<20% above or below the measurement in the first assay combination (IL-1+TNF-α+IFN-γ)) or p>0.05, n=3; white/gray hatched indicates that the parameter measurement is moderately increased (>20% but <50%); white indicates the parameter measurement is strongly increased (>50%); black/gray hatched indicates that the parameter measurement is moderately decreased (>20% but <50%); black indicates that the parameter measurement is strongly decreased (>50% less than the level measured in the first assay combination). In the present example, FIG. 4A shows how addition of the NFκB inhibitors nordihydroguaiaretic acid (NHGA) (Brennen, Biochem. Pharmacol., 55:965, 1998) or pyrrolidine dithiocarbamate (PDTC) (Boyle, Circulation, 98, (19 Suppl):11282, 1998) to the optimized assay combination results in altered biomaps that are distinct from the altered biomaps obtained with the p42/44 MAP kinase inhibitor, PD098059 (Milanini, J. Biol. Chem. 273:18165, 1998). Active compounds that act with a similar mechanism of action as NHGA and PDTC will give a biomap that can be distinguished from active compounds that act with a similar mechanism of action as PD098059.

Figure 4B:
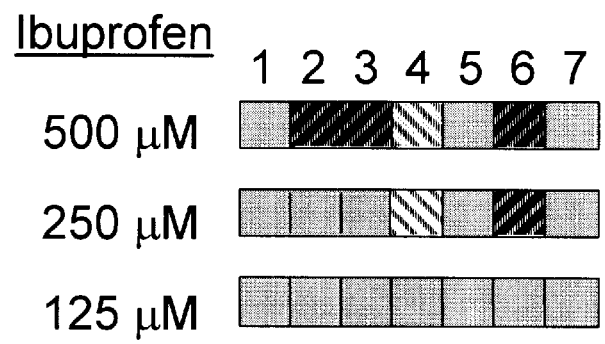

Obtaining biomaps from drug compounds tested at different concentrations also expands the usefulness of the database. In the present example, ibuprofen gives visually similar biomaps when tested at 500, 250 and 125 µM, as shown in FIG. 4B, although regression analysis indicates they are highly related (correlation coefficients derived from the primary data range between 0.96–0.99). Reference biomaps from assay combinations that include known drug compounds, agents, or with other specific modifications are developed for inclusion in a database. Biomaps from these assay combinations are developed so as to expand the usefulness of the database.

Table 1 shows a list of agents or specific modifications evaluated, including N-acetylcysteine (Faruqui, Am. J. Physiol. 273(2 Pt 2):H817, 1997), the corticosteroids dexamethasone and prednisolone, echinacea, AA861 (Lee, J. Immunol. 158, 3401, 1997), apigenin (Gerritsen, Am. J. Pathol. 147:278, 1995), nordihydroguaiaretic acid (NHGA) (Brennen, Biochem. Pharmacol., 55:965, 1998), phenylarsine oxide (PAO) (Dhawan, Eur. J. Immunol. 27:2172, 1997), pyrrolidine dithiocarbamate (PDTC) (Boyle, Circulation, 98, (19 Suppl):11282, 1998), PPM-18 (Yu, Biochem. J., 328:363, 1997), the non-steroidal anti-inflammatory drug (NSAID) buprofen, SB 203580, PD098059 (Milanini, J. Biol. Chem. 273:18165, 1998), AG126 (Novogrodsky, Science 264, 1319, 1994), and neutralizing anti-TNF-α antibody. Color-coded representations of the resulting biomaps are shown. Confluent cultures of HUVEC cells are treated with TNF-α (5 ng/ml)+IFN-γ (100 ng/ml)+IL-1 (1 ng/ml) in the presence or absence of agents or buffers at the concentrations indicated in Table 1. Compounds are obtained from commercial sources and prepared in a suitable buffer (water, base media, DMSO, methanol or ethanol). After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A color-coded representation of the resulting biomaps developed from the data is shown. For each parameter and assay combination, the square is colored light gray if the parameter measurement is unchanged (<20% above or below the measurement in the control assay combination (IL-1+TNF-α +IFN-y)) or p>0.05, n=3; white/gray hatched indicates that the parameter measurement is moderately increased (>20% but <50%); white indicates the parameter measurement is strongly increased (>50%); black/gray hatched indicates that the parameter measurement is moderately decreased (>20% but <50%); black indicates that the parameter measurement is strongly decreased (>50% less than the level measured in the first. Control assay combinations for each agent include an appropriate concentration of the diluent buffer.

TABLE 1

Reference biomaps.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| Antioxidant | 181 | N-acetylcysteine | 5.00 | µM | | | | | | | ■ |
| Antioxidant | 182 | N-acetylcysteine | 2.50 | µM | | | | | | | ■ |
| Antioxidant | 183 | N-acetylcysteine | 1.25 | µM | | | | | | | |
| Antioxidant | 184 | N-acetylcysteine | 1.25 | µM | | | | | | | |
| Corticosteroid | 717 | Dexamethazone | 12.50 | µM | | | | | | | |
| Corticosteroid | 716 | Dexamethazone | 6.25 | µM | | | | | | | |
| Corticosteroid | 715 | Dexamethazone | 3.10 | µM | | | | | | | |
| Corticosteroid | 301 | Dexamethazone | 2.00 | µM | | | | | | | |
| Corticosteroid | 302 | Dexamethazone | 1.00 | µM | | | | | | | |
| Corticosteroid | 303 | Dexamethazone | 0.50 | µM | | | | | | | |
| Corticosteroid | 241 | Prednisolone | 160.00 | µM | | | | | | | |
| Corticosteroid | 242 | Prednisolone | 160.00 | µM | | | | | | | |
| Corticosteroid | 243 | Prednisolone | 80.00 | µM | | | | | | | |
| Corticosteroid | 244 | Prednisolone | 40.00 | µM | | | | | | | |
| Natural Product | 91 | Echinacea | 2.27 | % | | | | | | | ■ |
| Natural Product | 94 | Echinacea | 2.27 | % | | ■ | | | | | |
| Natural Product | 92 | Echinacea | 1.13 | % | | | | | | | |
| Natural Product | 93 | Echinacea | 0.57 | % | | | | | | | |
| NFκB | 4 | AA861 | 20.00 | µM | | ■ | ■ | | ND | ■ | |
| NFκB | 5 | AA861 | 20.00 | µM | | | ■ | | ND | ND | |
| NFκB | 6 | AA861 | 20.00 | µM | | | | ■ | | ■ | ■ |
| NFκB | 701 | AA861 | 20.00 | µM | | ■ | ■ | | | ND | |
| NFκB | 19 | Apigenen | 8.10 | µM | | | ■ | | | ■ | |

TABLE 1-continued

Reference biomaps.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| NFκB | 20 | Apigenen | 6.00 | μM | | ■ | ■ | | | ■ | |
| NFκB | 21 | Apigenen | 5.00 | μM | | | | | | | |
| NFκB | 202 | Nordihydroguaiaretic acid (NHGA) | 10.00 | μM | | ■ | ■ | | ND | | |
| NFκB | 203 | Nordihydroguaiaretic acid (NHGA) | 10.00 | μM | | ■ | | | ND | ND | |
| NFκB | 204 | Nordihydroguaiaretic acid (NHGA) | 10.00 | μM | | ■ | ■ | | | ■ | |
| NFκB | 719 | Nordihydroguaiaretic acid (NHGA) | 6.00 | μM | | ■ | ■ | | | ■ | |
| NFκB | 205 | Nordihydroguaiaretic acid (NHGA) | 5.00 | μM | | | | | | | |
| NFκB | 718 | Nordihydroguaiaretic acid (NHGA) | 0.63 | μM | | ■ | ■ | | | | ■ |
| NFκB | 720 | PAO | 50.00 | μM | | ■ | ■ | | | ■ | |
| NFκB | 231 | PDTC | 200.00 | μM | ■ | ■ | ■ | ■ | | ■ | ■ |
| NFκB | 233 | PDTC | 200.00 | μM | | ■ | ■ | | | ■ | ■ |
| NFκB | 234 | PDTC | 200.00 | μM | | ■ | ■ | | | ■ | |
| NFκB | 725 | PDTC | 100.00 | μM | ■ | ■ | ■ | | | ND | ■ |
| NFκB | 726 | PDTC | 100.00 | μM | | ■ | ■ | | | | ■ |
| NFκB | 235 | PDTC | 100.00 | μM | | | ■ | | | ■ | ■ |
| NFκB | 232 | PDTC | 50.00 | μM | | ■ | ■ | | ND | ■ | |
| NFκB | 724 | PDTC | 50.00 | μM | | ■ | ■ | ND | ND | ND | ■ |
| NFκB | 236 | PDTC | 50.00 | μM | | | | ■ | | | |
| NFκB | 728 | PPM-18 | 2.50 | μM | | ■ | ■ | | | | ■ |
| NFκB | 727 | PPM-18 | 2.00 | μM | | ■ | ■ | | | | ■ |
| NFκB | 735 | PPM-1B | 2.00 | μM | | ■ | | | | | |
| NSAID | 131 | Ibuprofen | 500.00 | μM | | | | | | | |
| NSAID | 132 | Ibuprofen | 500.00 | μM | | | ■ | | | | |
| p38 MAPK | 730 | SB 203580 | 80.00 | μM | | ■ | | ■ | | ND | ■ |
| p38 MAPK | 729 | SB 203580 | 40.00 | μM | | | | | | ND | |

TABLE 1-continued

Reference biomaps.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| p42/44 MAPK | 221 | PD098059 | 18.70 | µM | | | | ■ | ND | ND | |
| p42/44 MAPK | 222 | PD098059 | 9.30 | µM | | | | ▓ | ND | ND | |
| p42/44 MAPK | 223 | PD098059 | 9.30 | µM | | | | | ND | ■ | |
| p42/44 MAPK | 224 | PD098059 | 9.00 | µM | | | | | | ▓ | |
| p42/44 MAPK | 723 | PD098059 | 9.00 | µM | | | | ▓ | | ND | |
| p42/44 MAPK | 225 | PD098059 | 4.60 | µM | | | | ▓ | | ND | |
| p42/44 MAPK | 722 | PD098059 | 2.25 | µM | | | | | | ND | |
| p42/44 MAPK | 721 | PD098059 | 0.56 | µM | | | | | | ND | |
| Tyr Kinase | 733 | AG126 | 25.00 | µM | | ■ | | | | | |
| Tyr Kinase | 702 | AG126 | 25.00 | µM | | ■ | ■ | | | | |
| Tyr Kinase | 734 | AG126 | 25.00 | µM | | ■ | | | | | |
| Antibody | 712 | Anti-TNF | 5.00 | µg/ml | | ■ | ■ | ▓ | ND | ND | ▓ |
| Antibody | 713 | Anti-TNF | 5.00 | µg/ml | ▓ | ■ | ■ | ▓ | | ND | |
| Antibody | 711 | Anti-TNF | 4.00 | µg/ml | | ▓ | ■ | ▓ | ND | ND | |
| Antibody | 710 | Anti-TNF | 1.67 | µg/ml | | ■ | ■ | | ND | ND | ▓ |
| Antibody | 709 | Anti-TNF | 0.55 | µg/ml | | | | | ND | ND | |
| Antibody | 708 | Anti-TNF | 0.40 | µg/ml | | | | | ND | ND | |
| Antibody | 707 | Anti-TNF | 0.04 | µg/ml | | | | | ND | ND | |
| Antibody | 714 | Anti-TNF-R (Act) | 5.00 | µg/ml | | | | | ND | ND | |
| N/A | 520 | Control | | | | | | | | | |
| N/A | 521 | Control | | | | | | | | | |
| N/A | 522 | Control | | | | | | | | | |
| N/A | 523 | Control | | | | | | | | | |
| N/A | 524 | Control | | | | | | | | ND | |
| N/A | 525 | No IL1 | | | | | ■ | | | | |

TABLE 1-continued

Reference biomaps.

| Inhibitor Class | UID | Compound | Conc. | Units | Readout Parameters ||||||| 
|---|---|---|---|---|---|---|---|---|---|---|---|
| | | | | | 1 | 2 | 3 | 4 | 5 | 6 | 7 |
| N/A | 526 | No IL1 | | | ░ | | ░ | ■ | ░ | | ░ |
| N/A | 527 | No IL1 | | | ░ | | ░ | ■ | ND | | ░ |
| N/A | 531 | No TNF | | | ░ | ▒ | ■ | ░ | ░ | ░ | ▒ |
| N/A | 532 | No TNF | | | ░ | ▒ | ■ | ▒ | ░ | | ░ |
| N/A | 533 | No TNF | | | ░ | ■ | ■ | ░ | ND | ░ | ░ |
| N/A | 515 | NoIL1IFNg | | | ░ | | ▒ | ░ | ░ | ░ | ■ |
| N/A | 516 | NoIL1IFNg | | | ░ | ░ | ■ | ▒ | | ■ | ■ |
| N/A | 517 | NoIL1IFNg | | | ░ | | ■ | ▒ | | ■ | ■ |
| N/A | 518 | NoIL1IFNg | | | ░ | | ░ | | | ■ | ■ |
| N/A | 519 | NoIL1IFNg | | | ░ | | ▒ | | ND | ■ | ■ |
| N/A | 510 | NoTNFIFNg | | | ░ | ■ | ■ | ░ | ░ | ░ | ■ |
| N/A | 511 | NoTNFIFNg | | | ░ | ■ | ■ | ░ | | ■ | ■ |
| N/A | 512 | NoTNFIFNg | | | ░ | ■ | ■ | ░ | | ■ | ■ |
| N/A | 513 | NoTNFIFNg | | | ░ | ■ | ░ | ░ | | ■ | ■ |
| N/A | 514 | NoTNFIFNg | | | ■ | ■ | ■ | ■ | ND | ■ | ■ |
| N/A | 505 | No IL1TNF | | | ■ | ■ | ■ | ■ | ░ | ░ | ■ |
| N/A | 506 | No IL1TNF | | | ■ | ■ | ■ | ■ | | | ■ |
| N/A | 507 | No IL1TNF | | | ■ | ■ | ■ | ▒ | | ░ | ■ |
| N/A | 508 | No IL1TNF | | | ■ | ■ | ■ | ■ | | ░ | ■ |
| N/A | 509 | No IL1TNF | | | ■ | ■ | ■ | ■ | ND | | ■ |
| N/A | 500 | No IL1TNFIFNg | | | ■ | ■ | ■ | ░ | | ░ | ■ |
| N/A | 501 | No IL1TNFIFNg | | | ■ | ■ | ■ | ■ | | ▒ | ■ |
| N/A | 502 | No IL1TNFIFNg | | | ■ | ■ | ■ | ■ | | ■ | ■ |
| N/A | 503 | No IL1TNFIFNg | | | ■ | ■ | ■ | ■ | | ■ | ■ |
| N/A | 504 | No IL1TNFIFNg | | | ■ | ■ | ■ | ■ | ND | ░ | ■ |

Figure 4C:
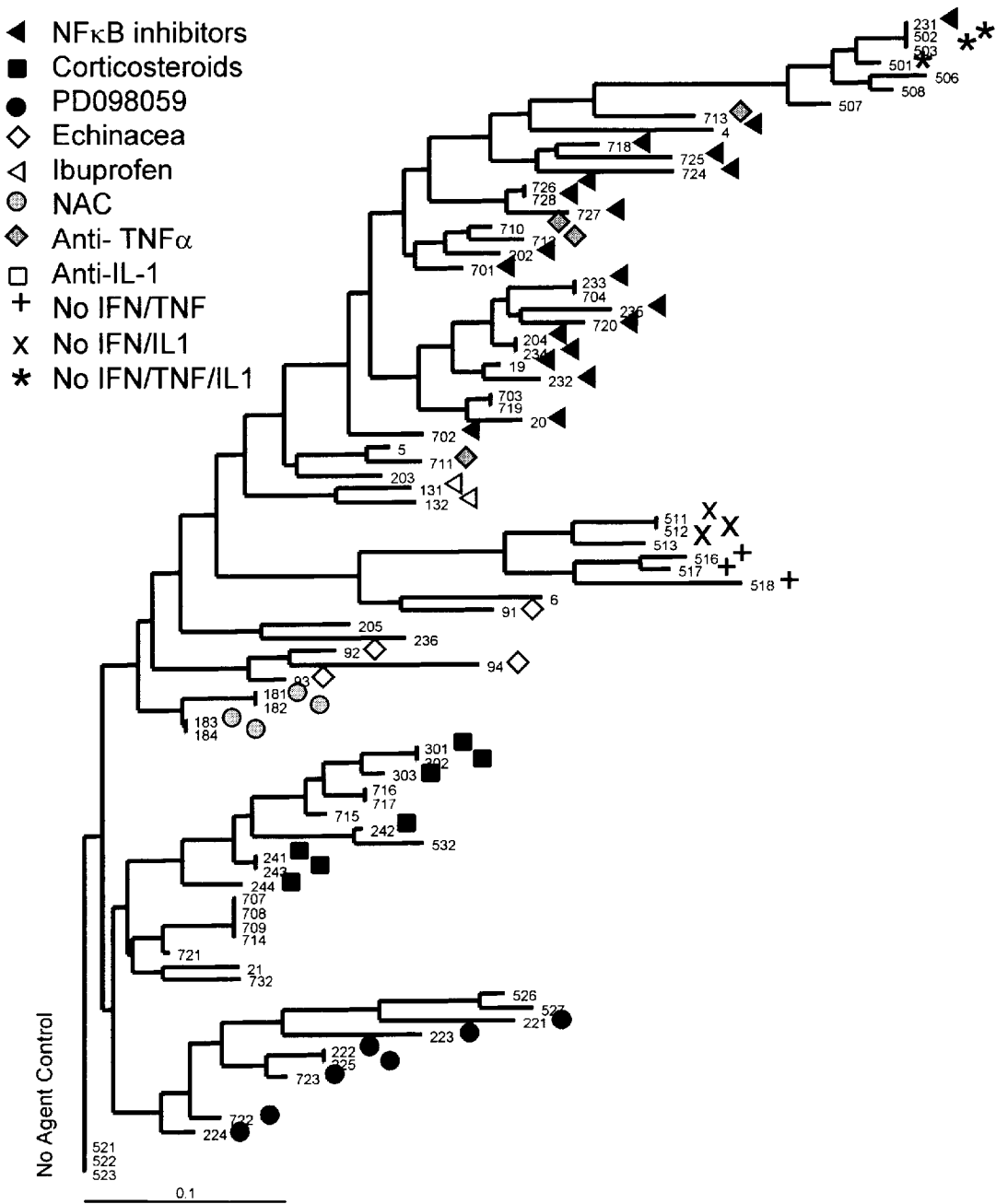

FIG. 4C shows a visual representation of how these reference biomaps can be compared by pattern similarity and cluster analysis. Readout patterns are analyzed by hierarchical clustering techniques, and are visualized as a tree diagram in which a) each terminal branch point represents the readout pattern from one assay combination in one experiment; b) the length of the vertical distance from the upper horizontal line (no change and control patterns) to the termini are related to the extent of difference in the readout pattern from the control environment pattern; and c) the distance along the branches from one terminal pattern value to another reflects the extent of difference between them. Similar patterns are thus clustered together.

Compounds that inhibit the NFκB pathway, such as the 5-lipoxygenase inhibitors AA861 and nordihydroguaiaretic acid (NHGA) (Lee, J. Immunol. 158, 3401, 1997), pyrrolidine dithiocarbamate (PDTC) (Boyle, Circulation 98:(19 Suppl):11282, 1998), PPM-18, a chemically synthesized naphthoquinone derivative (Yu, Biochem. J., 328:363, 1997) and the flavenoid apigenin (Gerritsen, Am. J. Pathol. 147:278, 1995), have similar reference biomaps and cluster together. The corticosteroids, dexamethasone and prednisolone also yield a set of related reference biomaps that are distinct from those of NFκB pathway inhibitors.

An important feature of biomap analysis is how biomaps resulting from different concentrations of active agents, although they differ from one another (see FIG. 4C), remain clustered together in the cluster analysis. This can be seen in FIG. 4C where the biomaps that result from testing PD098059 at different concentrations remain in the same cluster (indicating their similarity with one another), although biomaps resulting from testing PD098059 at higher concentrations are found in the lower branches of the cluster, indicating higher degree of difference (lower correlation coefficient) from the biomaps resulting from no intervention or inactive agents. Thus biomap analysis is useful for distinguishing the mode of action of a variety of compounds.

This example demonstrates that the biomaps are useful in distinguishing the mode of action of candidate compounds, so as to know whether combinations of candidate compounds act on the same pathway or different pathways, their combined effect on parameter levels and whether they provide synergy or act in an antagonistic way.

These assay combinations are highly useful for testing a large number of compounds or agents with many different or unknown mechanisms of action. This procedure balances the desirability of a screening assay that provides in depth information, with the advantages of an assay that is also amenable for scale-up high throughput screening. The assay combinations described are useful for general screening for compounds with anti-inflammatory or proinflammatory activity. Assay combinations tailored for specific inflammatory diseases are developed by altering the combination of input biologically active agents. For example, specific assay combinations useful for inflammatory diseases that are more Th2-like in nature, such as asthma or allergy should include additional agents, such as IL-4 or IL-13, that are preferably found in those disease conditions, and so forth.

EXAMPLE 2

Multiplex Assay Combinations for Distinguishing Mechanism of Action

The following example demonstrates the utility of the invention in identification of the mechanism of action of a test compound or intervention identified in the optimized assay combination of Example 1. This assay combination is included in a panel that contains specific and targeted alterations. A neutralizing antibody to TNF-α was selected as a test agent, as it is active when tested in the optimized primary assay combination of Example 1 (FIG. 3A). When the test agent is evaluated in the panel of assay combinations, it can be determined if the active compound is acting on a component(s) unique to one receptor-stimulated pathway, or on a common pathway component or pathway activity. The neutralizing antibody to TNF-α as a test agent evaluated in these assay combinations alters the biomap, as shown in FIG. 3B.

Figure 5:
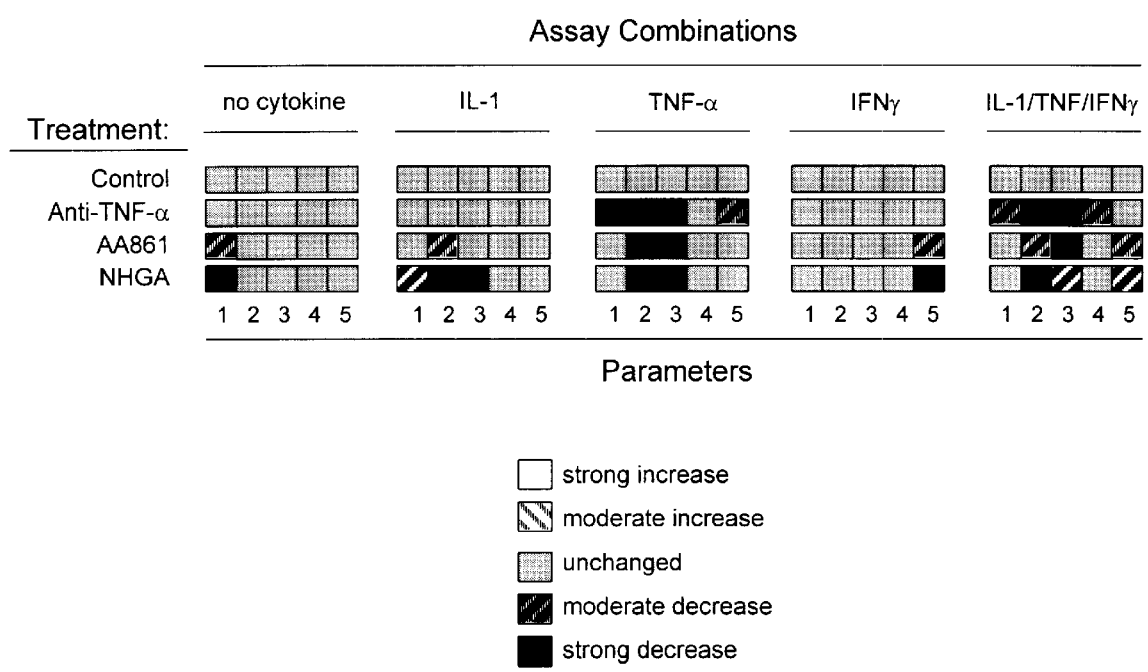
FIG. 5. Effect of neutralizing anti-TNF-α antibody or NFκB inhibitors AA861 and nordihydroguaiaretic acid (NHGA) on readout patterns in multiple assay combinations. Confluent cultures of HUVEC cells were treated with TNF-α (5 ng/ml), IFN-γ (200 ng/ml), IL-1 (1 ng/ml), the combination of TNF-α +IFN-γ+IL-1, or media in the presence or absence of 5 μg/ml neutralizing anti-TNF-α (R&D Systems), 20 μM AA861 or 10 μM NHGA. After 24 hours, cultures were washed and evaluated for the cell surface expression of ICAM-1 (1), VCAM-1 (2), E-selectin (3), IL-8 (4), and MIG (5) by cell-based ELISA performed as described in FIG. 1. A color-coded representation of the biomaps prepared from the data is shown, coded as described in FIG. 2B.

Confluent cultures of HUVEC cells are treated with TNF-α (5 ng/ml), IFN-γ (100 ng/ml), IL-1 (20 ng/ml), the combination of TNF-α+IFN-γ+IL-1, or media (no cytokine) in the presence or absence of neutralizing anti-TNF-α, 20 μM AA861 or 10 μM NHGA. After 24 hours, cultures are washed and evaluated for the cell surface expression of ICAM-1 (1), VCAM-1 (2), E-selectin (3), IL-8 (4), and MIG (5) by cell-based ELISA performed as described in FIG. 1. A color-coded representation of the resulting biomaps derived from the data is shown in FIG. 5, coded as described in FIG. 2B.

These data demonstrate expression of the biomap from the assay combination containing TNF-α alone is altered, but not the biomap in the assay combinations that contain IL-1 or IFN-γ alone. This result demonstrates that the test agent acts on the TNF-α pathway but not on the IL-1 or IFN-γ pathways. FIG. 5 also shows the test compound is distinguished from active compounds that target multiple cytokine signaling pathways, such as the NFκB inhibitors, NHGA and M861.

The mechanism of action of the test agent is accomplished when identical biomaps are obtained from assay combinations containing the test agent and assay combinations generated from known specific alterations of the assay combination. Eliminating the cytokine TNF-α from the primary assay combination results in the same biomap as the assay combination containing the test agent, the neutralizing TNF-α antibody.

Figure 6:
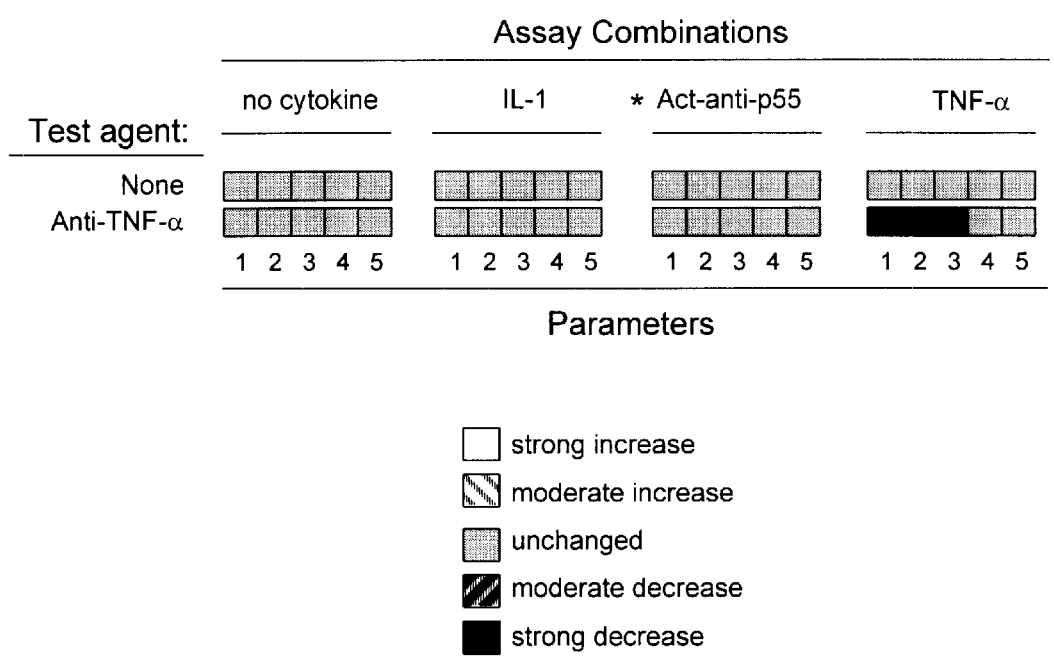
FIG. 6. Effect of a neutralizing anti-TNF-α antibody on readout patterns in multiple assay combinations. Confluent cultures of HUVEC cells were treated with TNF-α (5 ng/ml), IL-1 (1 ng/ml), an activating antibody against the TNF-α-receptor p55, (Act-anti-p55, 3 μg/ml, R&D Systems), or media in the presence or absence of neutralizing TNF-α antibody (Anti-TNF-α, 5 μg/ml, R&D Systems). After 24 hours, cultures were washed and evaluated for the cell surface expression of ICAM-1 (1), VCAM-1 (2), E-selectin (3), CD31 (4), and MIG (5) by cell-based ELISA performed as described in FIG. 1. A color-coded representation of the biomaps prepared from the data is shown, coded as described in FIG. 2B.

Confirmation is performed by evaluating the test agent in assay combinations that include both physiologic and alternative pathway activators. Confluent cultures of HUVEC cells are treated with TNF-α (5 ng/ml), IL-1 (20 ng/ml), an activating antibody against the TNF-α receptor p55, or media. After 24 hours, cultures are washed and evaluated for the cell surface expression of ICAM-1 (1), VCAM-1 (2), E-selectin (3), CD31 (4), and MIG (5) by cell-based ELISA performed as described in FIG. 1. A color-coded representation of the resulting biomap, prepared from the data is shown in FIG. 6, coded as described in FIG. 2B. FIG. 6 shows that among the physiologic and alternative activators of the TNF-a pathway, the biomaps resulting from cultures containing either IL-1 or an activating antibody to p55 are not sensitive to the test agent, whereas the biomap resulting from cultures containing TNF-α is sensitive. As TNF-α is the most upstream component of the TNF-α pathway that is sensitive to the test agent, it is involved in the target pathway step of the test agent.

Example 3

Analysis in Multiplex Assay Combinations for Identifying Mechanism of Action

Figure 7A:
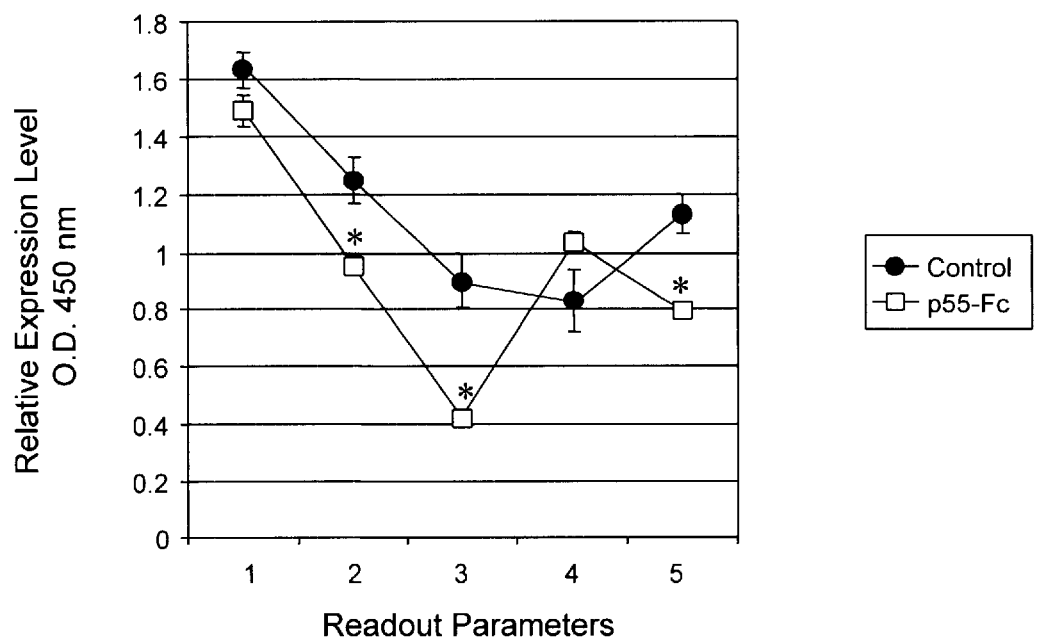
FIG. 7. Effect of soluble TNF-α-receptor p55-Fc fusion protein (p55-Fc) on the expression of readout parameters in multiple assay combinations. A. Confluent cultures of HUVEC cells were treated with TNF-α (5 ng/ml)+IFN-γ (100 ng/ml)+IL-1 (1 ng/ml) in the presence or absence of p55-Fc (50 ng/ml, Pharmingen). After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. The relative expression of each parameter is shown along the y-axis as average value of the OD measured at 450 nm of triplicate samples. The mean +/– SD from triplicate samples are shown. * indicates p<0.05 comparing results obtained with anti-TNF-α to the control. B. Confluent cultures of HUVEC cells were treated with TNF-α (5 ng/ml), IFN-γ (100 ng/ml), IL-1 (1 ng/ml), the combination of TNF-α+IFN-γ+IL-1, or media in the presence or absence of p55-Fc (50 ng/ml, Pharmingen). After 24 hours, cultures were washed and evaluated for the cell surface expression of ICAM-1 (1), VCAM-1 (2), E-selectin (3), IL-8 (4), and MIG (5) by cell-based ELISA performed as described in FIG. 1. A color-coded representation of the biomaps prepared from the data is shown, coded as described in FIG. 2B. C. Confluent cultures of HUVEC cells were treated with TNF-α (5 ng/ml), IL-1 (1 ng/ml), an activating antibody against the TNF-α-receptor p55 (5 µg/ml, Pharmingen), or media with or without p55-Fc (50 ng/ml). After 24 hours, cultures were washed and evaluated for the cell surface expression of ICAM-1 (1), VCAM-1 (2), E-selectin (3), CD31 (4), and MIG (5) by cell-based ELISA performed as described in FIG. 1. A color-coded representation of the biomaps prepared from the data is shown, coded as described in FIG. 2B.

The following example demonstrates the usefulness of the present invention for identification of mechanism of action of a test agent selected as an active agent. A recombinant fusion protein containing the extracellular domains of the p55 TNF-α-receptor fused to immunoglobulin Fc domain (p55-Fc fusion protein) is selected as an active compound when tested in the optimized assay combination of Example 1 (FIG. 7A).

Confluent cultures of HUVEC cells are treated with TNF-α (5 ng/ml)+IFN-γ (100 ng/ml)+IL-1 (20 ng/ml) in the presence or absence of p55-Fc (50 ng/ml). After 24 hours, cultures are washed and evaluated for the cell surface expression of ICAM-1 (1), VCAM-1 (2), E-selectin (3), CD31 (4), and MIG (5) by cell-based ELISA performed as described in FIG. 1. The relative expression of each parameter is shown in FIG. 7A along the y-axis as average value of the OD measured at 450 nm of triplicate samples. The mean +/− SD from triplicate samples are shown. * indicates $p<0.05$ comparing results obtained with p55-Fc to the control.

Figure 7B:
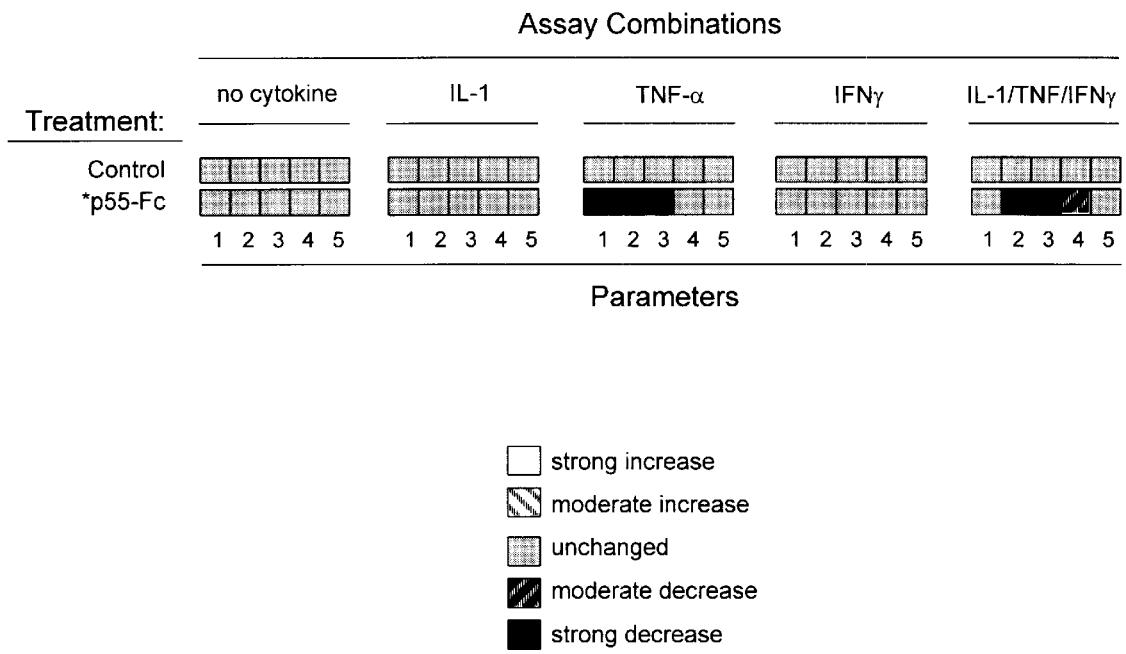
Figure 7C:
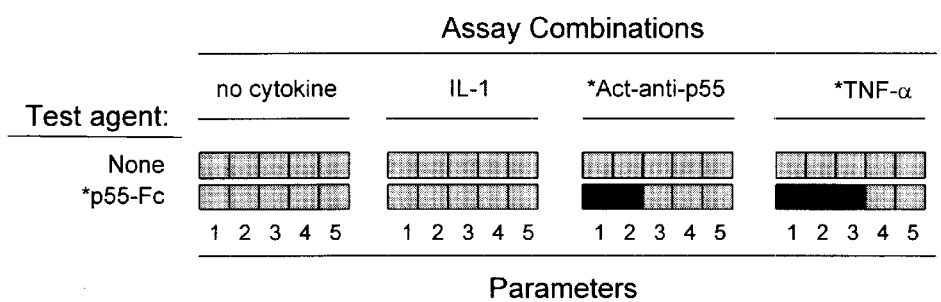

In FIG. 7B, confluent cultures of HUVEC cells are treated with TNF-α (5 ng/ml), IFN-γ (100 ng/ml), IL-1 (20 ng/ml), the combination of TNF-α+IFN-γ+IL-1, or media in the presence or absence of p55-Fc. After 24 hours, cultures are washed and evaluated for the cell surface expression of ICAM-1 (1), VCAM-1 (2), E-selectin (3), IL-8 (4), and MIG (5) by cell-based ELISA performed as described in FIG. 1. A color-coded representation of the resulting biomaps prepared from the data is shown in FIG. 7B, coded as described in FIG. 2B. In FIG. 7C, confluent cultures of HUVEC cells are treated with TNF-α (5 ng/ml), IL-1 (20 ng/ml), an activating antibody against the TNF-α receptor p55, or media. After 24 hours, cultures are washed and evaluated for the cell surface expression of ICAM-1 (1), VCAM-1 (2), E-selectin (3), CD31 (4), and MIG (5) by cell-based ELISA performed as described in FIG. 1. A color-coded representation of the resulting biomaps prepared from the data is shown in FIG. 7C, coded as described in FIG. 2B.

The p55-Fc fusion protein as a test agent evaluated in these assay combinations, alters the biomap, as shown in FIG. 7B. The biomap in the assay combination containing TNF-α alone is altered, but not the biomap in the assay combinations that contain IL-1 or IFN-γ alone. This result demonstrates that the test agent acts on the TNF-α pathway but not on the IL-1 or IFN-γ pathways.

FIG. 7C shows that among the physiologic and alternative activators of the TNF-α pathway, the biomap from IL-1 is not sensitive to the test agent, whereas the biomap from TNF-α or an activating antibody to the p55 is sensitive to the test agent. As the TNF-α-receptor p55 is the most upstream component of the TNF-α pathway that is sensitive to the test agent, it is a component of the target step of the test agent.

Example 4

Analysis in Multiplex Assay Combinations for Identifying Mechanism of Action

The following example demonstrates the usefulness of the present invention for identification of mechanism of action of test agents that have proinflammatory activities. An activating antibody to TNF-α-receptor p55 (Act-anti-p55) is an active compound when tested in an assay combination containing confluent HUVEC cultured in a basal medium for 24 hours (FIG. 8, "no cytokine" assay combination), since Act-anti-p55 alters the biomap of this assay combination resulting in increased levels of the readout parameters ICAM-1 (1), E-selectin (2) and VCAM-1 (3), and reduced levels of the readout parameter CD31 (4).

For identifying the mechanism of action and determining the cellular target, the test compound is evaluated in secondary or "decoding" assay combinations. These combinations contain the test agent as well as known regulators of the modulated parameters. For the parameters ICAM-1, VCAM-1 and E-selectin, known modulators include IL-1 and TNF-α (ICAM-1, VCAM-1 and E-selectin); and IFN-γ (ICAM-1 and VCAM-1).

Confluent cultures of HUVEC cells are treated with TNF-α (5 ng/ml), IFN-γ (100 ng/ml), IL-1 (20 ng/ml), the combination of TNF-α+IFN-γ+IL-1, or media in the presence or absence of Act-anti-p55. After 24 hours, cultures are washed and evaluated for the cell surface expression of ICAM-1 (1), VCAM-1 (2), E-selectin (3), IL-8 (4), and MIG (5) by cell-based ELISA performed as described in FIG. 1. A color-coded representation of the resulting biomaps prepared from the data is shown in FIG. 8, coded as described in FIG. 2B.

Figure 8:
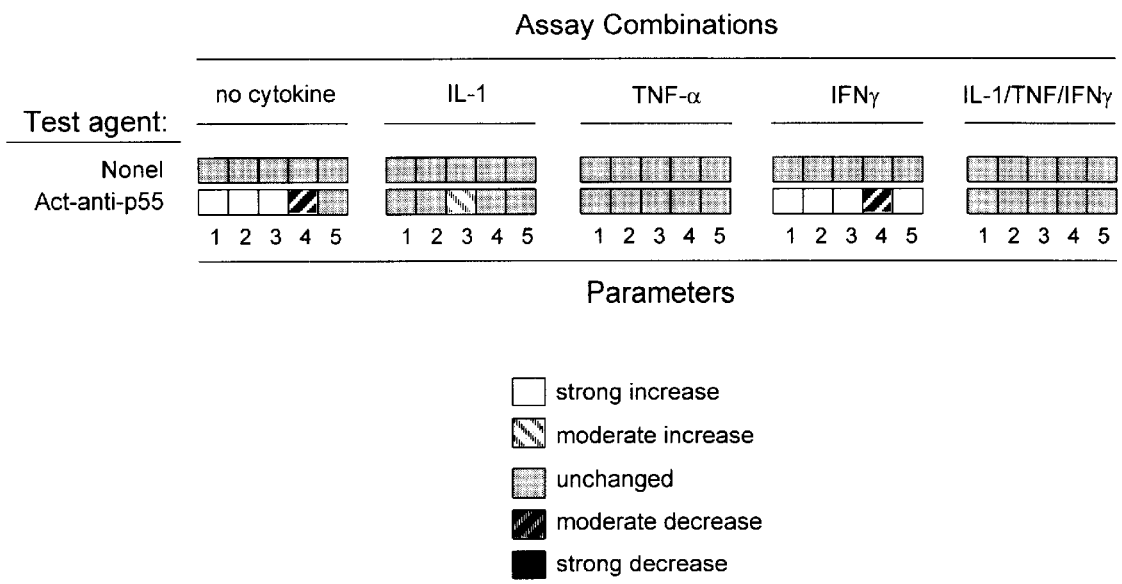
FIG. 8. Effect of an activating antibody against TNF-α-receptor p55 (Act-anti-p55) on readout patterns in multiple assay combinations. Confluent cultures of HUVEC cells were treated with TNF-α (5 ng/ml), IFN-γ (100 ng/ml), IL-1 (1 ng/ml), the combination of TNF-α+IFN-γ+IL-1, or media in the presence or absence of Act-anti-p55 (Act-anti-p55, 3 µg/ml, R&D Systems). After 24 hours, cultures were washed and evaluated for the cell surface expression of ICAM-1 (1), VCAM-1 (2), E-selectin (3), IL-8 (4), and MIG (5) by cell-based ELISA performed as described in FIG. 1. A color-coded representation of the biomaps prepared from the data is shown, coded as described in FIG. 2B.

FIG. 8 shows that the test agent alters the biomaps derived of assay combinations containing IL-1 or IFN-γ, but not the biomaps resulting from assay combinations containing TNF-α. This result indicates that the test compound acts through a pathway that is distinct from the IL-1 and IFN-γ pathways but that cannot be distinguished from the TNF-α pathway in these assay combinations. To confirm that the test compound acts through the TNF-α pathway, and to identify the pathway step targeted by the test agent, the test agent is evaluated in assay combinations that contain known inhibitors of the TNF-α pathway. The recombinant fusion protein, p55-Fc, is an example of a known inhibitor of the TNF-α pathway.

Figure 9:
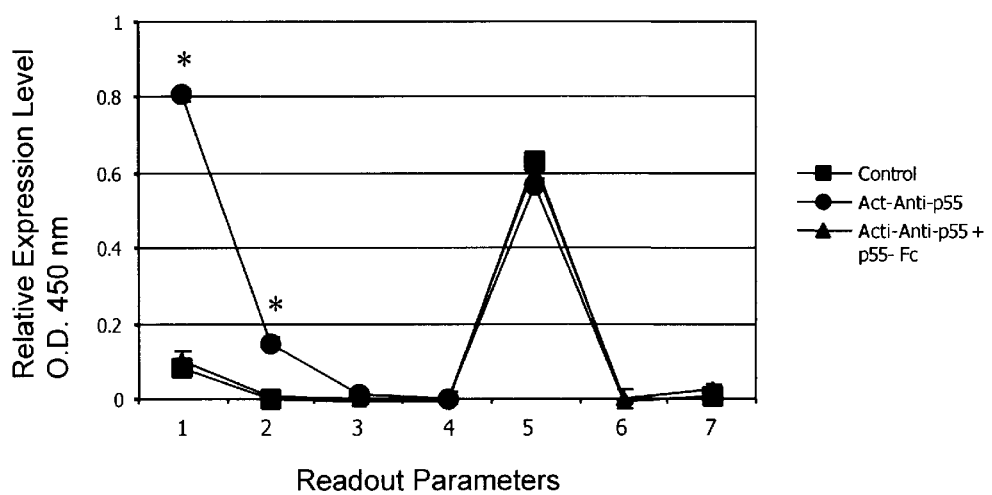
FIG. 9. Effect of a soluble TNF-α-receptor p55-Fc fusion protein (p55-Fc) on the expression of readout parameters in an assay combination containing an activating antibody against TNF-α-receptor p55 (Act-anti-p55). Confluent cultures of HUVEC cells were treated with or without (Control) Act-anti-p55 in the presence or absence of p55-Fc. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. The relative expression of each parameter is shown along the y-axis as average value of the OD measured at 450 nm of triplicate samples. The mean +/– SD from triplicate samples are shown. * indicates p<0.05 comparing results obtained with Act-anti-p55 or Act-anti-p55+p55-Fc to the Control, n=3.

As shown in FIG. 9, confluent cultures of HUVEC cells are treated with Act-anti-p55 in the presence or absence of p55-Fc. After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. FIG. 9 shows the relative expression (y-axis) of each parameter (x-axis) as average value of the OD measured at 450 nm of triplicate samples. The mean +/− SD from triplicate samples are shown. * indicates $p<0.05$ comparing results obtained with Act-anti-p55 or Act-anti-p55+p55-Fc to the Control.

As shown in FIG. 9, p55-Fc fusion protein, a soluble form of the p55 TNF-α receptor, that blocks TNF-α binding to the TNF-α receptor, alters the biomap generated by the test agent. This demonstrates that the pathway step targeted by the test agent is upstream or includes the p55 TNF-α receptor. Since a neutralizing antibody to human TNF-α does not alter the biomap generated by the test agent, the target pathway step of the test agent does not include human TNF-α.

Example 5

Drug Interaction Screening

The present invention is useful for analysis of combinatorial drug interactions. Drug interactions occur if the presence of two drugs produces a readout response pattern, or biomap, different from those produced by either compound alone in an assay combination. Drugs may act on independent molecular targets within the cell but nonetheless produce a combined cellular phenotype that is distinct and potentially physiologically or therapeutically different in its effects. Drug combinations may have synergistic or counteracting effects, in which one compound enhances or suppresses the effects of another on a parameter or parameters, or alters the dose response, and may imply a more complex drug interaction at the level of intracellular pathways. Interaction may be beneficial if resulting combined activity is desirable; alternatively, interaction may be detrimental if the resulting combined activity is undesirable. The desirability of a particular drug interaction activity depends on the context. For example, a drug combination that results in increased toxicity compared to either drug alone may be undesirable for an anti-inflammatory therapeutic, but desirable for a cancer therapeutic. The present invention is highly useful for distinguishing combinatorial drug activities since the assay combinations described are designed to measure the outcome of multiple signaling pathways and their interactions.

Figure 10A:
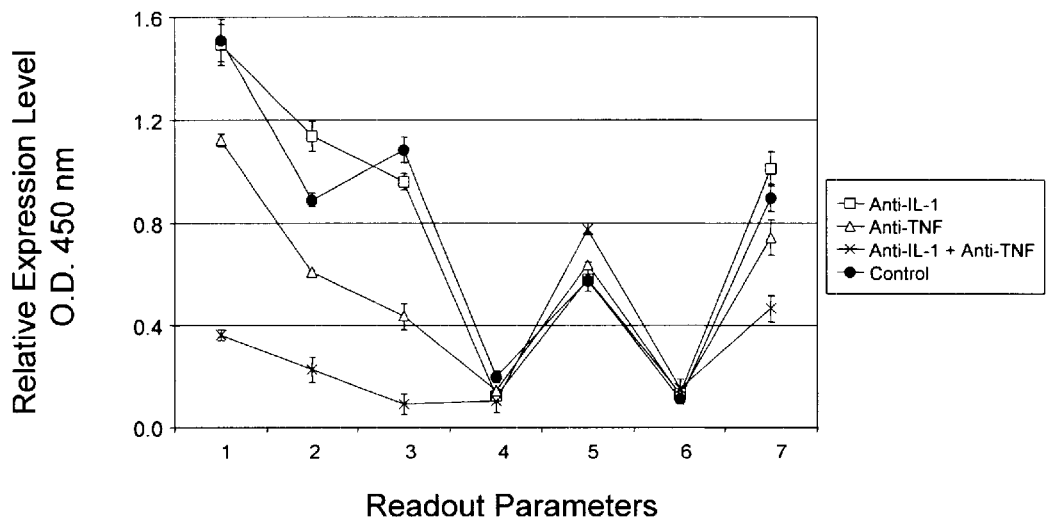
FIG. 10. Effect of neutralizing antibodies against IL-1 or TNF-α on the expression of readout parameters in the optimized assay combination of Example 1. Confluent cultures of HUVEC cells were treated with TNF-α (5 ng/ml)+IFN-γ (100 ng/ml)+IL-1 (1 ng/ml) in the presence or absence of neutralizing antibodies to IL-1 (Anti-IL-1, 4 µg/ml, R&D Systems), TNF-α (Anti-TNF-α, µg/ml/ml, R&D Systems) or the combination. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A. The relative expression of each parameter is shown along the y-axis as average value of the OD measured at 450 nm of triplicate samples. The mean +/– SD from triplicate samples are shown. B. A color-coded representation of the biomaps prepared from the data in FIG. 12A is shown, coded as described in FIG. 2B where the control condition includes TNF-α+IFN-γ+IL-1.
Figure 10:
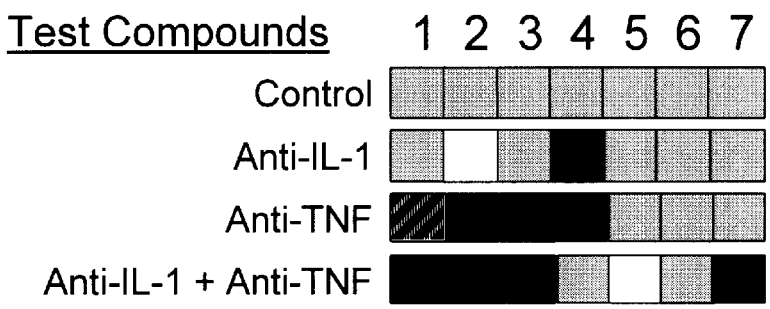

A neutralizing antibody to TNF-α and a neutralizing antibody to IL-1 are both active compounds when screened in the optimized assay combination of Example 1 (FIG. 10A). Confluent cultures of HUVEC cells are treated with TNF-α (5 ng/ml)+IFN-γ (100 ng/ml)+IL-1 (20 ng/ml) in the presence or absence of neutralizing antibodies to IL-1, TNF-α or the combination. Antibody concentrations are in excess as increased concentrations of antibodies does not further alter the biomaps. After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. In FIG. 10A the relative expression of each parameter is shown along the y-axis as average value of the OD measured at 450 nm of triplicate samples. The mean +/− SD from triplicate samples are shown. FIG. 10B shows a color-coded representation of the resulting biomaps prepared from the data coded as described in FIG. 2B. FIG. 10B demonstrates that when saturating concentrations of the neutralizing antibodies to TNF-α and IL-1 are included together in the assay combination, a biomap is obtained that is different from the biomap obtained by assay combinations containing each test agent individually, even though the test agents are provided at saturating (excess) concentrations. Compounds that result in similar biomaps are diagnostic of inhibitors that target both the IL-1 and TNF-α pathways. The present system therefore provides an assay system for screening for and distinguishing such inhibitors.

Example 6

Drug Interaction Screening

Figure 11:
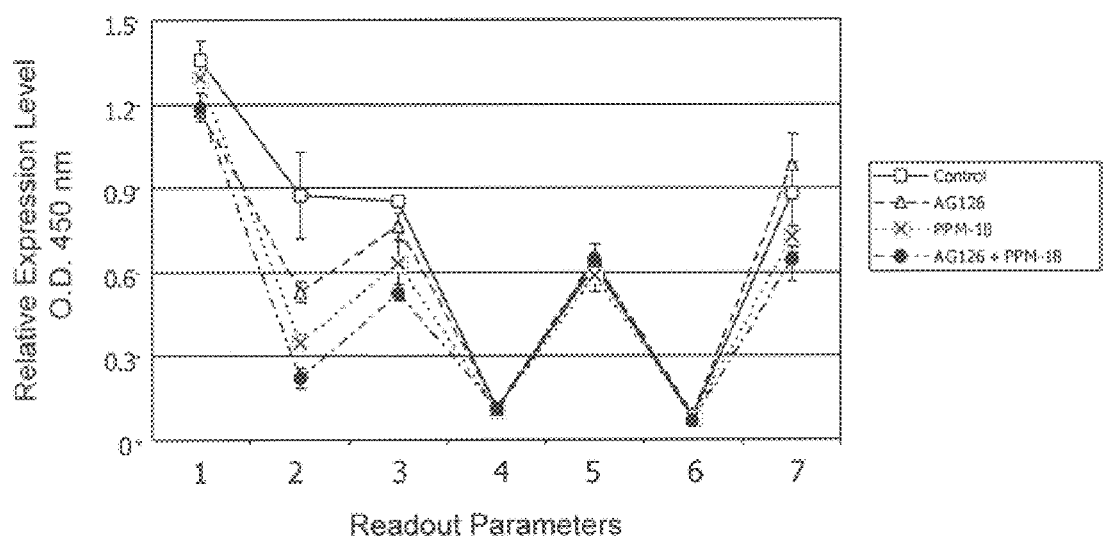
FIG. 11. Effect of AG126 and PPM-18 on expression of readout parameters in the optimized assay combination of Example 1. Confluent cultures of HUVEC cells were treated with TNF-α (5 ng/ml)+IFN-γ (100 ng/ml)+IL-1 (1 ng/ml) in the presence or absence of AG126 (25 µM) or PPM-18 (2 µM) or the combination. Compounds were tested at the highest concentration at which they were soluble, and/or did not result in cell deadhesion. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A color-coded representation of the biomaps prepared from the data is shown, coded as described in FIG. 2B.
Figure 11:
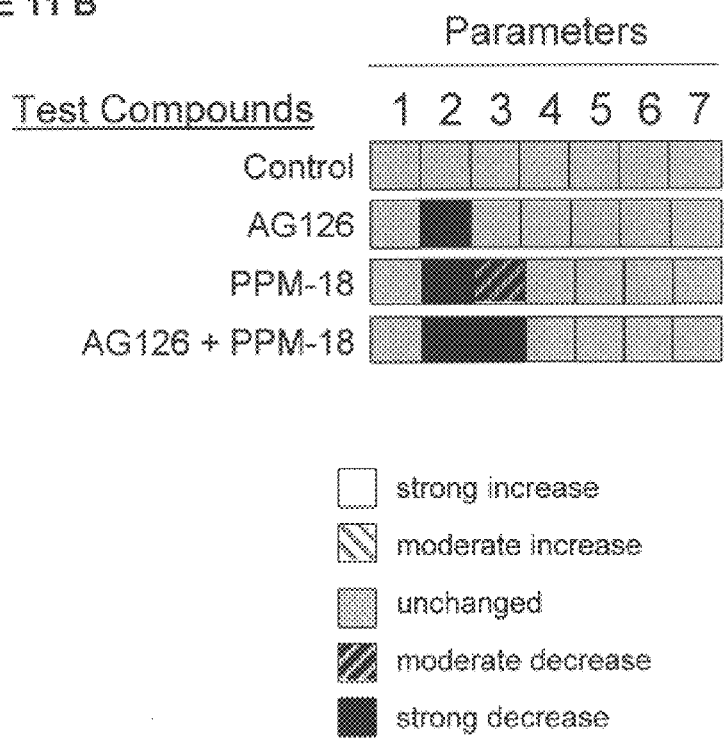

The present invention is useful for the identification of drug interactions or drug combinations that are beneficial. For the present example, the NFκB inhibitor PPM-18 (at 2 μM) (Yu, Biochem. J. 328:363, 1997) and the tyrosine kinase inhibitor AG126 (25 μM) (Novogrodsky, Science 264, 1319, 1994) are both active compounds when screened in the assay combination of Example 1 (FIG. 11A). Confluent cultures of HUVEC cells are treated with TNF-α (5 ng/ml)+IFN-γ (100 ng/ml)+IL-1 (20 ng/ml) in the presence or absence of the tyrphostin AG126 (25 μM), PPM-18 (2 μM) or the combination. After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. The relative expression of each parameter is shown in FIG. 11A as average value of the OD measured at 450 nm of triplicate samples. The mean +/− SD from triplicate samples are shown. FIG. 11B shows a color-coded representation of the resulting biomaps prepared from the data, coded as described in FIG. 2B.

In this example, higher concentrations of either drug (2-fold) when tested alone result in cellular toxicity. Together, however, the combination of PPM-18 and AG126 at non-toxic concentrations produces a combined cellular phenotype that is additive for the effect on biomap parameters, but is not toxic to cells (FIG. 11B). The present system, therefore, provides an assay system for screening for compounds that synergize with inhibitors of NFκB, or with tyrosine kinase inhibitors to produce a desirable phenotype, without resulting in cellular toxicity.

Example 7

Regulators of Endothelial Cell Responses to Allergic Inflammation

The present invention is applied for the screening of compounds for use in treating allergic inflammatory responses such as allergy, asthma, atopic dermatitis and chronic inflammatory diseases disposed towards a Th2 phenotype or modulation of Th2 type immune responses.

Primary human umbilical vein endothelial cells are used. Other cells that may replace HUVEC in the screen include primary microvascular endothelial cells, aortic endothelial cells. $2 \times 10^4$ cells/ml are cultured to confluence in EGM-2 (Clonetics). Other media that may replace EGM-2 include EGM (Clonetics) and Ham's F12K medium supplemented with 0.1 mg/ml heparin and 0.03–0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984). Following overnight serum starvation, the following are then applied for 24 hours: VEGF (10 ng/ml), TNF-α (1 ng/ml) and bFGF (10 ng/ml). In subsequent panels one or more of IL-4 (20 ng/ml), IL-13 (20 ng/ml), EGF (10 ng/ml), hydrocortisone (2 ng/ml), thrombin (0.1 U/ml), hypoxic conditions (Xu, JBC 275:24583, 2000); and/or neutralizing antibodies to autocrine factors, such as TGF-β, IL-8 or IL-6 are added to the initial three factors or may replace one of the three factors. Standard concentrations of agents are employed as described in the literature (Thakker, JBC 274:10002, 1999; Kikuchi, NRMGK 23:12, 2000; Woltmann, Blood 95:3146, 2000; Wu, JBC 275:5096, 2000). Based on the parameters altered by the indicated factors, biomaps are generated for the parameters alphavbeta3, IL-8, VCAM-1, von Willebrand factor, E-selectin, fibronectin and uPAR (Friedlander, Science 270:1500, 1995; Zanetta, Int. J. Cancer 85, 281, 2000). Other markers of interest for adding to the biomap include: thrombomodulin, Tissue Factor, MMP-2, MMP-3, $\alpha_5\beta_1$, $\alpha_v\beta_5$, CD105, CXCR4 and CD31 (St. Croix, Science 289:1197, 2000; Friedlander, Science 270:1500, 1995; Bodey, Anticancer Res. 18:3621, 1998).

Figure 12:
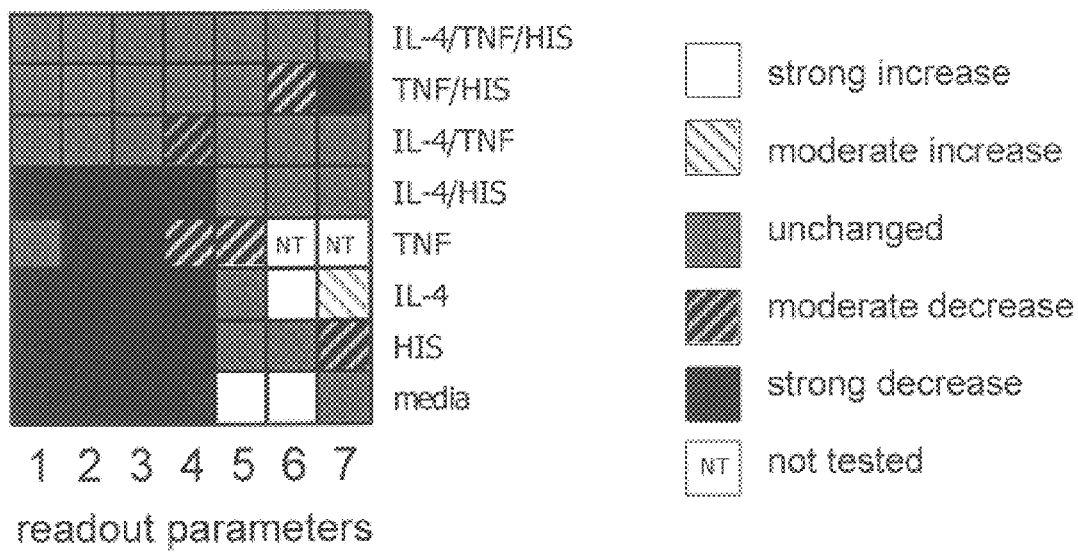
FIG. 12. Confluent cultures of HUVEC cells were treated with combinations of IL-4 (20 ng/ml), TNF-α (5 ng/ml), histamine (HIS, 10 µM) and/or base media. After 24 hours, cultures were washed and evaluated for the presence of ICAM-1 (1), VCAM-1 (2), E-selectin (3), IL-8 (4), CD31 (5), P-selectin (6) and Eotaxin-3 (7) by cell-based ELISA performed as described in FIG. 1. A color-coded representation of the biomaps prepared from the data is shown, coded as described in FIG. 2B. For each parameter and assay combination, the square is colored light gray if the parameter measurement is unchanged (<20% above or below the measurement in the first assay combination (IL-4+TNF-α+HIS) or p>0.05, n=3); white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

The following are then applied for 24 hours: IL-4 (20 ng/ml), HIS (10 μM) and TNF-α (5 ng/ml). In subsequent panels one or more of IL-1 (1 ng/ml), IFNγ, (100 ng/ml) IL-13 (20 ng/ml), mast cell tryptase, or fibronectin are added to the initial three factors or may replace one of the factors. Standard concentrations of agents are employed as described in the literature. Based on the parameters altered by the indicated factors, biomaps are generated for the parameters ICAM-1, VCAM-1, E-selectin, IL-8, CD31, P-selectin and Eotaxin-3. Other markers of interest for adding to the biomap include: Eotaxin-1, HLA-DR, MIG, Tarc, MCP-1, and IL-8. FIG. 12 shows biomaps resulting from confluent cultures of HUVEC cells treated with IL-4 (20 ng/ml), HIS (10 μM), TNF-α (5 ng/ml), and/or media. After 24 hours, cultures are washed and evaluated for the presence of the parameters ICAM-1 (1), VCAM-1 (2), E-selectin (3), IL-8 (4), CD31 (5), P-selectin (6) and eotaxin-3 (7) by cell-based ELISA performed as described in FIG. 1. FIG. 12 shows a visual representation of the resulting biomaps prepared from the data, where the measurement obtained for each parameter is classified according to its relative change from the value obtained in the assay combination containing IL-4+TNF-α+HIS, and represented by shaded squares. For each parameter and assay combination, the square is gray if the parameter measurement is unchanged (<20% above or below the measurement in the first assay combination (IL-4+TNF-α+HIS)) or p>0.05, n=3; white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

A database of biomaps is generated from a panel of assay combinations that include the presence and absence of each biologically active factor; and reference drugs or agents including inhibitors of signaling pathways such as NFkB and STAT inhibitors, anti-histamine or histamine receptor antagonists; as well as immune stimulatory agents including pathogens or pathogen components, that are screened and biomaps generated that show the changes in the markers with the different agents. Many agents are given in The Pharmacologic Basis Of Therapeutics. The biomaps with the known agents are used to compare to candidate agents. This allows the recognition of the pathway(s) the candidate agent acts on, by comparing the changes in the level of the specific markers for known drugs affecting known pathways and the changes observed with the candidate agent. In addition to further add to the utility of the biomap, one may include in the database reference biomaps generated from assay panels containing cells with genetic constructs that selectively target or modulate specific cellular pathways (e.g. NFkB, MAP kinase, etc), or cells that contain known genetic mutations.

Example 8

Regulators of Epithelial Cell Responses to Inflammation

The present invention is applied for the screening of compounds that regulate epithelial cell responses to inflammation.

Normal human epithelial keratinocytes (NHEK) ($5 \times 10^4$ cells/ml) are cultured to 80% confluence in serum free Keratinocyte Basal Medium-2 (Clonetics CC3103) supplemented with BPE (30 μg/ml), hEGF (100 ng/ml), insulin (5 μg/ml), transferrin (10 μg/ml), and epinephrine (500 ng/ml). Other cells that may substitute for NHEK include the spontaneously immortalized keratinocyte cell line, HaCaT (Boukamp, J. Cell Biol. 106:761, 1988), normal human lung epithelial cells (NHLE), renal, mammary and intestinal epithelial cells. One or more of the following are applied for 48 hours: IFN-γ (50 ng/ml), TNF-α (50 ng/ml) and IL-1 (20 ng/ml). Based on the parameters altered by the indicated factors, biomaps are generated for the parameters MIG, ICAM-1, CD44, IL-8, Mip-3 alpha (CCCL20), MCP-1, and E-Cadherin. Other parameters of interest for including in biomaps are: CD40, IP-10, EGF-Receptor, IL-6, IL-15Ralpha, CD1d, CD80, CD86, TARC, eotaxin-1, eotaxin-3, HLA-DR and CD95. Other factors of interest for including in assay combinations include TGFβ, IL-9, GM-CSF, CD40L and IL-17 activities.

Figure 13:
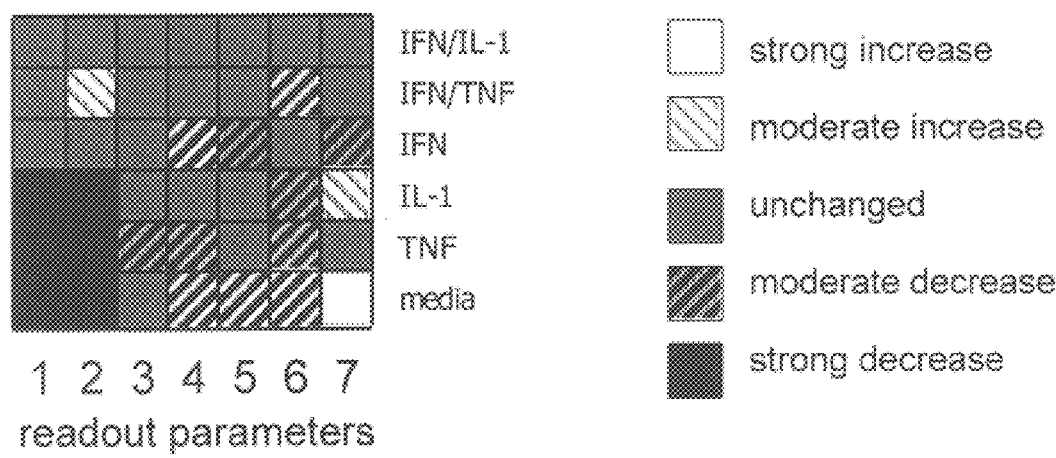
FIG. 13. Cultures of normal human epithelial keratinocytes (NHEK) were treated with combinations of TNF-α (50 ng/ml), IFN-γ (50 ng/ml), IL-1 (1 ng/ml) and or base media. After 48 hours, cultures were washed and evaluated for the presence of MIG (1), ICAM-1 (2), CD44 (3), IL-8 (4), MIP-3alpha (5), MCP-1 (6), and E-cadherin (7) by cell-based ELISA performed as described in FIG. 1. A color-coded representation of the biomaps prepared from the data is shown, coded as described in FIG. 2B. For each parameter and assay combination, the square is colored light gray if the parameter measurement is unchanged (<20% above or below the measurement in the first assay combination (IL-1+IFN-γ) or p>0.05, n=3); white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

In FIG. 13, confluent cultures of NHEK cells are treated with one or more of IFN-γ (50 ng/ml), TNF-α (50 ng/ml), IL-1 (20 ng/ml) and/or base media. After 48 hours, cultures are washed and evaluated for the presence of the parameters Mig (1), ICAM-1 (2), CD44 (3), IL-8 (4), Mip-3 alpha (5), MCP-1 (6), and E-Cadherin (7) by cell-based ELISA performed as described in FIG. 1. FIG. 13 shows a visual representation of the resulting biomaps prepared from the data, where the measurement obtained for each parameter is classified according to its relative change from the value obtained in the assay combination containing IL-1+IFNγ, and represented by shaded squares. For each parameter and assay combination, the square is gray if the parameter measurement is unchanged (<20% above or below the measurement in the first assay combination (IL-1+IFN-γ)) or p>0.05, n=3; white/gray hatched indicates that the parameter measurement is moderately increased (>20% but <50%); white indicates the parameter measurement is strongly increased (>50%); black/gray hatched indicates that the parameter measurement is moderated decreased (>20% but <50%); black indicates that the parameter measurement is strongly decreased (>50% less than the level measured in the first assay combination).

A database of biomaps is generated from a panel of assay combinations that include the presence and absence-of each biologically active factor; and reference drugs or agents including inhibitors of signaling pathways such as NFkB and STATs, as well as immune stimulatory agents including pathogens or pathogen components, that are screened and biomaps generated that show the changes in the markers with the different agents. Many agents are given in The Pharmacologic Basis of Therapeutics. The biomaps with the known agents are used to compare to candidate agents. This allows the recognition of the pathway(s) the candidate agent acts on, by comparing the changes in the level of the specific markers for known drugs affecting known pathways and the changes observed with the candidate agent. In addition to further add to the utility of the biomap, one may include in the database reference biomaps generated from assay panels containing cells with genetic constructs that selectively target or modulate specific cellular pathways (e.g. NFkB, MAP kinase, etc), or cells that contain known genetic mutations.

Example 9

Regulators of T Cell Responses—T Cell-Endothelial Cell Co-Cultures

The present invention is applied for the screening of compounds for altering immune and/or inflammatory conditions that involve T cells.

Figure 14:
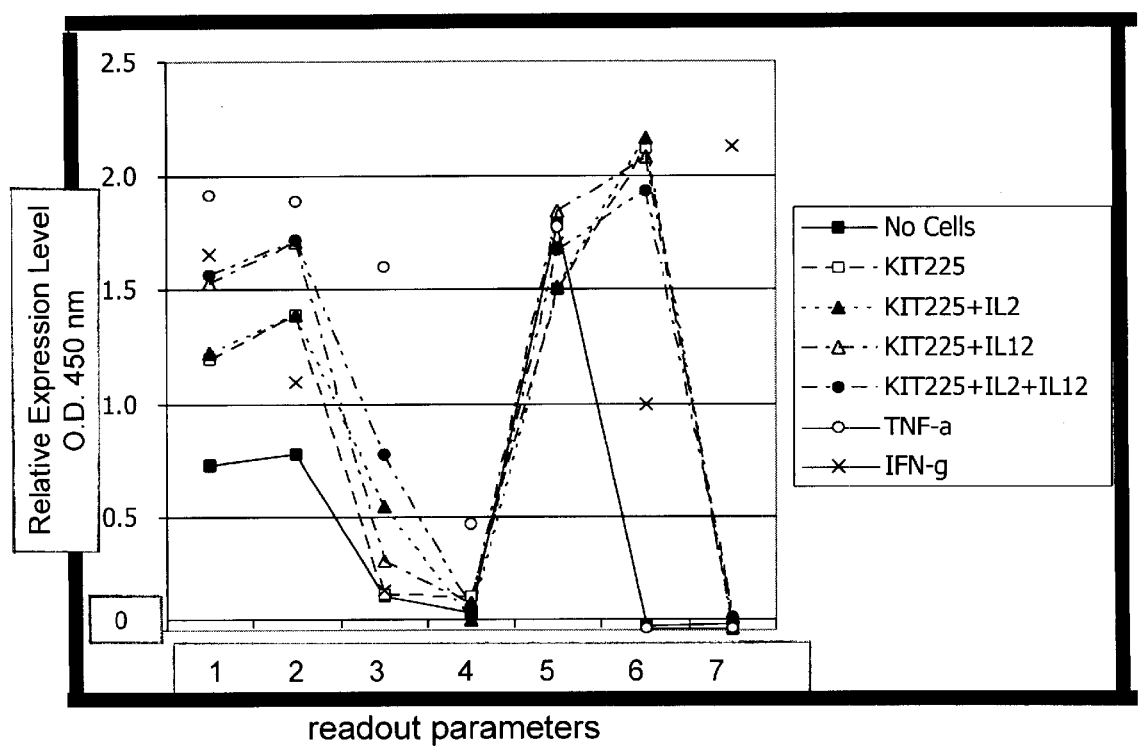
FIG. 14. Assay combinations containing HUVEC and T cell co-cultures. Confluent cultures of HUVEC were incubated with media (No Cells), TNF-α, (5 ng/ml), IFN-γ (100 ng/ml) or KIT255 T cells with and without IL-2 (10 ng/ml) and/or IL-12 (10 ng/ml). After 24 hours cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. The relative expression of each parameter is shown along the y-axis as average value of the OD measured at 450 nm.

Primary human umbilical vein endothelial cells and the human T cell line, KIT255 are used. Other cells that may replace HUVEC in the screen include primary microvascular endothelial cells or aortic endothelial cells. $2 \times 10^4$ HUVEC/ml were cultured to confluence in EGM-2 (Clonetics). Other media that may replace EGM-2 include EGM (Clonetics) and Ham's F12K medium supplemented with 0.1 mg/ml heparin and 0.03–0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984). One or more of the following are then applied: $10^3$ KIT255 cells, IL-2 (10 ng/ml), IL-12 (10 ng/ml), and or base media. After 24 hours, cultures are washed and evaluated for the presence of the parameters ICAM-1 (1), VCAM-1(2), E-selectin (3), IL-8 (4), CD31 (5), HLA-DR (6) and MIG (7) by cell based ELISA as described in FIG. 1 and shown in FIG. 14. In this figure, analysis performed by cell based ELISA provides readout patterns that combine HUVEC and T cell readouts. FIG. 14 demonstrates that the biomaps derived from assay combinations containing KIT255 cells +/− IL-2 and IL-12 can be distinguished. Other cells that may replace KIT255 include human peripheral blood leukocytes, human peripheral blood T cells, human peripheral blood CD3+cells, and the human T cell lines Jurkat and HUT78. In subsequent panels, one or more of: PHA, IL-6, IL-7, activating antibody to CD3, activating antibody to CD28, IL-1, TNF-$\alpha$, IFN-$\gamma$, IL-4, IL-13 or neutralizing antibodies to IL-1, IL-2, TNF-$\alpha$, IFN-$\gamma$, IL-12 and/or IL-4 are applied. Other markers of interest for adding to the biomap include MCP-1, IP-10, cutaneous lymphocyte antigen (CLA), CXCR3, CCR3, TNF-$\alpha$, IFN-$\gamma$, IL-2, IL-4, alpha4beta7, alphaEbeta7, and L-selectin. Analytical methods that distinguish T cells from endothelial cells, such as flow cytometry or image analytical techniques can be employed. A database of biomaps is generated from a panel of assay combinations that include anti-inflammatory drug compounds including inhibitors of T cell activation and/or T cell proliferation, calcineurin inhibitors, etc. are screened and biomaps are generated that reflect the changes in the markers with the different agents. Such agents are given in The Pharmacologic Basis of Therapeutics. The biomaps with the known agents are used to compare to candidate immunomodulatory agents. This allows the recognition of the pathway(s) the candidate test agent acts on, by comparing the changes in the level of the specific markers for known agents affecting known pathways and the changes observed with the candidate test agent. In addition to further add to the utility of the biomap, one may include in the database reference biomaps generated from assay panels containing cells with genetic constructs that selectively target or modulate specific cellular pathways (e.g. NFAT, calcineurin, NFκB, MAP kinase, etc), or cells that contain known genetic mutations, e.g. Jurkat cell lines that lack Ick, CD45, etc. (Yamasaki, J. Biol. Chem. 272:14787, 1997).

Example 10

Cancer Applications—Colon Carcinoma

The present invention is applied for the screening of compounds for use in treating colon carcinoma.

The human colon carcinoma cell line HT-29 is used. Other colon carcinoma cells lines that may replace HT-29 in the screen include CaCo-2, Colo201, DLD-1, HCC 2998, HCT116, KM-12, LoVo, LS-174, SW-48, SW-480, SW-620, SW-83 or T-84; or primary tumor cells. $2\times10^4$ cells/ml are cultured in McCoy's 5a Medium containing 1.5 mM L-glutamine and 10% FBS. Other media that may replace McCoy's 5a Medium include Eagle's Medium Ham's F12 Medium, Dulbecco's Modified Eagle's Medium and chemically defined McCoy's 5A serum-free medium (Life Technologies, Inc.) supplemented with 20 μg/ml insulin, 4 μg/ml transferrin, and 10 ng/ml epidermal growth factor. Other conditions of interest that may be used in subsequent assay combinations include assaying cultures with during log phase growth. Following overnight serum starvation the following are then applied for 48 hours: IGF-II (10 nM), TGF-$\beta$ (10 ng/ml), and TNF-$\alpha$ (100 ng/ml). In subsequent panels one or more of IL-1 (10 ng/ml), IL-4 (20 ng/ml), IL-13 (30 ng/ml), TGF-$\beta$ (10 ng/ml), IFN-$\gamma$ (200 U/ml), epidermal growth factor (10 ng/ml) and IL-6; and/or neutralizing antibodies to autocrine factors, IGF-II, IL-8 or TGF-$\beta$ or the receptor IGF-R I, are added to the initial three factors or may replace one of the three factors. Standard concentrations of agents are employed as described in the literature (Freier, Gut 44:704, 1999; Naylor, Cancer Res. 50:4436, 1990; Kanai, Br. J. Cancer 82:1717, 2000; Wright, JBC 274:17193, 1999; Zarrilli, JBC 271:8108, 1996; Murata, JBC 270:30829, 1996; Cardillo, J. Exp. Clin. Cancer Res. 16:281, 997; Rajagopal, Int. J. Cancer 62:661, 1995; Barth, Cancer 78:1168, 1996). Based on the parameters altered by the indicated factors, biomaps are generated for the parameters integrin $\alpha_v$, ICAM-1, CD44, carcinoembryonic antigen (CEA) and $\alpha 5\beta_1$. Other markers of interest for adding to the biomap include EGF-R, HLA-Class I, HLA-DR, poly-Ig-receptor, IL-8, CA-19-9, E-cadherin, CD95, $\alpha_2\beta_1$, $\alpha_3\beta_1$, $\alpha_6\beta_1$, $\alpha_6\beta_4$, $\alpha_v$, laminin 5, urokinase-type plasminogen activator receptor (uPAR), MIP-3$\alpha$ and TNFR-I (Kelly, Am. J. Physiol. 263, G864-70, 1992; Moller, Int. J. Cancer, 57:371, 1994). Parameters of interest also include parameters indicative of cell damage and apoptosis including released cytoplasmic lactate dehydrogenase (LDH) or mitochondrial cytochrome c, appearance of APO2.7 epitope or active caspase-3 (Zhang, J. Immunol., 157:3980, 1996; Bussing, Cytometry 37:133, 1999). Parameters indicative of cell proliferation are also of interest and include Ki-67 and PCNA (Landberg, Cytometry, 13:230, 1992).

A database of biomaps is generated from a panel of assay combinations that include the differentiation-inducing agent butyrate, and known anti-cancer agents. DNA synthesis inhibitors, nucleoside analogs, topoisomerase inhibitors, and microtubule function inhibitors are screened and a biomap generated that shows the changes in the markers with the different anti-cancer agents. Such compounds are given in Weinstein, 1997, and The Pharmacologic Basis of Therapeutics. The biomaps with the known agents are used to compare to candidate anti-cancer drugs. This allows the recognition of the pathway(s) the candidate anticancer drug acts on, by comparing the changes in the level of the specific markers for known drugs affecting known pathways and the changes observed with the candidate drug. In addition, to further add to the utility of the biomap, one may include in the database reference biomaps generated from assay panels containing cells with genetic constructs that selectively target or modulate specific cellular pathways (e.g. ras, p53, NFκB, MAP kinase, etc), or cells that contain known genetic mutations (e.g. HT-29 cells contain a p53 mutation, etc.).

Example 11

Cancer Applications—Prostate Cancer

The present invention is applied for the screening of compounds for use in treating prostate cancer.

The human prostate carcinoma cell line LNCaP is used. Other prostate carcinoma cells lines that may replace LNCaP in the screen include DU-145, PPC-1, PC-3, MDA PCA 2b, JCA-1; normal prostate epithelial cells or primary tumor cells. $2\times10^4$ cells/ml are cultured in Dulbecco's Modified Eagle's Medium (DMEM) containing 10% FBS. Other media that may replace Dulbecco's Modified Eagle's Medium include RPMI, HAMS F12, DMEM containing charcoal-stripped serum or serum-free DMEM supplemented with 0.5% BSA. Other conditions of interest that may be used in subsequent assay combinations include assaying cultures with during log phase growth. Following overnight serum starvation the following are then applied for 24 hours: 5-dihydrotestosterone (10 nM), TNF-α (200 U/ml) and IL-6 (50 ng/ml). In subsequent panels one or more of IL-1 (10 ng/ml), IFN-γ (500 U/ml), TGF-α (10 ng/ml), epidermal growth factor (10 ng/ml) and IGF-II (10 nM); and/or neutralizing antibodies to autocrine factors, IGF-II, EGF, IL-6 or TGF-β or their receptors; and/or hypoxic conditions are added to the initial three factors or may replace one of the three factors. Standard concentrations of agents are employed as described in the literature (Sokoloff, Cancer 77:1862, 1996; Qiu, PNAS 95:3644, 1998; Hsiao, JBC 274:22373, 1999). Based on the parameters altered by the indicated factors, biomaps are generated for the parameters prostate specific antigen (PSA), E-cadherin, IL-8, epidermal growth factor receptor and vascular endothelial growth factor (VEGF). Other markers of interest for adding to the biomap include epidermal growth factor receptor, Her-2/neu EGF-R, HLA-class I, HLA-DR, CD95, α3, $α_2β_1$, $α_5β_1$, $α_vβ_3$, ICAM-1, MIP-3α and CD44. Parameters of interest also include parameters indicative of cell damage and apoptosis including released cytoplasmic lactate dehydrogenase (LDH) or mitochondrial cytochrome c, appearance of APO2.7 epitope or active caspase-3 (Zhang, J. Immunol., 157:3980, 1996; Bussing, Cytometry 37:133, 1999). Parameters indicative of cell proliferation are also of interest and include Ki-67 and PCNA (Landberg, Cytometry, 13:230, 1992).

A database of biomaps is generated from a panel of assay combinations that include the differentiation-inducing agents butyrate, calcitriol, and known anti-cancer agents that include anti-androgens, DNA synthesis inhibitors, nucleoside analogs, topoisomerase inhibitors, and microtubule function inhibitors. These factors are screened and a biomap generated that shows the changes in the markers with the different anti-cancer agents. Such compounds are given in Weinstein, 1997, and The Pharmacologic Basis of Therapeutics. The biomaps with the known agents are used to compare to candidate anti-cancer drugs. This allows the recognition of the pathway(s) the candidate anticancer drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. ras, p53, NFκB, MAP kinase, etc), or cells that contain known genetic mutations (e.g. LNCaP cells contain a K-ras mutation, etc.).

Example 12

Cancer Applications—Breast Cancer

The present invention is applied for the screening of compounds for use in treating breast cancer.

The human breast cell line MCF-7 is used. Other breast cancer cell lines that may replace MCF-2 in the screen include AU-565, HCC38, MCF-7, MDA-MB-231, MIB 157, SW-527, T47D, UACC-812, UACC- or ZR-75-1; primary mammary epithelial cells or primary tumor cells. $2 \times 10^4$ cells/ml are cultured in RPMI medium 10% FBS. Other media that may replace RPMI include Dulbecco's Modified Eagle's Medium containing 20% FBS. Other conditions of interest that may be used in subsequent assay combinations include assaying cultures with during log phase growth. Following overnight serum starvation the following are then applied for 24 hours: estrogen ($10^{-7}$ M), IL-4 (50 ng/ml), antibody to Her-2/neu, IL-1β (10 ng/ml). In subsequent panels one or more of IGF-I (5 nM), TNF-α (100 ng/ml), IFN-γ (200 U/ml), IL-13 (30 ng/ml), TGF-β (10 ng/ml), epidermal growth factor (10 ng/ml) and IL-6; and/or neutralizing antibodies to autocrine factors, IL-1, TGF-β or the receptor IGF-R I, are added to the initial three factors or may replace one of the three factors. Standard concentrations of agents are employed as described in the literature (Jackson, JBC 273:9994, 1998; He, PNAS 97:5768, 2000). Based on the parameters altered by the indicated factors, biomaps are generated for the parameters ICAM-1 (CD54), IL-8, MCP-1, E-cadherin, HLA-DR (CD74), CD44, carcinoembryonic antigen (CEA, CD66e) and $α_5β_1$. Other markers of interest for adding to the biomap include EGF-R, HLA-I, poly-Ig-receptor, IL-8, CA-19-9, CD95, $α_2β_1$, $α_3β_1$, $α_6β_1$, $α_6β_4$, $α_v$, laminin 5, urokinase-type plasminogen activator receptor (uPAR), and TNFR-I. Parameters of interest also include parameters indicative of cell damage and apoptosis including released cytoplasmic lactate dehydrogenase (LDH) or mitochondrial cytochrome c, appearance of APO2.7 epitope or active caspase-3 (Koester, Cytometry, 33:324, 1998; Zhang, J. Immunol., 157:3980, 1996; Bussing, Cytometry 37:133, 1999). Parameters indicative of cell proliferation are also of interest and include Ki-67 and PCNA (Landberg, Cytometry, 13:230, 1992).

A database of biomaps is generated from a panel of assay combinations that include the differentiation-inducing agent calcitriol, and known anti-cancer agents. anti-estrogens, DNA synthesis inhibitors, nucleoside analogs, topoisomerase inhibitors, and microtubule function inhibitors are screened and a biomap generated that shows the changes in the markers with the different anti-cancer agents. Such compounds are given in Weinstein, 1997, and The Pharmacologic Basis of Therapeutics. The biomaps with the known agents are used to compare to candidate anti-cancer drugs. This allows the recognition of the pathway(s) the candidate anticancer drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. ras, p53, NFκB, MAP kinase, etc), or cells that contain known genetic mutations (e.g. MDA-MB-231 cells contain a mutant p53, etc.).

Example 13

Angiogenesis Inhibitors

The present invention is applied for the screening of compounds that inhibit or modulate angiogenesis for treatment of vascularized neoplasms, rheumatoid arthritis and other disorders, or for conditions where vascular remodeling is beneficial.

Primary human umbilical vein endothelial cells are used. Other cells that may replace HUVEC in the screen include primary microvascular endothelial cells, aortic endothelial cells. $2 \times 10^4$ cells/ml are cultured to confluence in EGM-2 (Clonetics). Other media that may replace EGM-2 include EGM (Clonetics) and Ham's F12K medium supplemented with 0.1 mg/ml heparin and 0.03–0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984). Following overnight serum starvation, the following are then applied for 24 hours: VEGF (10 ng/ml), TNF-α (1 ng/ml) and bFGF (10 ng/ml). In subsequent panels one or more of IL-4 (20 ng/ml), IL-13 (20 ng/ml), EGF (10 ng/ml), hydrocortisone (2 ng/ml), thrombin (0.1 U/ml), hypoxic conditions (Xu, JBC 275:24583, 2000); and/or neutralizing antibodies to autocrine factors, such as TGF-β, IL-8 or IL-6 are added to the initial three factors or may replace one of the three factors. Standard concentrations of agents are employed as described in the literature (Thakker, JBC 274:10002, 1999; Kikuchi, NRMGK 23:12, 2000; Woltmann, Blood 95:3146, 2000; Wu, JBC 275:5096, 2000). Based on the parameters altered by the indicated factors, biomaps are generated for the parameters alphavbeta3, IL-8, VCAM-1, von Willebrand factor, E-selectin, fibronectin and uPAR (Friedlander, Science 270:1500, 1995; Zanetta, Int. J. Cancer 85, 281, 2000). Other markers of interest for adding to the biomap include: thrombomodulin, Tissue Factor, MMP-2, MMP-3, $\alpha_5\beta_1$, $\alpha_v\beta_5$, CD105 and CD31 (St. Croix, Science 289:1197, 2000; Friedlander, Science 270:1500, 1995; Bodey, Anticancer Res. 18:3621, 1998).

A database of biomaps is generated from a panel of assay combinations that include the known angiogenesis inhibitors and agents are screened and a biomap generated that shows the changes in the markers with the different anti-angiogenesis agents. Such anti-angiogenic compounds include growth factor signaling inhibitors and are given in The Pharmacologic Basis of Therapeutics. The biomaps with the known agents are used to compare to candidate anti-angiogenic drugs. This allows the recognition of the pathway(s) the candidate anti-angiogenic drug acts on, by comparing the changes in the level of the specific markers for known drugs affecting known pathways and the changes observed with the candidate drug. In addition, to further add to the utility of the biomap, one may include in the database reference biomaps generated from assay panels containing cells with genetic constructs that selectively target or modulate specific cellular pathways (e.g. ras, rho, NFκB, MAP kinase, etc), (e.g. HUVEC retrovirally transformed to overexpress bcl-2 (Zheng, J. Immunol 164:4665, 1999) or cells that contain known genetic mutations.

Example 14

Cardiovascular Disease

The present invention is applied for the screening of compounds for use in treating vascular dysfunction associated with cardiovascular disease, hypertension, diabetes and autoimmune disease.

Human aortic endothelial cells are used. Other cells that may replace human aortic endothelial cells include: human umbilical vein endothelial cells and human microvascular endothelial cells. $2\times10^4$ cells/ml are cultured to confluence in Endothelial cell growth medium-2 (EGM-2, Clonetics Corp.) containing Epidermal Growth Factor (100 ng/ml), hydrocortisone (1 ug/ml), Vascular Endothelial Growth Factor (10 ng/ml), Fibroblast Growth Factor B (30 ng/ml), Insulin Like Growth Factor-1 (10 nM) and 2% FBS. Other media that may replace EGM-2 include Medium 199 containing ECGF (50 ug/ml) and heparin (100 ug/ml); Medium 199 supplemented with 10% FBS; or endothelial cell basal medium (Clonetics Corp.) containing 1% bovine serum albumin (Thornton, Science 222:623, 1983; Jaffe, J. Clin. Invest, 52:2745, 1974; Wu, J Biol. Chem. 275:5096, 2000). The following are then applied for 24 hours: angiotensin-II (100 nM), TNF-α (5 ng/ml) and thrombin (10 U/ml) (Dietz, Basic Res. Cardiology 93 Suppl2:101, 1998; Lommi, Eur. Heart. J. 18:1620, 1997; Jafri, Semin. Thromb. Hemost. 23:543, 1997). In subsequent panels one or more of IL-1 (10 ng/ml), IFN-γ (100 ng/ml) IL-4 (20 ng/ml), IL-13 (30 ng/ml), TGF-beta (10 ng/ml), endothelin-1 (100 nM), aldosterone (1 uM), oxidized LDL (100 ug/ml), or minimally modified LDL are added to the initial three factors or may replace one of the three factors (Brown, J Clin Endocrinol Metab, 85:336, 2000; de Boer, J. Pathol. 188:174, 1999; Berliner, J. Clin. Invest. 85:1260, 1990). Standard concentrations of agents are employed as described in the literature (Kaplanski, J. Immunol 158:5435, 1997; Hofman, Blood 92:3064, 1998; Li, Circulation 102:1970, 2000; Essler, J B C 274:30361, 1999; Brown, J Clin Endocrinol Metab, 85:336, 2000).

Based on the parameters altered by the indicated factors, biomaps are generated for the parameters ICAM-1, vWF, E-selectin, P-selectin, IL-8, PAI-1, angiotensin converting enzyme (ACE, CD143), platelet-derived growth factor (PDGF) and MCP-1 (Devaux, Eur. Heart J. 18:470, 1997; Kessler, Diabetes Metab. 24:327, 1998; Becker, Z. Kardiol. 89:160, 2000; Kaplanski, J. Immunol. 158:5435, 1997; Li, Circulation 102:1970, 2000). Other markers of interest for adding to the biomap include, angiotensin-1 receptor, urokinase-type plasminogen activator receptor (uPAR, CD87), endothelin-1 receptor, tissue factor (CD142), fibrinogen-binding activity, MIG chemokine, and CD36 (Paramo, Br. Med. J. 291:573, 1985; Fukuhara, Hypertension 35:353, 2000; Noda-Heiny, Arterioscler Thromb Vasc. Biol. 15:37, 1995; de Prost, J. Cardiovasc. Pharmacol., 25 Suppl2:S114, 1995; van de Stolpe, Thromb Haemost 75:182, 1996; Mach, J. Clin. Invest., 104:1041, 1999; Nicholson, Ann. N.Y. Acad. Sci., 902:128, 2000).

A database of biomaps is generated from a panel of assay combinations that include known cardioprotective agents including beta blockers and other hypertensive drugs, ACE inhibitors, AT1 antagonists, and anti-aldosterones; statins; and others, are screened and a biomap generated that shows the changes in the markers with the different anti-cancer agents. Such compounds are given in The Pharmacologic Basis of Therapeutics. The biomaps with the known agents are used to compare to candidate cardioprotective drugs. This allows the recognition of the pathway(s) the candidate drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. NFκB, MAP kinase, etc), or cells that contain known genetic mutations (e.g. CD36-deficiency, Yanai, Am. J. Med. Genet. 93:299, 2000, etc.).

Example 15

Regulators of T Cell Function—Naive T Cell Responses

The present invention is useful for identifying regulators of T cell mediated inflammation and immunity. A set of assay combinations that reproduces aspects of the response of the naïve T cells are used.

The immune cell stimulatory environment in vivo during pathogenic immunity is characterized by the presence of multiple biologically active agents including IL-1, IL-2, TNF-a, and IFN-γ, IL4, IL12, IL10, TGF beta, IL6, IL7 and IL15 and others (Picker, J. Immunol. 150:1122, 1993; Picker J. Immunol:150:1105, 1993; W. Paul, Fundamental Immunology, 4th Ed, 1998. Lippincott Williams & Wilkins Publishers). Optimized assay combinations for naive T cell responses will contain at least two, and preferably three, four or more of these biologically active agents in addition with a primary stimulus through the T cell receptor and secondary stimuli through co-stimulatory receptors. Concentrations of agents are standard according to the literature. Concentrations may also be determined experimentally as the amount required to saturate the relevant receptor.

Primary human cord blood mononuclear cells are used. Other cells that may replace these cells include isolated populations of naive CD4+ and/or CD8+T cells isolated from adult human peripheral blood T cells. Cord blood mononuclear cells are isolated from blood by Ficoll-hypaque density gradient centrifugation as described (Ponath, JEM 183:2437, 1996). Cells are then cultured at 106 cells/ml in RPMI containing 10% FBS and Staphylococcal Enterotoxin B (SEB) (1 ug/ml), anti-CD28 (10 ug/ml), and IL-12 (5 ng/ml). In subsequent panels one or more Staphylococcal Enterotoxin E (SEE), or toxic shock syndrome toxin (TSST), or antibody to CD3 (1 ug/ml) can replace or be included with SEB to provide T cell receptor stimulation. TCR stimulation through conventional antigens or alloantigen, as in the mixed lymphocyte culture. In subsequent panels one or more of IL-1 (10 ng/ml), IL-2 (1 ng/ml), IL-10, IL-4 (20 ng/ml), IL-13 (30 ng/ml), TGF-b (10 ng/ml), anti-CD49d, IL-6, IL-7, IL-15, IL-18; and/or neutralizing antibodies to autocrine factors, IL-2, TNF-$\alpha$, are added to the initial three factors or may replace the IL-12. Antibodies or ligands for CD49d and CD28 provide costimulatory signals. Other Alternative costimulatory signals of interest that may be substituted for anti-CD28 and anti-CD49d include antibodies or ligands to CD5, anti-ICOS, or anti-4-1BB. The TCR stimulus and biologically active factors are then applied for 24 hours: Other time points of interest include 6 hours, 72 hours or 5 days.

Based on the parameters altered by the indicated factors, biomaps are generated for the parameters CD69, alphaEbeta7 (CD103), IL-12R$\beta$2 (CD212), CD40L (CD154), intracellular TNF-$\alpha$, intracellular IL-2 and CXCR3. Other markers of interest for adding to the biomap include: ICAM-1, alpha4beta7, cutaneous lymphocyte antigen (CLA), CD40L (CD154), OX40 (CD134), FasL (CD178), CTLA-4 (CD152), L-selectin (CD62L), CCR5, CCR6, CCR7, CXCR4, CXCR5, IL-4R (CD124), CD26, CD38, CD30, intracellular IFN-$\gamma$, intracellular IL-4, CD25, CCR9, CCR2, CCR4, RANTES, MIP-1beta, CD71, CD223, ICOS, CDw137.

Parameters on T cells in the culture are analyzed by flow cytometry. Anti-CD3 and anti-CD4 antibodies are used to identify CD4+ and CD4- T cells, and non T cells. Antibodies to the selected parameters are used with two additional colors. Readout patterns for T cells cultured with and without SEB or costimulators can be distinguished.

A database of biomaps is generated from a panel of assay combinations that include the presence and absence of each biologically active factor; and anti-inflammatory drug compounds including inhibitors of T cell activation and/or T cell proliferation including calcineurin inhibitors, FK506, cyclosporin, mycophenolic acid, methotrexate; as well as immune stimulatory agents including pathogens or pathogen components, etc. are screened and biomaps generated that show the changes in the markers with the different agents. Such agents are given in The Pharmacologic Basis of Therapeutics. The biomaps with the known agents are used to compare to candidate drugs. This allows the recognition of the pathway(s) the candidate drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. NFAT, calcineurin, NF$\kappa$B, MAP kinase, etc), or cells that contain known genetic mutations, e.g. Jurkat cell lines that lack lck, CD45, etc. (Yamasaki, J. Biol. Chem. 272:14787, 1997).

Example 16

Regulators of T Cell Function—Adult and Memory T Cells

The present invention is useful for identifying regulators of T cell mediated inflammation and immunity. A set of assay combinations that reproduces aspects of the response of the adult T cells is used.

Adult human peripheral blood mononuclear cells are used. Other cells that may replace adult peripheral blood T cells include isolated populations of CD4+, CD8+, TCRgamma/delta, and/or memory T cells; T cell lines such as Jurkat, Hut 78, CEM, and T cell clones. Peripheral blood mononuclear cells are isolated from blood by Ficoll-hypaque density gradient centrifugation as described (Ponath, JEM 183:2437, 1996). Cells are then cultured at 106 cells/ml in RPMI containing 10% FBS and Staphylococcal Enterotoxin B (SEB) (1 $\mu$g/ml), anti-CD28 (10 ug/ml), and IL-12 (5 ng/ml). In subsequent panels one or more Staphylococcal Enterotoxin E (SEE), or toxic shock syndrome toxin (TSST), or antibody to CD3 (1 ug/ml) can replace or be included with SEB to provide T cell receptor stimulation. TCR stimulation through conventional antigens or alloantigen, as in the mixed lymphocyte culture. In subsequent panels one or more of IL-1 (10 ng/ml), IL-2 (1 ng/ml), IL-10, IL-4 (20 ng/ml), IL-13 (30 ng/ml), TGF-beta (10 ng/ml), anti-CD49d, IL-6, IL-7, IL-15, IL-18; and/or neutralizing antibodies to autocrine factors, IL-4, IFN-$\gamma$, IL-2, TNF-$\alpha$, are added to the initial three factors or may replace the IL-12. Antibodies or ligands for CD49d and CD28 provide costimulatory signals. Other alternative costimulatory signals of interest that may be substituted for anti-CD28 and anti-CD49d include antibodies or ligands to CD5, anti-ICOS, or anti-4-1 BB. The TCR stimulus and biologically active factors are then applied for 24 hours: Other time points of interest include 6 hours, 72 hours or 5 days.

Standard concentrations of agents and factors are employed as described in the literature. T cells in the cultures are analyzed by flow cytometry. Based on the parameters altered by the indicated factors, biomaps are generated for the parameters CD40L (CD154), CD69, Ox40 (CD134), intracellular $\gamma$IFN, TNF$\alpha$, IL-2, FAS ligand (CD178), alpha e-integrin (CD103), CTLA4 (CD152), and IL-12 receptor beta2 (CD212). Other parameters of interest include CD95, CD45RO, alph4beta7, alpha4beta7, alpha4beta1, L-selectin (CD62L), CCR7, CCR5, CXCR3, CXCR4, CCR6, CXCR5, CCR9, CCR2, CCR4, RANTES, MIP1beta, CD71, CD223, ICOS, CDw137, CD26, CD30, CD38, cutaneous lymphocyte antigen (CLA) and IL-4R alpha chain.

Parameters on T cells in the culture are analyzed by flow cytometry. Anti-CD3 and anti-CD4 antibodies are used to identify CD4+ and CD4-T cells, and non T cells. CD95, CD45RO and/or CD45RA are used to identify memory T cells. Antibodies to the selected parameters are used with 2–4 additional colors. Readout patterns for T cells cultured with and without SEB or costimulators can be distinguished.

A database of biomaps is generated from a panel of assay combinations that include the presence and absence of each biologically active factor; and anti-inflammatory drug compounds including inhibitors of T cell activation and/or T cell proliferation including calcineurin inhibitors, FK506, cyclosporin, mycophenolic acid, methotrexate; as well as immune stimulatory agents including pathogens or pathogen components, etc. are screened and biomaps generated that show the changes in the markers with the different agents. Such compounds are given in The Pharmacologic Basis of Therapeutics. The biomaps with the known agents are used to compare to candidate agents. This allows the recognition of the pathway(s) the candidate agent acts on, by comparing the changes in the level of the specific markers for known drugs affecting known pathways and the changes observed with the candidate agent. In addition to further add to the utility of the biomap, one may include in the database reference biomaps generated from assay panels containing cells with genetic constructs that selectively target or modulate specific cellular pathways (e.g. NFAT, calcineurin, NFκB, MAP kinase, etc), or cells that contain known genetic mutations, e.g. Jurkat cell lines that lack Ick, CD45, etc. (Yamasaki, J. Biol. Chem. 272:14787, 1997).

Example 17

Regulators of T Cell Function—TH1 Responses

The present invention is applied for the screening of compounds that inhibit the activation of Th1 lymphocytes.

Human peripheral blood CD4+ T cells are employed. Other cells that may be employed include the T cell line KIT-225, human peripheral blood CD3+ cells, human cord blood T cells, etc. Cells are isolated from human peripheral blood mononuclear cells utilizing Ficoll-hypaque density gradient centrifugation as described (Ponath, JEM 183:2437, 1996). Following adherence of cells to plastic, CD4+ cells are isolated from non-adherent cells using Miltenyi magnetic beads as described (Andrew, JI 166:103, 2001). Alternatively, purified human CD4+ T cells are obtained from a commercial source (Clonetics Corp.). Purified CD4+ lymphocytes are then cultured at $10^6$ cells/ml in DMEM containing 10% FBS and anti-CD3 (1 μg/ml), anti-CD28 (10 μg/ml), IL-2 (4 ng/ml), IL-12 (5 ng/ml) and neutralizing antibody to IL-4 (1 μg/ml) for 3 days. In subsequent panels one or more of PHA (1 μg/ml) IL-1 (20 ng/ml), IL-6, IL-7, neutralizing antibody to IL-4, are added to the initial three factors or may replace one of the three factors. Other time points of interest include 5 and 7 days.

Based on the parameters altered by the indicated factors, biomaps are generated for the parameters CD40L (CD154), alpha4beta7, cutaneous lymphocyte antigen (CLA), CXCR3 (CD183), IL-12receptor beta2 (CD212), intracellular IFN-γ, intracellular TNF-α, and intracellular IL-2. Other markers of interest for adding to the biomap include: ICAM-1, OX40 (CD134), FasL (CD178), CTLA-4 (CD152), L-selectin (CD62L), CCR5 (CD195), CCR6, CCR7 (CDw197), CXCR4 (CD184), CXCR5, IL-4R (CD124), CD26, CD38, CD30, P-selectin-ligand activity, intracellular IL-4, intracellular IL-5 and intracellular IL-13.

Parameters on T cells in the culture are analyzed by flow cytometry. Anti-CD3 and anti-CD4 antibodies are used to identify CD4+ and CD4− T cells, and non T cells. CD45RO and/or CD45RA are used to identify memory T cells. Antibodies to the selected parameters are used with 2–4 additional colors. Readout patterns for T cells cultured with and without SEB or costimulators can be distinguished.

A database of biomaps is generated from a panel of assay combinations that include the presence and absence of each biologically active factor; and anti-inflammatory drug compounds including inhibitors of T cell activation and/or T cell proliferation including calcineurin inhibitors, FK506, cyclosporin, mycophenolic acid, methotrexate; as well as immune stimulatory agents including pathogens or pathogen components, etc. are screened and biomaps generated that show the changes in the markers with the different agents. Such compounds are given in The Pharmacologic Basis of Therapeutics. The biomaps with the known agents are used to compare to candidate agents. This allows the recognition of the pathway(s) the candidate agent acts on, by comparing the changes in the level of the specific markers for known drugs affecting known pathways and the changes observed with the candidate agent. In addition to further add to the utility of the biomap, one may include in the database reference biomaps generated from assay panels containing cells with genetic constructs that selectively target or modulate specific cellular pathways (e.g. NFAT, calcineurin, NFkB, MAP kinase, etc), or cells that contain known genetic mutations, e.g. Jurkat cell lines that lack Ick, CD45, etc. (Yamasaki, J. Biol. Chem. 272:14787, 1997).

Example 18

Regulators of T Cell Function—TH2 Responses

The present invention is applied for the screening of compounds that inhibit the activation of Th2 lymphocytes.

Human peripheral blood CD4+ T cells are employed. Other cells that may be employed include human peripheral blood CD3+ cells. Cells are isolated from human peripheral blood mononuclear cells utilizing Ficoll-hypaque density gradient centrifugation as described (Ponath, JEM 183:2437, 1996). Following adherence of cells to plastic, CD4+ cells are isolated from non-adherent cells using Miltenyi magnetic beads as described (Andrew, JI 166:103, 2001). Purified CD4+ lymphocytes are then cultured at $10^6$ cells/ml in DMEM containing 10% FBS and anti-CD3 (1 μg/ml), anti-CD28 (10 μg/ml 1) IL-2 (4 ng/ml), IL-4 (5 ng/ml) and neutralizing antibody to IFN-γ (1 μg/ml) for 3 days. In subsequent panels one or more of PHA (1 μg/ml) IL-1 (20 ng/ml), 1L-6, IL-7, IL-13, neutralizing antibody to IL-12, are added to the initial three factors or may replace one of the three factors. Other time points of interest include 5 and 7 days.

Based on the parameters altered by the indicated factors, biomaps are generated for the parameters alpha4beta7, alphaEbeta7, cutaneous lymphocyte antigen (CLA), CCR3, intracellular IL-2, intracellular TNF-cc, IL-4, IL-5 and IL-13. Other markers of interest for adding to the biomap include: ICAM-1, CD40L, OX40 (CD134), FasL (CD178), CTLA-4 (CD152), L-selectin (CD62L), CCR3, CCR5, CCR6, CCR7, CXCR4, CXCR5, IL-4R (CD124), CD26, CD38, CD30, P-selectin ligand activity and intracellular IFN-γ.

Parameters on T cells in the culture are analyzed by flow cytometry. Anti-CD3 and anti-CD4 antibodies are used to identify CD4+ and CD4− T cells, and non T cells. CD45RO and/or CD45RA are used to identify memory T cells (Teraki, J. Immunol 159:6018, 1997; Waldrop, J. Immunol. 161:5284, 1998; Picker, Blood, 86:1408, 1995). Antibodies to the selected parameters are used with 2–4 additional colors. Readout patterns for T cells cultured with and without SEB or costimulators can be distinguished.

A database of biomaps is generated from a panel of assay combinations that include the presence and absence of each biologically active factor; and anti-inflammatory drug compounds including inhibitors of T cell activation and/or T cell proliferation including calcineurin inhibitors, FK506, cyclosporin, mycophenolic acid, methotrexate; as well as immune stimulatory agents including pathogens or pathogen components, etc. are screened and biomaps generated that show the changes in the markers with the different agents. Such compounds are given in The Pharmacologic Basis of Therapeutics. The biomaps with the known agents are used to compare to candidate agents. This allows the recognition of the pathway(s) the candidate agent acts on, by comparing the changes in the level of the specific markers for known drugs affecting known pathways and the changes observed with the candidate agent. In addition to further add to the utility of the biomap, one may include in the database reference biomaps generated from assay panels containing cells with genetic constructs that selectively target or modulate specific cellular pathways (e.g. NFAT, calcineurin, NFκB, MAP kinase, etc), or cells that contain known genetic mutations, e.g. Jurkat cell lines that lack lck, CD45, etc. (Yamasaki, J. Biol. Chem. 272:14787, 1997).

Example 19

Regulators of Monocyte Functions

The present invention is applied for the screening of compounds for modulating monocyte/macrophage functions.

Human peripheral blood monocytes are used. Other cells that may replace human peripheral blood monocytes include: bone-marrow derived monocytes, monocytes isolated by elutriation or negative magnetic bead isolation, and monocyte cell lines THP-1 or U937. Four$\times 10^6$ peripheral blood mononuclear cells/ml are cultured in RPMI containing 10% fetal bovine serum for 2 hours. Non-adherent lymphocytes are removed by gentle washing. The following are then applied for 24 hours: IL-1 (1 ng/ml), IFN-γ (50 ng/ml) and TGF-beta (10 ng/ml) (Dietz, Basic Res. Cardiology 93 Suppl2:101, 1998; Lommi, Eur. Heart. J. 18:1620, 1997; Jafri, Semin. Thromb. Hemost. 23:543, 1997). In subsequent panels one or more of lipopolysaccharide (10 ng/ml), GM-CSF (10 ng/ml), TNF-α (5 ng/ml), IL-4 (20 ng/ml), IL-13 (30 ng/ml), osteopontin (10 ng/ml), thrombin (10 U/ml), CD40L, oxidized LDL (100 ug/ml), or minimally modified LDL are added to the initial three factors or may replace one of the three factors (Brown, J Clin Endocrinol Metab, 85:336, 2000; Ashkar, Science 287:860, 2000; de Boer, J. Pathol. 188:174, 1999; Berliner, J. Clin. Invest. 85:1260, 1990). Standard concentrations of agents are employed as described in the literature (Kaplanski, J. Immunol 158:5435, 1997; Hofman, Blood 92:3064, 1998; Li, Circulation 102:1970, 2000; Essler, JBC 274:30361, 1999; Brown, J Clin Endocrinol Metab, 85:336, 2000). Based on the parameters altered by the indicated factors, biomaps are generated for the parameters ICAM-1, Mac-1 (CD11b/CD18), IL-8, HLA-DR, TNF-α, IL-12 and MCP-1 (Devaux, Eur. Heart J. 18:470, 1997; Kessler, Diabetes Metab. 24:327, 1998; Becker, Z. Kardiol. 89:160, 2000; Kaplanski, J. Immunol. 158:5435, 1997; Li, Circulation 102:1970, 2000). Other markers of interest for adding to the biomap include CD14, PAI-1, urokinase-type plasminogen activator receptor (uPAR, CD87), IL-10, IL-18, tissue factor, fibrinogen-binding activity, MIG chemokine, TARC, MDC, RANTES, CD25, CD80, CD86, CD40 and CD36 (Paramo, Br. Med. J. 291:573, 1985; Fukuhara, Hypertension 35:353, 2000; Noda-Heiny, Arterioscler Thromb Vasc. Biol. 15:37, 1995; de Prost, J. Cardiovasc. Pharmacol., 25 Suppl2:S114, 1995; van de Stolpe, Thromb Haemost 75:182, 1996; Mach, J. Clin. Invest., 104:1041, 1999; Nicholson, Ann. N.Y. Acad. Sci., 902:128, 2000). A database of biomaps is generated from a panel of assay combinations that include known anti-atherogenic agents including statins and others, are screened and a biomap generated that shows the changes in the markers with the different anti-cancer agents. Such compounds are given in The Pharmacologic Basis of Therapeutics. The biomaps with the known agents are used to compare to candidate agents. This allows the recognition of the pathway(s) the candidate drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. NFκB, MAP kinase, etc), or cells that contain known genetic mutations (e.g. CD36-deficiency, Yanai, Am. J. Med. Genet. 93:299, 2000, etc.).

Based on the parameters altered by the indicated factors, biomaps are generated for the parameters ICAM-1, Mac-1 (CD11b/CD18), IL-8, HLA-DR, TNF-α, IL-12 and MCP-1 (Devaux, Eur. Heart J. 18:470, 1997; Kessler, Diabetes Metab. 24:327, 1998; Becker, Z. Kardiol. 89:160, 2000; Kaplanski, J. Immunol. 158:5435, 1997; Li, Circulation 102:1970, 2000). Other markers of interest for adding to the biomap include CD14, PAI-1, urokinase-type plasminogen activator receptor (uPAR, CD87), IL-10, IL-18, tissue factor, fibrinogen-binding activity, MIG chemokine, CD25, CD80, CD86, CD40 and CD36 (Paramo, Br. Med. J. 291:573, 1985; Fukuhara, Hypertension 35:353, 2000; Noda-Heiny, Arterioscler Thromb Vasc. Biol. 15:37, 1995; de Prost, J. Cardiovasc. Pharmacol., 25 Suppl2:S114, 1995; van de Stolpe, Thromb Haemost 75:182, 1996; Mach, J. Clin. Invest., 104:1041, 1999; Nicholson, Ann. N.Y. Acad. Sci., 902:128, 2000).

A database of biomaps is generated from a panel of assay combinations that include known anti-atherogenic agents including statins and others, are screened and a biomap generated that shows the changes in the markers with the different anti-cancer agents. Such compounds are given in The Pharmacologic Basis of Therapeutics. The biomaps with the known agents are used to compare to candidate agents. This allows the recognition of the pathway(s) the candidate drug acts on, by comparing the changes in the level of the specific markers for known drugs affecting known pathways and the changes observed with the candidate drug. In addition to further add to the utility of the biomap, one may include in the database reference biomaps generated from assay panels containing cells with genetic constructs that selectively target or modulate specific cellular pathways (e.g. NFκB, MAP kinase, etc), or cells that contain known genetic mutations (e.g. CD36-deficiency, Yanai, Am. J. Med. Genet. 93:299, 2000, etc.).

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

What is claimed is:

1. A method for determining the activity of a biologically active agent according to its effect on cellular signaling pathways, the method comprising:

contacting a candidate biologically active agent with a cell culture assay combination, wherein said cell culture assay combination comprises human cells in an inflammatory state as a result of adding to said culture at least three of the factors selected from the group consisting of TNF-α, TNF-β, IL-1, IL-2, IL-4, IL-12, IL-13, Staphylococcal Enterotoxin B (SEB); Staphylococcal Enterotoxin E (SEE), toxic shock syndrome toxin (TSST), anti-CD3 antibody, anti-T cell receptor antibody, histamine and IFN-γ in an amount and for a time sufficient to induce said inflammatory state;

recording changes in at least two different cellular parameter readouts, said parameters being selected from the group consisting of ICAM-1, VCAM-1, E-selectin, P-selectin, IL-8, CD31, CD40, HLA-DR, eotaxin-3, MCP-1, and MIG, after introduction of said agent;

deriving a biomap dataset from said changes in parameter readouts wherein said biomap comprises data normalized to control data on the same cell type under control conditions comprising said at least three factors and lacking said biologically active agent, and wherein output parameters are optimized so that the biomap dataset is sufficiently informative that it can discriminate the mode of action or functional effect of an agent;

comparing said biomap dataset to a reference biomap dataset to determine the presence of variation, wherein the presence of variation indicates a difference in the effect of the agent on a cellular signaling pathway.

2. The method according to claim 1, wherein at least four parameters are measured.

3. The method according to claim 1, further comprising the step of contacting said candidate biologically active agent with a panel comprising a plurality of said cell culture assay combinations.

4. The method according to claim 3, wherein said assay combinations in said panel vary in the factors or cells that are present.

5. The method according to claim 3, wherein at least one assay combination in said panel comprises endothelial cells and peripheral blood mononuclear cells.

6. The method according to claim 3, wherein at least one assay combination in said panel comprises endothelial cells and T cells.

7. The method according to claim 3, wherein at least one assay combination in said panel comprises endothelial cells and B cells.

8. The method according to claim 3, wherein at least one assay combination in said panel comprises endothelial cells and natural killer (NK) cells.

9. The method according to claim 3, wherein at least one assay combination in said panel comprises endothelial cells and monocytes.

10. The method according to claim 3, wherein at least one assay combination in said panel comprises endothelial cells and dendritic cells.

11. The method according to claim 1, further comprising the step of adding an inhibitor of a known pathway to said cell culture assay combination, whereby when said compound has no effect on said parameters in the portion containing said inhibitor as compared to said a cell culture assay combination in which said inhibitor is absent, said biologically active agent is affecting the same pathway as said inhibitor compound.

12. The method according to claim 1, wherein activity of said factor is provided with a mimetic agent.

13. The method according to claim 1 wherein said cells are incubated with said at least three factors for about 6 to 72 h prior to adding said agent.

14. A method for determining the activity of a biologically active agent according to its effect on cellular signaling pathways, the method comprising:

contacting a candidate biologically active agent with a cell culture assay combination, wherein said cell culture assay combination comprises human endothelial cells in an inflammatory state as a result of adding to said culture at least three of the factors selected from the group consisting of TNF-α, TNF-β, IL-1, IL-2, IL-4, IL-12, IL-13, Staphylococcal Enterotoxin B (SEB); Staphylococcal Enterotoxin E (SEE), toxic shock syndrome toxin (TSST), anti-CD3 antibody, anti-T cell receptor antibody, histamine and IFN-γ in an amount and for a time sufficient to induce said inflammatory state;

recording changes in at least two different cellular parameter readouts, said parameters being selected from the group consisting of ICAM-1, VCAM-1 E-selectin, P-selectin, IL-8, CD31, CD40, HLA-DR, eotaxin-3, MCP-1, and MIG, after introduction of said agent;

deriving a biomap dataset from said changes in parameter readouts wherein said biomap comprises data normalized to control data on the same cell type under control conditions lacking said biologically active agent, and wherein output parameters are optimized so that the biomap dataset is sufficiently informative that it can discriminate the mode of action or functional effect of an agent;

comparing said biomap dataset to a reference biomap dataset to determine the presence of variation, wherein the presence of variation indicates a difference in the effect of the agent on a cellular signaling pathway.

15. The method according to claim 14, wherein said endothelial cells are primary cells.

16. The method according to claim 15, wherein said primary cells are HUVEC.

* * * * *